United States Patent
Mandadi et al.

(10) Patent No.: US 11,254,965 B2
(45) Date of Patent: Feb. 22, 2022

(54) METHODS, COMPOSITIONS, AND SYSTEMS FOR CULTURING AND CHARACTERIZING FASTIDIOUS PLANT MICROBES

(71) Applicant: THE TEXAS A&M UNIVERSITY, College Station, TX (US)

(72) Inventors: Kranthi K. Mandadi, Weslaco, TX (US); Sonia C. Irigoyen, Weslaco, TX (US); Shankar Pant, Weslaco, TX (US); Manikandan Ramasamy, Weslaco, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 67 days.

(21) Appl. No.: 16/541,781

(22) Filed: Aug. 15, 2019

(65) Prior Publication Data

US 2019/0367962 A1 Dec. 5, 2019

Related U.S. Application Data

(63) Continuation-in-part of application No. 15/353,645, filed on Nov. 16, 2016, now Pat. No. 11,041,143.

(60) Provisional application No. 62/255,823, filed on Nov. 16, 2015.

(51) Int. Cl.
```
C12N 1/20      (2006.01)
C12Q 1/04      (2006.01)
C12Q 1/689     (2018.01)
C12N 15/11     (2006.01)
C12N 5/04      (2006.01)
```

(52) U.S. Cl.
CPC ............... *C12Q 1/04* (2013.01); *C12N 5/04* (2013.01); *C12N 15/11* (2013.01); *C12Q 1/689* (2013.01); *C12N 2310/20* (2017.05)

(58) Field of Classification Search
None
See application file for complete search history.

(56) References Cited

U.S. PATENT DOCUMENTS

2008/0153102 A1 6/2008 Huang et al.
2009/0126038 A1 5/2009 Van De Craen

FOREIGN PATENT DOCUMENTS

CN 102766650 A 11/2012

OTHER PUBLICATIONS

Sechler et al. (Phytopathology 99.5 (2009): 480-486). (Year: 2009).*
Mugnier, (Phytopathology 77.4 (1987): 539-542). (Year: 1987).*
Hatakeyama et al. (PloS one 8.1 (2013): e54745). (Year: 2013).*
Qu et al. (Journal of eukaryotic microbiology 54.6 (2007): 465-467). (Year: 2007).*
Mohan, Sara. Snakin genes from potato: overexpression confers blackleg disease resistance. Diss. Lincoln University, 2011. (Year: 2011).*
Lata, et al. (Plant cell, tissue and organ culture 85.3 (2006): 353-359). (Year: 2006).*
Collier et al. (The Plant Journal 43.3 (2005): 449-457). (Year: 2005).*
Taylor et al. (Agrobacterium Protocols. Humana Press, 2006. 155-168). (Year: 2006).*
Desoignies Nicolas et al., In Vitro Dual Culture of Polymyxa betae in Agrobacterium rhyzogenes Transformed Sugar Beet Hairy Root in Liquid Media, Journal of Eukaryotic Microbiology (Sep. 2011), vol. 58, No. 5, pp. 424-425.
Mugnier J. "Establishment of New Axenic Hairy Root Lines by Inoculation with Agrobacterium-Rhyzogenes," Plant Cell Report, (1988), vol. 7, No. 1, , ISSN 0721-7714, pp. 9-10.
Tada et al. (Science 321.5891 (2008): 952-956). (Year: 2008).
Sanghamitra Khandual, et al., "Rapid, Efficient and High-Performance Protocol for Agrobacterium rhizogenes-Mediated Hairy Root Transformation of the Common Bean Phaseolus vulgaris", Advances in Bioscience and Biotechnology, 2014, vol. 5, pp. 333-339.
Chen et al. "Establishing and Fine-Tuning an in Planta System for Potato Zebra Chip Disease Research in California" 2010 Zebra Chip Reporting Session (2010): 19. (Year: 2010).
Porter, Critical Reviews in Plant Sciences, 10(4):387-421 (1991). (Year: 1991).
Li et al. (Journal of Microbiological Methods 78 (2009) 59-65). (Year: 2009).
Estrada-Navarrete, et al. (Nature Protocols 2.7 (2007): 1819). (Year: 2007).
Ferrari et al. (Applied And Environmental Microbiology, May 2009, p. 3352-3354). (Year: 2009).
Kamagata et al. (Microbes and Environments 20.2 (2005): 85-91). (Year: 2005).
Purcell et al. (Annu. Rev. Phytopathol. 1996. 34:131-51). (Year: 1996).

(Continued)

*Primary Examiner* — Charles Logsdon
(74) *Attorney, Agent, or Firm* — Hogan Lovells US LLP

(57) ABSTRACT

Numerous plant microbes, including the vascular-limited *Candidatus* spp.—causal agents of citrus greening and potato zebra chip diseases—are non-culturable. The present disclosure relates, according to some embodiments, to compositions, methods and systems for culturing such organisms. For example, the present disclosure relates to methods for culturing, propagating, and characterizing fastidious vascular-colonizing microbes using a hairy root system (e.g., in vitro, in planta). The present disclosure relates, in some embodiments, to methods for cultivating a fastidious plant microbe including: contacting a plant (e.g., a tomato plant, a potato plant, a citrus plant) colonized by a fastidious plant microbe (e.g., *Xylella fastidiosa*, *Candidatus* Liberibacter spp.) with a suspension of *R. rhizogenes* under conditions that permit induction of hairy roots colonized with the fastidious plant microbe, and propagating the colonized microbial hairy roots.

16 Claims, 32 Drawing Sheets
(28 of 32 Drawing Sheet(s) Filed in Color)

Specification includes a Sequence Listing.

(56) References Cited

OTHER PUBLICATIONS

Qu Xinshun et al., "In vitro culture of the obligate parasite Spongospora subterranean (Cercozoa:Plasmodiiophorida) associated with root-inducing transferred-DNA transformed potato hairy roots," Journal of Eukaryotic Microbiology, vol. 54, No. 6, Nov. 2007 pp. 465-467.
European Search Report dated May 15, 2019 issued in EP 16 867 069.3.
Mily Ron, et al., "Hairy Root Transformation Using Agrobacterium rhizogenes as a Tool for Exploring Cell Type-Specific Gene Expression and Function Using Tomato as a Model", Plant Physiology, Oct. 2014, vol. 166, pp. J55-J469.
International Search Report and Written Opinion dated Feb. 27, 2017 in connection with International Application No. PCT/US2016/062342, 9 pages.
Katherine Noorda-Nguyen, et al., "Agrobacterium rhizogenes Generates Transgenic Hairy Roots in Garica papaya L.: A New Approach for Studying and Improving Resistance to the Root-rot Pathogen, Phytophthora palmivora", Irransgenic Plant Journal, 2010, vol. 4, No. 1, pp. 94-96.
David Gilchrist, et al., "Application of Agrobacterium Rhizogenes-Mediated Transformation Strategies for a Rapid High lrhroughput Screen for Genetic Resistance to Pierce's Disease in Grape that Maintains the Clonal Integrity of the Recipient Host", Pierce's Disease Research Symposium, Dec. 15-18, 2002, San Diego, California, pp. 11-12.
Mila Kereszt, et al., "Agrobacterium Rhizogenes-Mediated Transformation of Soybean to Study Root Biology", Nature Protocols, 2007, vol. 2, No. 4, pp. 948-952.

* cited by examiner

METHODS, COMPOSITIONS, AND SYSTEMS FOR CULTURING AND CHARACTERIZING FASTIDIOUS PLANT MICROBES

CROSS-REFERENCE TO RELATED APPLICATIONS

This application is a continuation-in-part of U.S. application Ser. No. 15/353,645 filed Nov. 16, 2016, which claimed priority to and the benefit of U.S. Application No. 62/255,823 filed Nov. 16, 2015, the entire contents of both applications are hereby incorporated in this disclosure by reference.

SEQUENCE LISTING

The instant application contains a Sequence Listing which has been submitted electronically in ASCII format and is hereby incorporated by reference in its entirety. Said ASCII copy, created on Nov. 12, 2021, is named 026837-104013_SL.txt and is 10,025 bytes in size.

FIELD OF THE DISCLOSURE

The present disclosure relates, in some embodiments, to methods, compositions, and systems for culturing and characterizing fastidious plant microbes using plant hairy root cultures. Furthermore, using the 'microbial hairy roots' a rapid and high throughput screening bioassay (up to four times faster) were created to evaluate diverse antimicrobial therapies such as overexpression of disease resistance genes, CRISPR-Cas9-based genome-editing of susceptibility genes, as well as bactericides and immune modulators.

BACKGROUND OF THE DISCLOSURE

Estimates of food and agriculture organizations project that global food production has to increase 60% by 2050 to meet the demands of the rising world population. On top of the rising demand, annual agricultural crop losses caused by plant pathogens may run into upwards of 40%. Fastidious and obligate phytopathogens alone may be devastating to several food and commodity crops. Fastidious plant microbes are plant microbes that do not grow outside of its natural host and as such cannot be cultured in the laboratory to allow for study. Fastidious microbes are characterized by their inability to live outside their natural hosts given that they are obligate parasites of plants. Current studies rely on laborious and time-consuming (~12 to 24 months) transgenic and transient methods using mature plants and grafting procedures.

For example, xylem-limited *Xylella fastidiosa* infects over 100 plant species including grapevine, citrus, coffee and almonds. Similarly, phloem-limited *Candidatus* Liberibacter spp. are emerging destructive microbes causing yield losses (e.g., severe losses) in diverse plant families, including Solanaceae (potato, tomato, pepper and tobacco), Apiaceae (carrot and celery), *Rosaceae* (pear, apple and blackthorn), and *Rutaceae* (*citrus* spp.). Zebra chip disease in potato may be caused by *Candidatus* Liberibacter solanacearum (Lso), which also infects tomatoes, pepper and tobacco. Lso is transmitted by an insect vector, potato psyllid (*Bactericera cockerelli*). Since being designated as an emerging disease in 2004, zebra chip disease has been documented in several commercial potato growing regions of the United States, Mexico, Central America, and New Zealand. In Texas alone, zebra chip disease is estimated to affect 35% of cultivated potato acreage, causing annual crop losses of approximately $25 million USD. Similarly, citrus greening or Huanglongbing (HLB) disease caused by the *Candidatus* Liberibacter asiaticus (Las) may be the most devastating disease of citrus today, and threatens citrus production worldwide. HLB is transmitted by the insect vector, Asian Citrus psyllid (*Diaphorina citri*). In 2006-2011, in Florida alone, HLB caused losses upwards of $4.5 billion USD. These and other diseases caused by fastidious plant microbes are a major threat to U.S. and global agriculture production. It is imperative to curtail these agricultural losses in order to overcome the impending global food security challenge.

A major bottleneck to characterizing CLas and CLso is their inability to grow outside the plant and insect hosts. It is estimated that >99% of all microorganisms from any environment are non-cultivable in the laboratory[8]. Attempts have been made to create suitable artificial growth media and culture conditions to cultivate such fastidious microbes, including CLas. These include specialized modifications to standard growth media composition, modification to growth conditions (e.g., temperature, pH, incubation time, inoculum size and $CO_2/O_2$ ratio), co-culturing with helper and cooperative microbes, in biofilms or in other simulated natural environments[8, 9, 10, 11, 12, 13, 14] These approaches have met with limited success to culture CLas and CLso and as such do not readily facilitate screening of antimicrobials. Accordingly, a need has arisen for improved (e.g., easy, rapid, and/or scalable) culturing and functional characterization of fastidious vascular-colonizing microbes.

SUMMARY

The present disclosure relates, in some embodiments, to methods, compositions, and systems for culturing and characterizing fastidious microbes using hairy roots (e.g., *R. rhizogenes*-mediated hairy roots induced directly from infected plants or plant tissues). *R. rhizogenes*-mediated hairy roots induced directly from the infected plants or plant tissues may provide an easy, rapid and scalable platform to culture and characterize the fastidious vascular-colonizing microbes.

Hairy root cultures are a valuable tool used in functional biology, biotechnology, metabolic engineering, molecular pharming, and studies of root-rhizosphere interactions[15, 16]. Hairy roots can be readily induced from diverse plant tissues upon infection by a soil bacterium, *Rhizobium rhizogenes*[17]. In a manner similar to its related cousin, *Agrobacterium tumefaciens*, *R. rhizogenes* introduces its root-inducing (Ri) transfer-DNA (Ri T-DNA) encoding the root locus (rol) genes, into the plant genome. The expression of rol genes in planta stimulate production/transport of the plant hormone, auxin, and induces hairy root initiation and proliferation. An important feature of hairy roots is that they are anatomically and metabolically similar to normal roots and possess intact xylem and phloem vasculature connected to the source explant[16, 18, 19]. The plant hairy roots support fastidious microbes and as such can be used as 'biological vessels' to cultivate fastidious microbes that reside in the vasculature.

For example, Lso and Las may be cultured in hairy roots induced directly from Lso- and Las-infected tomato, potato and citrus plants or plant tissues. Because hairy roots are organized and stable tissues, the microbe-colonized hairy root tissues may be clonally propagated for numerous applications (e.g., characterization of the fastidious microbes).

The present disclosure relates, in some embodiments, to methods for cultivating a fastidious plant microbe (e.g., a fastidious plant pathogen). For example, a method may comprise contacting a plant (e.g., a tomato plant, a potato plant, a citrus plant) colonized by a fastidious plant microbe (e.g., *Xylella fastidiosa*, *Candidatus* Liberibacter spp.) with a suspension of *R. rhizogenes* under conditions that permit induction of hairy roots colonized with the fastidious plant microbe. A fastidious plant microbe may then be cultivated by propagating the colonized microbial hairy roots. In some embodiments, a cultivated plant microbe may be *Candidatus* Liberibacter spp. (e.g., *Candidatus* Liberibacter solanacearum (Lso) and/or *Candidatus* Liberibacter asiaticus (Las)). According to some embodiments, *R. rhizogenes* may include both a Ri-DNA plasmid and a T-DNA plasmid and the T-DNA plasmid may encode a first exogenous transgene (e.g., a gene encoding an autofluorescent protein). According to some embodiments, a plant may include a first exogenous transgene.

In some embodiments, contacting a plant colonized by a fastidious microbe with a suspension of *R. rhizogenes* may include wounding one or more surfaces of a plant, forming a wound site, and exposing the wound site to a suspension of *R. rhizogenes*. Contacting a plant colonized by a fastidious plant microbe with a suspension of *R. rhizogenes*, in some embodiments, may include removing a photosynthetic portion of the plant to generate a wound site. In some embodiments, a method may include covering a wound site with a rock wool matrix and exposing the rock wool matrix to a suspension of *R. rhizogenes*. According to some embodiments, a method may include submerging a wound site in a suspension of *R. rhizogenes*, vacuum infiltrating at least a portion of the suspension of *R. rhizogenes* into the wound site, and covering the wounds site with a vermiculite matrix. A method may comprise, in some embodiments, contacting any desired portion of a plant colonized with the fastidious plant microbe with *R. rhizogenes* including, for example, a cotyledon, a hypocotyl, an immature shoot, an immature root, a mature shoot, or mature root.

Propagating a colonized hairy root, according to some embodiments, may include exposing an attached hairy root or a harvested hairy root to one or more selective conditions. In some embodiments, propagating may include transferring an attached hairy root or a harvested hairy root to at least one of: a vermiculite matrix, a hydroponic system, an in vitro system, and a bioreactor system. A method may comprise assessing the presence of the fastidious plant pathogen in the propagated microbial hairy roots, according to some embodiments.

The present disclosure relates, in some embodiments, to methods for assessing an effect of a test composition on a fastidious plant microbe. A method may comprise, for example, contacting a plant (e.g., a tomato plant, a potato plant, a citrus plant) infected with the fastidious plant microbe (e.g., *Xylella fastidiosa*, *Candidatus* Liberibacter spp.) with *R. rhizogenes* under conditions that permit induction of hairy roots colonized by the fastidious plant microbe, propagating the colonized microbial hairy roots, contacting the propagated colonized microbial hairy roots with the test composition, and/or assessing at least one metric of the presence and/or vitality of the fastidious plant microbe. In some embodiments, a cultivated plant microbe may be *Candidatus* Liberibacter spp. (e.g., *Candidatus* Liberibacter solanacearum (Lso) and/or *Candidatus* Liberibacter asiaticus (Las)).

A method may comprise, in some embodiments, contacting *Rhizobium rhizogenes* with any desired portion of a plant colonized with a fastidious plant microbe including, for example, a cotyledon, a hypocotyl, an immature shoot, an immature root, a mature shoot, or mature root. In some embodiments, a test composition may be applied to and/or injected into an infected microbial hairy root. A test composition, in some embodiments, may be conditionally or constitutively present in an infected plant (e.g., a propagated infected hairy root).

According to some embodiments, a colonized plant (e.g., a propagated colonized hairy root) may comprise an exogenous transgene (e.g., NPR1, GFP) and the test composition may be or may comprise a gene product of the transgene. In some embodiments, a colonized plant (e.g., a propagated colonized microbial hairy root) may include at least one of an exogenous transgene, a CRISPR/Cas, a TALEN, and an RNAi construct, and accordingly a test composition may be or may comprise a gene product of the transgene, a CRISPR/Cas, a TALEN, and an RNAi construct. In some embodiment, a test composition may include an NPR1 protein.

The present disclosure relates, in some embodiments, to methods for culturing fastidious plant microbes using hairy roots. A method may comprise, for example, selecting tissues from one or more parts of a plant as an explant source; cultivating the explant source in an in vitro medium comprising *Rhizobium rhizogenes* (*R. rhizogenes*); cutting the explant source into a plurality of pieces; inducing growth of hairy roots from at least some pieces of the explant source over a period of time; performing polymerase chain reaction (PCR) amplification of *R. rhizogenes* root locus B (rolB) and *R. rhizogenes* root locus C (rolC) marker genes to confirm the induction of the hairy roots; and/or performing PCR amplification of a 16S rDNA marker genes to determine presence of one or more fastidious microbes. In some embodiments, an infected plant may comprise a first exogenous transgene and a second exogenous transgene. A first exogenous transgene may encode, for example, an autofluorescent protein (e.g., green fluorescent protein, yellow fluorescent protein, red fluorescent protein, and the like). According to some embodiments, cultivating the explant source in a medium comprising *R. rhizogenes* may comprise cultivating the explant source in a medium free of antibiotics (e.g., free of at least cefatoxime, carbencillin and kanamycin).

BRIEF DESCRIPTION OF THE DRAWINGS

The file of this disclosure contains at least one drawing executed in color. Copies of this patent with color drawing (s) will be provided by the Patent and Trademark Office upon request and payment of the necessary fee. Some embodiments of the disclosure may be understood by referring, in part, to the present disclosure and the accompanying drawings.

FIG. 3A shows cutting of surface-sterilized plant tissues into smaller pieces and gentle wounding using a fine forceps, according to an embodiment of the disclosure.

FIG. 3B shows immersing explants in a suspension of *R. rhizogenes*, according to an embodiment of the disclosure.

FIG. 3C shows explants following three-day co-cultivation of the plant tissues on nutrient media, according to an embodiment of the disclosure.

FIG. 3D shows an osmotic stress treatment of explants, according to an example embodiment of the disclosure.

FIG. 3E shows incubation of the explants in nutrient selection media following the treatment of FIG. 3D, according to an embodiment of the disclosure.

FIG. 21A shows hairy root production using CLso- and CLas-infected tomato explants.

FIG. 21B shows hairy root production using CLso- and CLas-infected potato explants.

FIG. 21C shows hairy root production using CLso- and CLas-infected citrus (lemon, orange and grapefruit) explants.

FIG. 21D provide confirmation of GFP-expressing hairy roots vs. adventitious roots by fluorescence microscopy (in potato cultures).

FIG. 21E provide confirmation of GFP-expressing hairy roots vs. adventitious roots by fluorescence microscopy (in citrus cultures).

FIG. 21F provides results of tests to detect CLso in the hairy root cultures, which was performed by PCR amplification of diagnostic markers specific to CLso (16S rDNA) (Levy et al., 2011) and CLas (rplk04/J5) (Hocquellet et al, 1999). GFP rolB and rolC, encoded on the Ti- and Ri-plasmids, co-transformed into the hairy roots, were used as markers for hairy roots; RPL and GAPC2 are endogenous *Solanacea* and citrus genes used as housekeeping gene control for PCR. "L" "HR" and "M" indicate leaf, hairy root sample, and DNA ladder, respectively. "+" indicates a positive control used for the respective PCR amplifications.

FIG. 21G provides results of tests to detect CLas in the hairy root cultures, which was performed by PCR amplification of diagnostic markers specific to CLso (16S rDNA) (Levy et al., 2011) and CLas (rplk04/J5) (Hocquellet et al, 1999). GFP rolB and rolC, encoded on the Ti- and Ri-plasmids, co-transformed into the hairy roots, were used as markers for hairy roots; RPL and GAPC2 are endogenous *Solanacea* and citrus genes used as housekeeping gene control for PCR. "L" "HR" and "M" indicate leaf, hairy root sample, and DNA ladder, respectively. "+" indicates a positive control used for the respective PCR amplifications.

FIG. 21A provides a typical transgene overexpression construct. GFP is included to serve as a visual marker for integration of the construct in the hairy roots.

FIG. 22B provides representative images of healthy and CLso-potato hairy root cultures at 30 days post-transformation with control (GFP alone) or with putative disease resistance genes from *Arabidopsis* (AtNPR1) and tomato (SINPR1).

FIG. 22C provides visualization of the hairy root cultures under a fluorescence microscope to confirm GFP and NPR1 expression in the hairy roots.

FIG. 22D provides RT-PCR results to confirm GFP and NPR1 expression in the hairy roots. Primer-dimers and non-specific amplicons of putative NPR1 orthologs in potato are indicated by asterisks (*).

FIG. 22E shows quantification of relative CLso-titers in transformed hairy roots at 30-days post transformation demonstrated suppression of CLso in AtNPR1 and S1NPR1 expressing hairy roots, when compared to the GFP alone control in two independent experiments.

FIG. 23A shows the CRISPR-Cas9 gene editing construct to edit potato NPR3 (StNPR3). A GFP gene is added to the construct to serve as a visual marker for delivery of the construct in the hairy root cultures.

FIG. 23B shows photographs of hairy root cultures and gransformation of Cas9 alone (control) and Cas9-sgNPR3 targeting potato NPR3 gene in healthy and *Candidatus* Liberibacter solanacearum (CLso) hairy root cultures.

FIG. 23C shows the quantification of CLso levels in edited hairy roots, which shows reduction in CLso titers in Cas9-sgNPR3 hairy roots, but not in Cas9 alone, suggesting that editing of the susceptibility gene (StNPR3) can confer tolerance to CLso.

FIG. 23D provides indel sequence analysis. Amplicon sequencing confirmed gene editing in the target DNA (StNPR3), as indicated by presence of indels in the Cas9-sgNPR3 hairy root cultures, but not in Cas9 alone cultures. FIG. 23D discloses SEQ ID NOS: 43, 23-30, respectively, in order of appearance.

FIG. 24A show pictures of healthy and CLso hairy root cultures that were generated and prepared for in vitro bioassays.

FIG. 24B show pictures of healthy and CLso hairy root cultures that were generated and prepared for in vitro bioassays.

FIG. 24C show the quantification of relative CLso-titers after 48 h treatment with bactericides (penicillin and oxytetracycline, 100 ppm) and immune modulators (salicylic acid [100 uM] and methyl jasmonate [10 uM]), along with untreated control (DMSO). Penicillin, oxytetetracycline, methyl-jasmonate decreased CLso titers, while salicylic acid did not.

FIGS. 26A-G provide proof-of-concept of GFP gene editing in microbial hairy root cultures.

FIG. 26A shows a typical CRISPR-Cas9 gene editing construct. FIG. 26A discloses SEQ ID NO: 31.

FIG. 26B shows transformation of Cas9 alone (control) and Cas9-sgGFP targeting GFP gene in healthy and *Candidatus* Liberibacter solanacearum (CLso) hairy root cultures.

FIG. 26C (healthy hairy root cultures) shows the loss of GFP fluorescence in Cas9-sgGFP, but not in Cas9 alone, indicates successful editing of the GFP gene.

FIG. 26D (CLso hairy root cultures) shows the loss of GFP fluorescence in Cas9-sgGFP, but not in Cas9 alone, indicates successful editing of the GFP gene.

FIG. 26E shows indel sequence analysis of healthy cultures. Amplicon sequencing confirmed gene editing in the target DNA (GFP), as indicated by presence of indels in the Cas9-sgGFP hairy root cultures, but not in Cas9 alone cultures. FIG. 26E discloses SEQ ID NOS: 32-38, respectively, in order of appearance.

FIG. 26F shows indel sequence analysis of CLso infected hairy root cultures. Amplicon sequencing confirmed gene editing in the target DNA (GFP), as indicated by presence of indels in the Cas9-sgGFP hairy root cultures, but not in Cas9 alone cultures.

Figure 26:
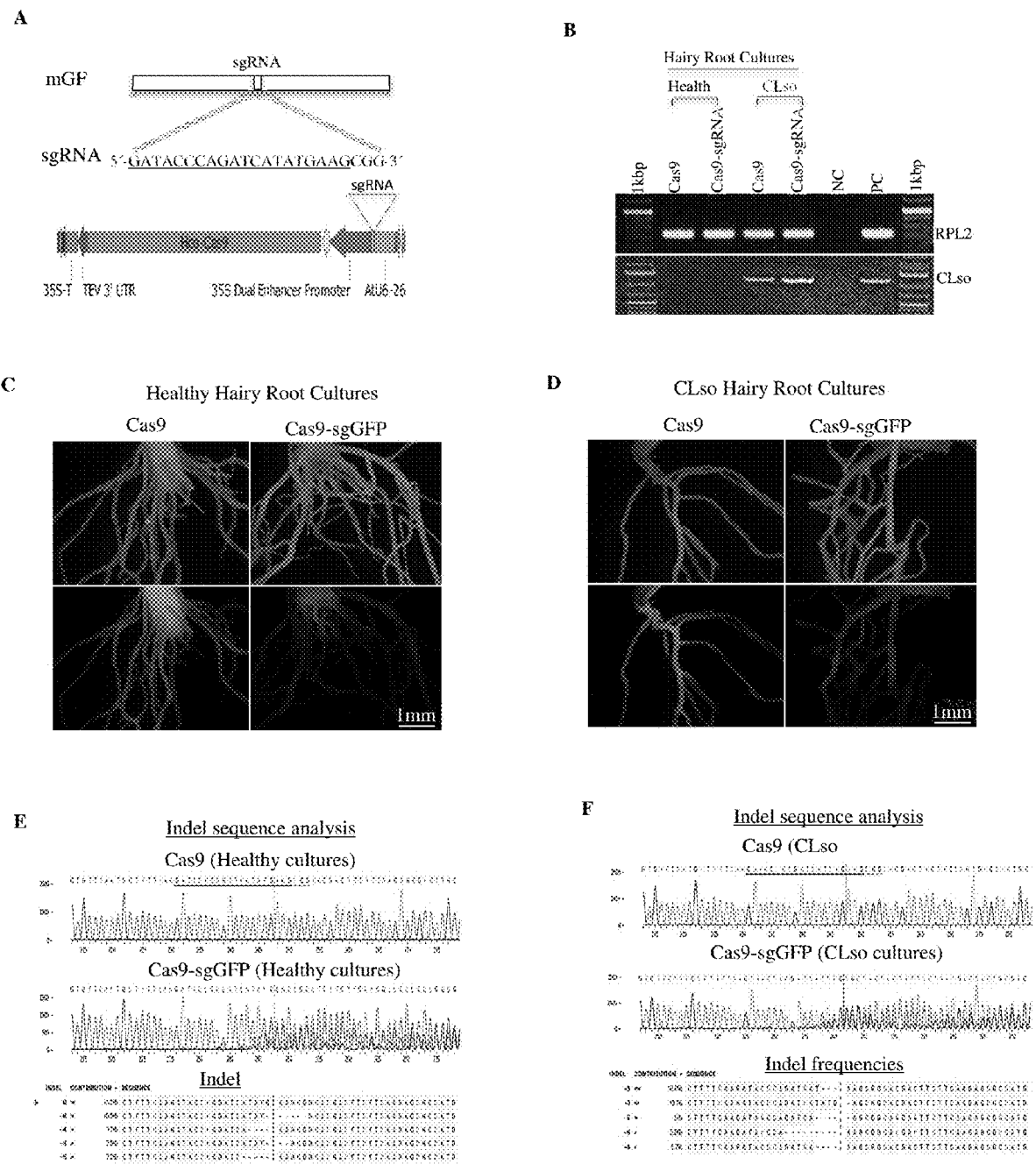

FIG. 26F discloses SEQ ID NOS: 32, 39-41, 38, 42, and 36, respectively, in order of appearance.

Figure 27:
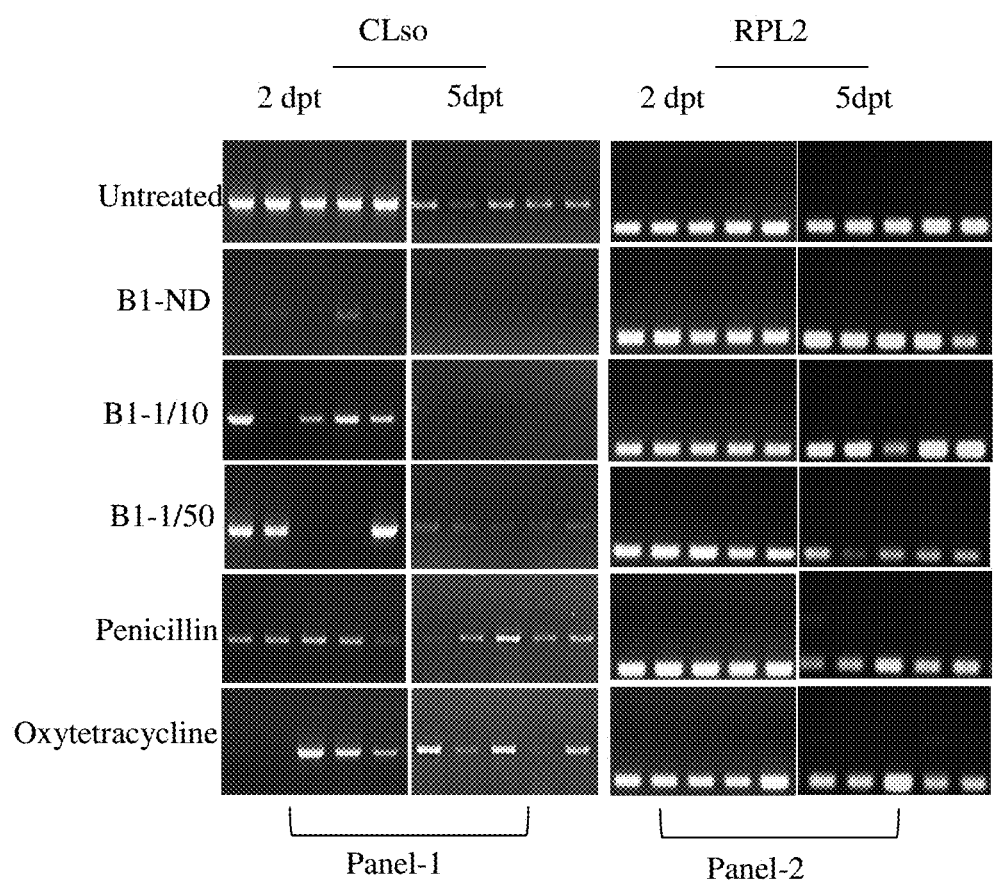

FIG. 27 provides results for efficacy testing of a biological in microbial hairy root cultures. Detection of *Candidatus* Liberibacter solanacearum (CLso) by conventional PCR in DNA extracted from CLso-potato hairy root cultures treated with a biological (B1) for 2 and 5 days. Panel 1 and 2 represent levels of CLso (16S rDNA), and a house keeping gene (RPL2) of potato used as a control for DNA integrity. Five biological replicates are included for each treatment. Abbreviations: B1-ND=CLso hairy roots treated with biological without dilution, B1-1/10=1:10 dilution of biological, B1-1/50-CLso=1:50 dilution of biological. Penicillin and oxytetracycline were used as reference bactericides.

DETAILED DESCRIPTION

Despite the huge economic significance of fastidious microbes (e.g., plant microbes), little is known of their biology, genetics, and the vector-pathogen-plant interactions. This knowledge may enable development of effective disease and pest management strategies to limit yield losses (e.g., tremendous losses). One bottleneck (e.g., a major bottleneck) in characterizing these fastidious microbes is their inability to grow outside their natural hosts, as they are obligate parasites of plants. It is estimated that >99% of microorganisms from any environment are non-cultivable in the laboratory. Numerous attempts have been made to create suitable artificial growth media and culture conditions for cultivating fastidious microbes; however, to date these approaches have had only limited success.

Plant hairy roots can be readily induced from diverse plant tissues upon infection by a soil bacterium, *Rhizobium rhizogenes* (recently revised from *Agrobacterium rhizogenes*). In a manner similar to its related cousin, *A. tumefaciens, R. rhizogenes* introduces its root-inducing (Ri) transfer-DNA (Ri-DNA plasmid), which encodes the root locus (rol) genes (e.g., rolB, rolC) into the plant genome. The expression of rol genes in planta overproduces the plant hormone, auxin, and induces hairy root initiation and proliferation.

Hairy roots are anatomically, morphologically, and metabolically similar to normal roots. Hairy roots are connected to a plant tissue from which they are generated by Intact xylem and phloem vasculature, thereby allowing continued transport of water, nutrients, cellular signaling—and as shown here fastidious microbes-through the vasculature. Typically hairy roots are smaller in diameter than a plant tissue from which they derive (e.g., stem, root) and are often numerous. A large number of plant genuses may be transformed by *R. rhizogenes* and generate hairy roots, including but not limited to: *Citrus* (e.g., lemon), Solanaceae (e.g., potato, tomato), *Daucus* (e.g., carrot), *Taxus, Cinchona, Gmelina, Glycine* (e.g., soybean), *Rutaceae* (e.g., Bael tree), Nyctaginaceae, and *Rosaceae* (e.g., apple).

The present disclosure relates, in some embodiments, to a method of cultivating a fastidious microbe (e.g., in vitro, in planta). The present disclosure relates, in some embodiments, to a hairy root system that may be directly used to cultivate and characterize fastidious microbes. The present disclosure relates, in some embodiments, to a hairy root system that may be used for high-throughput functional genetic and genomic studies of the fastidious microbe-plant interactions. In some embodiments, a hairy root system may be used for chemical genetic screens (e.g., screening antibiotics, essential oils, oxylipins) to combat devastating plant diseases. According to some embodiments, a hairy root system may include a genetically modified plant and may be beneficial in identifying gene related susceptibility and/or resistance to fastidious microbes in plant species.

According to some embodiments, *Rhizobium rhizogenes*-mediated hairy root cultures of a host plant (e.g., tomato, potato, pepper, citrus) may be infected with a fastidious microbe (e.g., *Candidatus* spp., *Xylella* spp., *Clavibacter* spp.). In other words in any of the embodiments discussed herein, hairy roots can first be developed from a healthy plant and then the hair roots are infected or alternatively, hairy roots can be developed from an explant from an infected plant. So for example, a hairy root culture of a healthy plant is created and then it is exposed to a fastidious microbe. A tissue from one or more parts of a plant as an explant source is selected to make an explant. Then one contacts the explant with a suspension of *Rhizobium rhizogenes* under conditions that permit induction of hairy roots to form a hairy root on the explant. Then one propagates the hairy root to form a propagated hairy root; and finally contact the propagated hairy root with a fastidious plant microbe to form a fastidious plant colonized hairy root.

Explant source material may include any desired organ or tissue of a plant including, for example, cotyledons, hypocotyls, immature and mature shoots and roots. An optimal source may be identified for a particular set of conditions by testing multiple infected plant tissues. Hairy root multiplication techniques (e.g., techniques for scalability and/or multiplexing) may be included for high-throughput diagnostics and/or molecular characterization, according to some embodiments. Functional characterization for a hairy-root system may include, in some embodiments, genetic gain-of-function (e.g., overexpression) and loss-of-function (e.g., clustered, regularly interspaced, short palindromic repeat-associated (CRISPR/Cas), Transcription activator-like effector nuclease (TALEN) and Ribonucleic Acid inference (RNAi) knockdown) studies of candidate plant and pathogen-encoded genes. Gene constructs (e.g., representative gene constructs) or gene libraries may be transiently delivered into established hairy-roots by any desired method including, for example, vacuum infiltration and/or by DNA bombardment. In some embodiments, gene constructs may be inserted into the *R. rhizogenes* T-DNA prior to hairy-root induction, thus completing the process in a single step.

According to some embodiments, a hairy root system may be used for propagation and functional studies of any desired plant-microbe association (e.g., beyond vascular-colonizing phytobacteria) including viruses (e.g., Tomato spotted wilt virus, Tomato bushy stunt virus, Alfalfa mosaic virus, Cucumber mosaic virus, Cauliflower mosaic virus, Turnip yellow mosaic virus), viroids (e.g., Potato spindle tuber viroid, Tomato apical stunt viroid, *Citrus* exocortis viroid), and endophytic microbes (e.g., *Acidovorax facilis, Azoarcus* sp. BH72, *Azospirillum* sp. B510, *Fusarium* spp., *Colletotrichum* spp, *Curvularia* spp., *Beauveria bassiana, Lecanicillium* spp, *Pythium oligandrum*).

Previous studies have not reported the application of hairy roots to culture or to the study of fastidious plant microbes. Thus, the present disclosure showing that hairy roots can support the growth of fastidious microbes may have a significant impact on large-scale propagation of microbial hairy roots for high-throughput applications. The disclosed hairy root system resolves a significant bottleneck in culturing and propagating fastidious phytopathogens and may result in the initiation of numerous biological studies of fastidious plant microbes. Such studies offer the promise of new transformative developments in plant disease and pest management, as well as, agriculture in general.

The present disclosure, in some embodiments, may help establish and optimize *Candidatus* Liberibacter spp. microbial hairy root cultures in any suitable plant such as potato, tomato and citrus, and allow researchers to perform genetic and/or chemical analysis using the disclosed microbial hairy root system.

According to some embodiments disclosed here, hairy roots induced directly from infected plants may provide an easy, rapid, and scalable platform to culture and characterize fastidious vascular-colonizing plant microbes. For example, Lso and Las are prevalent in South Texas and infect several Solanaceous crops including potato, tomato, and *Citrus* spp. Thus, Las-infected citrus trees in South Texas may be used to obtain Las-infected plant material. Plant tissues from Las-infected citrus trees may be collected and tested for Las presence by polymerase chain reaction (PCR) amplification of 16S rDNA, an established DNA marker for detecting Las. Las-positive citrus tissues may be further used as an explant source for microbial hairy root induction.

The present disclosure relates, in some embodiments, to a biological mimic hairy root platform for rapid culture, propagation, and functional studies of fastidious vascular-colonizing microbes (e.g., plant pathogens). Fastidious vascular-colonizing plant microbes such as *Candidatus* spp., *Xylella* spp., viruses, phytoplasmas and spiroplasmas result in billions of dollars of annual crop losses. The inability to culture these and other vascular-limited microbes (e.g., pathogens) presents a tremendous challenge to researchers attempting to study these organisms. Plant hairy roots induced by *Rhizobium rhizogenes* are organized, stable tissues anatomically and metabolically similar to roots, and they possess intact xylem and phloem vasculature. According to some embodiments, microbe-containing hairy roots induced directly from infected plants may provide an easy, rapid, and scalable platform to culture, propagate, and characterize fastidious vascular-limited plant microbes (e.g., in the laboratory).

According to some embodiments, *Candidatus* Liberibacter spp. microbial hairy root cultures in a plant (e.g., potato, tomato, citrus) may enable genetic analysis using a microbial hairy root system. In addition to alleviating previous challenges of culturing fastidious vascular-limited plant microbes, a hairy root platform may be readily exploited for transformative, high-throughput functional studies including but not limited to genetic and chemical screens for novel antimicrobials and bactericides. Because *R. rhizogenes* may effectively induce hairy roots in diverse monocot and dicot plants, microbial hairy root systems, methods, and compositions for microbial cultivation may be applied to other agronomic crops and plant microbe associations beyond vascular-colonizing phytobacteria such as fungi, viruses, viroids, and endophytic microbes.

Generating an Explant and/or Inoculum Source

Insect vectors may spread fastidious microbes from plant to plant. Plant material colonized by a fastidious microbe (e.g., explant) may be generated, according to some embodiments, by allowing or introducing an insect vector carrying the fastidious microbe to feed upon a plant and thereby transferring the fastidious microbe to the plant tissue. Once transferred into a plant vascular system, a fastidious microbe can colonize and replicate.

According to some embodiments, a fastidious microbe carrying insect vectors may be collected from an environment (e.g., agricultural fields) and tested to determine whether they carry the fastidious microbe (e.g., 16S rDNA PCR). Insect vectors (e.g., fastidious microbe carrying insect vectors, non-carrying insect vectors) may be maintained (e.g., in insect cages) and propagated, in some embodiments. A fastidious microbe carrying insect vector, in some embodiments, may be generated in a laboratory setting, for example, by allowing a non-carrying insect vector to feed upon plant tissue infected by a fastidious microbe. Numerous methods are known for transmitting a fastidious microbe to an insect vector, as well as, maintaining and propagating an insect vector population, all of which are within the scope of the present disclosure.

In some embodiments, an insect vector population may be tested for the presence or absence of colonization by a fastidious microbe. Any suitable technique may be used to test an insect vector for the presence or absence of colonization by a fastidious microbe, for example 16S rDNA PCR. At least one fastidious microbe carrying insect vector may be permitted to feed upon an uninfected plant for a period of time (e.g., seven days); thereby transferring at least one fastidious microbe to the plant vasculature. Within the scope of this disclosure, numerous methods may be used to successfully transfer at least one fastidious microbe to a plant vasculature. Such methods may vary depending upon at least: the species and developmental stage of an insect vector, a level of fastidious microbe within an insect vector, a rate at which a fastidious microbe replicates within an insect vector, and a species and developmental stage of an uninfected plant. According to some embodiments, after a designated feeding period (e.g., seven days), a microbe carrying insect vector may be removed from the plant and the plant may be monitored for colonization and/or disease development. In some embodiments, disease symptoms may indicate colonization by a fastidious microbe. Any number of standard laboratory procedures may be used to identify the presence or absence of a fastidious microbe within a plant tissue. According to some embodiments, plant tissue may be tested for the presence or absence of fastidious microbe populations using 16S rDNA PCR. A plant or plant tissue (e.g., cotyledon) which tests positive for the presence of a fastidious microbe (e.g., PCR positive) may be used as a source of explant for microbial hairy root induction, according to some embodiments. According to some embodiments, a method for cultivating a fastidious plant microbe may include colonizing a plant with a fastidious microbe to generate an explant source. In some embodiments, colonizing a plant with a fastidious microbe may include exposing one or more surfaces of the plant to at least one fastidious microbe carrying insect vector (e.g., an Lso carrying psyllid). An explant, in some embodiments, may include a plant tissue, such as a cotyledon, a hypocotyl, an immature shoot, an immature root, a mature shoot, a mature root, or any combination thereof.

A Microbial Hairy Root Platform

FIG. 1 illustrates a microbial hairy root platform workflow 100 including: propagating a fastidious microbe in one or more plant tissues 102; inducing microbial hairy root production from infected plant tissues 110; propagating microbial hairy roots 120, and applying microbial hairy roots to downstream studies and applications 130, according to example embodiments of the present disclosure.

As shown in FIG. 1, according to some embodiments, a fastidious microbe may be propagated in one or more plant tissues 102. One or more plant tissues of an infected plant may be colonized by a fastidious microbe including a cotyledon 104, a hypocotyl 106, a leaf 108, an immature shoot, an immature root, a mature shoot, a mature root, or any combination thereof. Propagating a fastidious microbe (e.g., Lso, Las) in one or more plant tissues may include exposing a healthy plant to one or more vector species (e.g., psyllid) that are colonized by the fastidious microbe and that are known to feed on plant tissues, according to some embodiments. According to some embodiments, propagating a fastidious microbe may include various methods of asexual plant propagation. According to some embodiments, propagating a fastidious microbe may include identifying infected plants from an environment and maintaining the identified plants.

A microbial hairy root platform workflow 100, may include inducing microbial hairy root generation from an infected plant or plant tissue 110. According to some embodiments, inducing microbial hairy root generation may include culturing *Rhizobium rhizogenes*. Numerous methods are appropriate for culturing *R. rhizogenes* and are encompassed by this disclosure. Culturing *R. rhizogenes* may include growing *R. rhizogenes* in any appropriate culture medium (e.g., Luria-Bertani medium (LB)) to any appropriate optical density (e.g., 0.3). In some embodiments, a culture of *R. rhizogenes* may be grown to an O.D. of about 0.2, or about 0.3, or about 0.4, or about 0.5, or about 0.6. According to some embodiments, a culture of *R. rhizogenes* may be grown to an O.D. between 0.2 and 0.6, or between 0.3 and 0.6, or between 0.2 and 0.4. Upon reaching an elected optical density, a culture of *R. rhizogenes* may be removed from a medium (e.g., via centrifugation) and resuspended in a volume of plant culture medium (e.g., ½ MS or ½ B5+3% sucrose) or water (e.g., sterile water) to a desired concentration. In some embodiments, a culture of *R. rhizogenes* may be resuspended at an O.D. of about 0.2, or about 0.3, or about 0.4, or about 0.5, or about 0.6. According to some embodiments, a culture of *R. rhizogenes* may be resuspended at an O.D. between 0.2 and 0.6, or between 0.3 and 0.6, or between 0.2 and 0.4.

According to some embodiments, a strain of *R. rhizogenes* may be selected based on specific characteristics. For example, different *R. rhizogenes* strains may have varying potentials to induce hairy roots from plants. A suitable strain for propagating microbial hairy roots in a plant or explant (e.g., tomato, potato, citrus) may be empirically determined, in some embodiments, based on, for example, a percent induction of hairy roots in a selected explant tissue type and/or plant species (e.g., tomato, potato, citrus). Suitable strains of *R. rhizogenes* for evaluation and/or use may include, in some embodiments, American Type Cell Culture (ATCC) 15834, ATCC 43056, ATCC 43057, ATCC 13333, K599, or any combination thereof. According to some embodiments, for each combination of explant tissue and *R. rhizogenes* strain, induction efficiency may be determined by measuring parameters such as the following: (a) hairy root induction percentage per total explants; (b) hairy root initiation days per total explants; (c) hairy root induction frequency per single explant, and (d) fastidious microbe (e.g., Las and Lso) populations in the hairy roots. For accurate comparison of microbial titers amongst different samples (e.g., explant tissue type, plant species type), quantitative PCR techniques (e.g., q-PCR, quantitative Real-Time PCR) may be used, according to some embodiments. Statistical analysis, such as an analysis of variance (ANOVA) and Student's T-test, may be employed to determine significant differences between populations amongst different samples.

Figure 1:
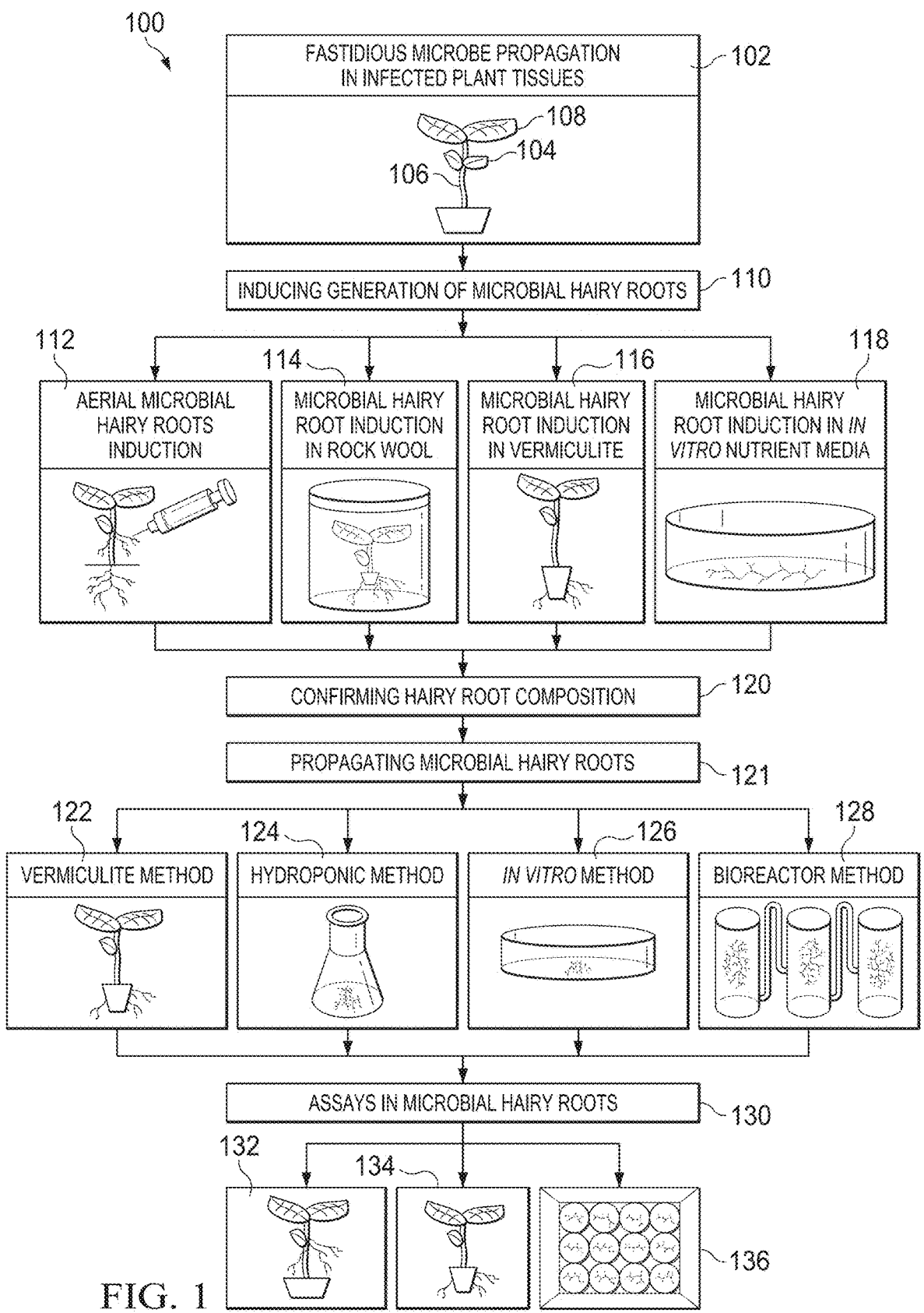
FIG. 1 illustrates a workflow for generating microbial hairy roots for downstream studies and applications, according to example embodiments of the disclosure.

As illustrated in FIG. 1, both in planta 110, 112, 114 and in vitro 116 approaches may be used to induce microbial hairy root generation directly from one or more infected plant tissues. In planta approaches for inducing microbial hairy root generation include aerial induction of microbial hairy roots 110, rock wool induction of microbial hairy roots 112, and vermiculite induction of microbial hairy roots 114.

In Planta Methods of Inducing Microbial Hairy Roots

Inducing microbial hairy roots 110, in some embodiments, may include selecting an infected plant (e.g., Lso) and preparing one or more surfaces of the infected plant (e.g., surface sterilization, wounding). Preparing an infected plant may include surface sterilization of one or more surfaces of the infected plant. Any appropriate surface sterilization techniques may be used including, in some embodiments, exposure of one or more surfaces of an infected plant for a designated period of time (e.g., 1 to 10 minutes) to a solution containing an alcohol (e.g., 70% ethanol), NaClO (bleach) (e.g., 2%, 10%), a non-phytotoxic anti-fungal (e.g., amphotericin B), an anti-bacterial (e.g., 200 mg/L cefotaxime or 100 mg/L carbenicillin) compound, or any combination thereof.

According to some embodiments, preparing an infected plant (e.g., colonized by Lso or Las) may include wounding one or more surfaces of the infected plant. Any suitable tools may be used to wound one or more surfaces of an infected plant, including scissors, a scalpel, forceps (e.g., fine gauge), a syringe, a needle, or any combination thereof. Wounded and exposed surfaces of an infected plant may serve as active sites for *R. rhizogenes* transformation and hairy root induction, in some embodiments.

In some embodiments, inducing microbial hairy roots 110 may include contacting an infected plant or a portion of an infected plant with at least one *R. rhizogenes* cell (in planta approach), as shown in FIG. 1 at 112, 114, and 116. Contacting an infected plant with at least one *R. rhizogenes* cell may include directly exposing one or more parts (e.g., a wound site) of an infected plant to a *R. rhizogenes* suspension (e.g., O.D. 0.3) (e.g., to generate aerial hairy roots) or vacuum infiltrating one or more parts of an infected plant with a *R. rhizogenes* suspension, according to some embodiments.

According to some embodiments, one or more portions of an infected plant may be directly contacted by a suspension containing at least one cell of *R. rhizogenes* (e.g., O.D. 0.3). Various methods may be used to contact one or more portion of an infected plant with a suspension containing at least one cell of *R. rhizogenes*. According to some embodiments, contacting one or more portions of an infected plant may include: applying a suspension containing at least one cell of *R. rhizogenes* to a wound site (e.g., using a dropper), dipping a fine needle in a suspension of *R. rhizogenes* and using the fine needle to wound one or more locations on an infected plant; injecting a suspension of *R. rhizogenes* into an infected plant using a syringe. As shown in FIG. 1 112, contacting an infected plant at a location above soil level may generate one or more aerial microbial hairy roots.

According to some embodiments, contacting one or more portions of an infected plant with at least one cell of *R. rhizogenes* (e.g., an exposed wound site) may include wrapping or covering (e.g., with aluminum foil) a contact site. Wrapping or covering a contact site may reduce exposure to light and/or maintain desired humidity levels, in some embodiments.

In some embodiments, contacting one or more portions of an infected plant with at least one cell of *R. rhizogenes* may include infiltrating the one or more portions of the infected plant using vacuum pressure. As shown in FIG. 1 at 116, inducing microbial hairy roots may include removing a portion of an infected plant (e.g., a shoot) to form a wound site and contacting the wound site with a solution containing at least one cell of *R. rhizogenes* (e.g., O.D. 0.3). In some embodiments, contacting a portion of an infected plant with a solution containing at least one cell of *R. rhizogenes* (e.g., O.D. 0.3) may include submerging a wound site in the solution and exposing the portion of the infected plant to a vacuum environment for a period of time. Any vacuum environment that permits infiltration of at least one plant cell with at least one cell of *R. rhizogenes* may be used. In some embodiments, a vacuum environment may be about 20 inHg, or about 25 inHg, or about 30 inHg. According to some embodiments, a period of time for which a vacuum environment may any suitable length of time that permits infiltration of at least one plant cell with at least one cell of *R. rhizogenes*. A period of time for which a vacuum may be held may be any length of time. For example, in some embodiments, a vacuum may be held for at least about 30 sec, or at least about 1 min, or at least about 5 min, or at least about 10 min, or at least about 30 min, or at least about 60 min, or at least about 3 hours, or at least about 6 hours, or at least about 12 hours.

According to some embodiments, and as shown at 114 of FIG. 1, following vacuum infiltration a wound site may be removed from a solution of *R. rhizogenes* and covered by (e.g., completely covered, partially covered) inserting in a vermiculite matrix. In some embodiments, inducing microbial hairy roots may include removing a portion of an infected plant (e.g., a shoot) to form a wound site, contacting the wound site with a solution containing at least one cell of *R. rhizogenes* (e.g., O.D. 0.3), removing the wound site from the solution, and covering the wound site with a vermiculite matrix. In some embodiments, a portion of an infected plant covered by a vermiculite matrix may be maintained in conditions suitable for formation of one or more microbial hairy roots. A vermiculite matrix may be periodically changed, in some embodiments.

As shown in FIG. 1 at 114, inducing microbial hairy roots may include removing a portion of an infected plant (e.g., a shoot) to form a wound site, covering the wound site in a rock wool matrix, and exposing the rock wool matrix to a solution containing at least one cell of *R. rhizogenes*. Exposing a rock wool matrix to a solution containing at least one cell of *R. rhizogenes* (e.g., O.D. 0.3) may include providing a sufficient volume of the solution to partially saturate or fully saturate the rock wool matrix. According to some embodiments, a portion of an infected plant covered by a rock wool matrix may be maintained in conditions suitable for co-cultivation of the *R. rhizogenes* with one or more plant cells for a co-cultivation period. According to some embodiments, a co-cultivation period may be at least about 12 hours, or at least about 24 hours, or at least about 48 hours, or at least about 72 hours. Following a co-cultivation period, in some embodiments, a rock wool matrix may be dried (e.g., air dried, vacuum dried) to form a dried rock wool matrix. A dried rock wool matrix may retain some moisture, according to some embodiments. In some embodiments, a dry rock wool matrix may have a reduced population of *R. rhizogenes* when compared to the same rock wool matrix prior to drying. According to some embodiments, drying a rock wool matrix may be performed by exposing the rock wool matrix to one or more drying conditions (e.g., temperatures, air currents) for a period of at least 6 hours, or at least 12 hours, or at least 24 hours, or at least 36 hours, or at least 48 hours, or at least 72 hours. In some embodiments, a dried rock wool matrix may be rehydrated.

Contacting one or more portions of an infected plant (e.g., 112, 114, 116) with at least one cell of *R. rhizogenes* may include maintaining a contacted plant in conditions appropriate for formation of microbial hairy roots (e.g., incubator, growth chamber, greenhouse) until at least one hairy root generates. Conditions appropriate for generation of one or more microbial hairy roots may vary depending upon factors including: a species of infected plant, a portion of an infected root contacted, a method of contacting an infected plant, a strain of *R. rhizogenes* selected, a concentration of *R. rhizogenes* in a contact solution, or any combination thereof. According to some embodiments, an infected plant may be maintained at a temperature of between about 21° C. and about 25° C. In some embodiments, an infected plant may be maintained in conditions having a light/dark cycle of about 8 hours of light to about 16 hours of light per 24 hour period, according to some embodiments. In some embodiments microbial hairy roots may appear about 10 to 21 days after contacting an infected plant with a suspension of *R. rhizogenes*.

In Vitro Methods of Inducing Microbial Hairy Roots

As illustrated in FIG. 1 at 118, inducing microbial hairy roots may be performed in vitro, according to some embodiments of the present disclosure. In vitro induction of microbial hairy roots, according to some embodiments, may include: preparing a culture of *R. rhizogenes*, preparing an explant, contacting (e.g., co-cultivation) the explant with a solution containing at least one *R. rhizogenes* cell, and exposing the explant to one or more selective conditions.

According to some embodiments, in vitro methods 118 of inducing microbial hairy roots 110 may include selecting one or more infected tissues (e.g., leaf, cotyledon, hypocotyl, and/or root) from a plant colonized by a fastidious microbe to serve as an explant. In some embodiments, inducing microbial hairy roots may include preparing an explant (e.g., surface sterilization, wounding). Preparing an explant may include surface sterilization of one or more surfaces of the explant (e.g., a cotyledon). Any appropriate surface sterilization techniques may be used including, in some embodiments, exposure of one or more surfaces of an infected plant or an explant to a solution containing an alcohol (e.g., 70% ethanol), NaClO (bleach) (e.g., 2.5%, 10% solution), a non-phytotoxic anti-fungal (e.g., amphotericin B), an anti-bacterial (e.g., cefotaxime or carbenicillin) compound, or any combination thereof for a designated period of time (e.g., 1 to 10 minutes).

In some embodiments, preparing an explant (e.g., a cotyledon) may include cutting an explant into smaller pieces (e.g., about 2 centimeter (cm) long)), wounding at least one portion of an explant (e.g., using forceps), or any combination thereof. Any suitable tools may be used to prepare an explant, including scissors, a scalpel, forceps (e.g., fine gauge), a syringe, a needle, or any combination thereof. Wounded and exposed surfaces of an explant (e.g., a cotyledon) may serve as active sites for *R. rhizogenes* transformation and hairy root induction.

In some embodiments, inducing microbial hairy roots may include contacting (e.g., co-cultivating) an explant (e.g., a surface sterilized and wounded cotyledon) with at least one *R. rhizogenes* cell (in vitro approach) 116. Contacting an explant (e.g., a prepared explant) with at least one cell of *R. rhizogenes* may include immersing the explant or prepared explant in a suspension containing at least one cell of *R. rhizogenes* (e.g., OD 0.3) for a period of time (e.g., 20 min), in some embodiments. An explant may be immersed in a suspension containing at least one cell of *R. rhizogenes* for any period of time, for example for at least 1 min, or for at least 5 min, or for at least 10 min, or for at least 15 min, or for at least 20 min, or for at least 25 min, or for at least 30 min, according to some embodiments. In some embodiments, co-cultivating an explant may include immersing an explant ( ) in a suspension containing at least one cell of *R. rhizogenes* (e.g., O.D. 0.3) for a period of about 1 min to about 30 min, or about 5 min to about 25 min, or about 10 min to about 25 min, or about 15 min to about 25 min, or about 15 min to about 20 min.

In some embodiments, contacting an explant with at least one cell of *R. rhizogenes* may include transferring an explant from a suspension containing at least one cell of *R. rhizogenes* (e.g., O.D. 0.3) to a co-cultivation medium (e.g., ½ MS or ½ B5+3% sucrose) and incubating the explant for a period of at least 12 hours, or at least 24 hours, or at least 36 hours, or at least 48 hours, or at least 72 hours. Incubating an explant or prepared explant may be performed under any suitable conditions for the survival of both the explant and the *R. rhizogenes*. In some embodiments, incubating an explant may be performed at a temperature of about 21° C., or about 22° C., or about 23° C., or about 24° C., or about 25° C. According to some embodiments, incubating an explant may be performed at a temperature of about 21° C. to about 25° C. A co-cultivation medium may include any medium that permits growth of *R. rhizogenes*, for example: a ½ MS or ½ B5+3% sucrose medium.

According to some embodiments, contacting an explant may include immersing the explant in a suspension containing at least one cell of *R. rhizogenes* for a period of 20 min, transferring the explant to a co-cultivation medium of ½ MS or ½ B5+3% sucrose, and incubating the explant at a temperature of 21° C. to 25° C. for a period of 72 hours.

In some embodiments, following contacting and incubation an explant may be exposed to one or more selective conditions. According to some embodiments, an explant or prepared explant may be transferred from a co-cultivation medium to selection medium. A selection medium may be any medium that inhibits (e.g., reduce a concentration or growth of) *R. rhizogenes*, untransformed tissue, untransformed roots, or any combination thereof. According to some embodiments, a selection medium may inhibit a population of *R. rhizogenes* but not inhibit a fastidious microbe (e.g., Lso). According to some embodiments, various measures may be used to avoid the potential pitfall of using common antibiotics (e.g., cefatoxime, carbencillin and kanamycin). For example, some antibiotics may inhibit a fastidious microbe residing inside an explant. Therefore, in some embodiments, alternative antibiotics, such as streptomycin (e.g., at 200 mg/L concentration), neomycin (e.g., at 100 mg/L), penicillin (e.g., at 100 mg/L) and hygromycin (e.g., at 100 mg/L), that are phloem-immobile and/or non-phytotoxic may be used. An explant may be transferred from a co-cultivation medium (e.g., about ½ MS or ½ B5+3% sucrose) to a selection medium (e.g., about ½ MS or ½ B5+3% sucrose+200 mg/L cefatoxime or 100 mg/L carbenicillin) which may inhibit (e.g., reduce a concentration or growth of) *R. rhizogenes*.

According to some embodiments, following contacting and incubation an explant may be exposed to osmotic stress. Exposing an explant to osmotic stress may be effective in inhibiting *R. rhizogenes* (e.g., reduce a concentration of). Various methods exist for exposing an explant to osmotic stress. For example, an explant may be exposed to osmotic stress by repeatedly rinsing the explant in sterilized de-ionized water for a period of time (e.g., about 30 minutes). In some embodiments, de-ionized water used for exposing an explant to osmotic stress may include an antibiotic compound, for example, 200 mg/L cefotaxime or 100 mg/L carbenicillin.

After contacting and exposing an explant to one or more selective conditions, an explant may be placed in an appropriate growing environment (e.g., incubator, growth chamber, greenhouse) until at least one hairy root generates. An explant may be subsequently monitored for hairy root induction. Depending on a plant species, an explant source, and a *R. rhizogenes* strain used, hairy roots may emerge within two to four weeks, according to some embodiments.

Microbial Hairy Root Induction Efficiency

In some embodiments, a hairy root induction efficiency may vary (e.g., significantly vary) based on various factors including: plant variety, strain of *R. rhizogenes*, and/or explant source (e.g., a cotyledon, a hypocotyl, an immature shoot, an immature root, a mature shoot, and a mature root). Empirical data may be used to optimize hairy root induction efficiencies. For accurate comparison of microbial populations amongst different samples (e.g., explant tissue type, plant species type), quantitative PCR techniques (e.g., q-PCR, quantitative Real-Time PCR) may be used, according to some embodiments. Statistical analysis, such as an analysis of variance (ANOVA) and Student's T-test, may be employed to determine significant differences between populations amongst different samples.

According to some embodiments, hairy root induction efficiencies may range from about 10% to about 90% depending on the plant variety, explant tissue, and *R. rhizogenes* strain used. The preferred explant tissue and *R. rhizogenes* strain may maximize microbial hairy root induction efficiency in various plants such as citrus, tomato, and potato.

Confirmation of a Hairy Root

As shown in FIG. 1 at 120, a microbial hairy root platform workflow 100, may include confirming that a microbial hairy root (e.g., generated in plant or in vitro) was induced by transformation by *R. rhizogenes*. Various molecular methods may be used in confirming that a microbial hairy root (e.g., generated in plant or in vitro) was induced by transformation by *R. rhizogenes*. For example, according to some embodiments, PCR amplification of known root inducing (Ri) DNA genes (e.g., rolB, rolC) may be conducted to confirm that a microbial hairy root (e.g., generated in planta or in vitro) was induced by transformation by *R. rhizogenes*.

Confirmation of Colonization of a Hairy Root by a Fastidious Microbe

A microbial hairy root platform workflow 100, may include confirming that a microbial hairy root generated from an infected plant is colonized by the fastidious microbe (e.g., Lso, Las), as shown in FIG. 1 at 120. Numerous scientific methods may be used to confirm that a microbial hairy root from an explant or an infected plant is colonized by a fastidious microbe without deviating from this disclosure, including but not limited to PCR, q-PCR, quantitative Real-Time PCR, reverse-transcription qPCR, enzyme-linked immunosorbent assay (ELISA), or any combination thereof.

Propagation of Microbial Hairy Roots Colonized by a Fastidious Microbe

According to some embodiments, a microbial hairy root platform workflow 100, may include propagating microbial hairy roots for downstream studies and applications. To successfully utilize microbial hairy roots for high-throughput biological studies, it may be desirable to propagate a microbial hairy root inoculum in sufficiently large quantities, according to some embodiments. Hairy roots systems are amenable to large-scale propagation. According to some embodiments, a harvested hairy root may be clonally propagated. Clonal propagation of a harvested hairy root may provide an increased source of a fastidious microbe contained within a harvested hairy root (e.g., a microbial hairy root inoculum). According to some embodiments of the disclosure, propagating microbial hairy roots may be performed using a vermiculite method 122, a hydroponic method 124, an in vitro media method 126, a bioreactor method 128, or any combination thereof.

According to some embodiments, propagating microbial hairy roots may be performed when a microbial hairy root attached to an infected plant or an explant has reached a desired length. In some embodiments, propagating microbial hairy roots may be performed when a microbial hairy root attached to an infected plant or an explant has reached a length of at least about 1 cm, or at least about 1.5 cm, or at least about 2 cm, or at least about 2.5 cm, or at least about 3 cm, or at least about 3.5 cm, or at least about 4 cm, or at least about 4.5 cm, or at least about 5 cm.

As described above, there are multiple in planta approaches that may be used to generate one or more microbial hairy roots. Such in planta generated microbial hairy roots may still be attached to at least a portion of an infected plant capable of photosynthetic activity (i.e., an attached hairy root). According to some embodiments, propagating microbial hairy roots 121 may include exposing an attached hairy root to one or more selective conditions (e.g., prior to being propagated). Exposing an attached hairy root to one or more selective conditions may include exposing one or more surfaces of the attached hairy root to a solution containing an alcohol (e.g., 70% ethanol), NaClO (bleach) (e.g., 2.5%, 10%), a non-phytotoxic anti-fungal (e.g., amphotericin B), an anti-bacterial (e.g., cefotaxime, carbenicillin) compound, or any combination thereof for a designated period of time (e.g., 1 to 10 minutes), according to some embodiments. In some embodiments, exposing an attached hairy root to one or more selective conditions may include exposing the attached hairy root to osmotic stress. Exposing an attached hairy root to one or more selective conditions, in some embodiments, may include transferring the attached hairy root to a selection media (e.g., about ½ MS, ½ B5+3% sucrose+200 mg/L cefotaxime or 100 mg/L carbenicillin) to inhibit (e.g., reduce a concentration of) *R. rhizogenes*.

According to some embodiments, propagating microbial hairy roots 121 may include harvesting one or more microbial hairy roots from an explant, an infected plant, a portion of an infected plant, or an attached hairy root to form a harvested hairy root. Propagating microbial hairy roots 121 may include exposing a harvested hairy root to selective conditions which, in some embodiments, may reduce a concentration of *R. rhizogenes*. Exposing a harvested hairy root to one or more selective conditions may include exposing one or more surfaces of the harvested hairy root to a solution containing an alcohol (e.g., 70% ethanol), NaClO (bleach) (e.g., 2.5%, 10%), a non-phytotoxic anti-fungal (e.g., amphotericin B), an anti-bacterial (e.g., cefotaxime or carbenicillin) compound, or any combination thereof for a designated period of time (e.g., 1 to 10 minutes), according to some embodiments. In some embodiments, exposing a harvested hairy root to one or more selective conditions may include transferring a harvested hairy root to a selection media (e.g., about ½ MS, ½ B5+3% sucrose+200 mg/L cefotaxime or 100 mg/L carbenicillin). In some embodiments, exposing a harvested hairy root to one or more selective conditions may include exposing a harvested hairy root to osmotic stress. For example, a harvested hairy root may be exposed to osmotic stress by repeated rinsing in sterilized de-ionized water for a period of time (e.g., about 30 minutes).

As shown in FIG. 1 at 122, propagating microbial hairy roots may be performed using a vermiculite method 122. A vermiculite method 122, in some embodiments, may include transplanting an attached hairy root (e.g., a surface sterilized attached hairy root) into a vermiculite matrix. According to some embodiments, a vermiculite method 122 of propagating microbial hairy roots may include periodically transferring an attached hairy root to a fresh vermiculite matrix. A transplanted attached hairy root in a vermiculite matrix may be placed in suitable conditions for maintenance of a photosynthetic portion of the attached hairy root. For example, the vermiculite hairy roots may be propagated in a growth chamber with a diurnal cycle of 14 hour of light (intensity: 100 μmol m$^{-2}$ s$^{-1}$), 10 hour dark, and 21° C. to about 25° C.

According to some embodiments, propagating microbial hairy roots may be performed using a hydroponic method 124. A hydroponic method 124 may include, according to some embodiments, placing an attached hairy root (e.g., exposed to osmotic stress) or a harvested hairy root (e.g., surface sterilized) in a nutrient rich medium (e.g., ½ MS or ½ B5+3% sucrose media) to generate a hydroponic culture. In some embodiments, a nutrient rich medium may include antibiotics or antifungal components. A hydroponic culture may be maintained at any appropriate conditions for growth of an attached hairy root or a harvested hairy root. In some embodiments, a hydroponic culture may be agitated. According to some embodiments, a hydroponic culture may be periodically supplemented with an additional nutritional source (e.g., a fresh media supply). A hydroponic culture, in some embodiments, may be maintained at a temperature of about 21° C. to about 25° C. According to some embodiments, supplying an external light source is unnecessary for growth of a hydroponic culture. As shown in FIG. 1 at 126, propagating microbial hairy roots may be performed using an in vitro media method 126. An in vitro media method 126 may include, according to some embodiments, placing an attached hairy root (e.g., exposed to osmotic stress) or a harvested hairy root (e.g., surface sterilized) on a plate of nutrient rich media (e.g., ½ MS or ½ B5+3% sucrose media) to generate an in vitro culture. In some embodiments, a nutrient rich medium may include antibiotics or antifungal components. An in vitro culture may be maintained at any appropriate conditions for growth of an attached hairy root or a harvested hairy root. According to some embodiments, an in vitro media method 126 may include periodically transplanting an attached hairy root or a harvested hairy root to a fresh plate of nutrient rich media. An in vitro culture, in some embodiments, may be maintained at a temperature of about 21° C. to about 25° C. According to some embodiments, supplying an external light source is unnecessary for growth of an in vitro culture.

As shown in FIG. 1 at 128, according to some embodiments, propagating microbial hairy roots may be performed using a bioreactor method 128. A bioreactor method 128 may include, according to some embodiments, placing an attached hairy root (e.g., exposed to osmotic stress) or a harvested hairy root (e.g., surface sterilized) in a bioreactor system containing a nutrient rich medium (e.g., ½ MS, ½ B5+3% sucrose media) to generate a bioreactor culture. In some embodiments, a nutrient rich medium may include antibiotics or antifungal components.

Various bioreactor systems may be used without deviating from the present disclosure. For example, in some embodiments, liquid-phase and/or gas-phase bioreactors may be used in a bioreactor method of propagating microbial hairy roots. According to some embodiments, an immersion system bioreactor or a temporary immersion system bioreactor (e.g., the SETIS system) may be used in a bioreactor method of propagating microbial hairy roots. In some embodiments, an attached hairy root or a harvested hairy root may be periodically immersed in a nutrient rich medium for a period of time calculated to allow sufficient uptake of nutrients (e.g., a temporary immersion system bioreactor). In some embodiments, a temporary immersion system may contribute to an improvement of gas exchange and avoidance of hypoxia/aeration issues when compared to an immersion system where plant tissues are perpetually immersed in a nutrient medium. A temporary immersion system (e.g., SETIS system) may be inexpensive, easy to establish, and/or scalable (e.g., highly scalable). Individual units of a temporary immersion system may be designed to function independently, in some embodiments. According to some embodiments, individual units of a bioreactor may be multiplexed such that a first bioreactor unit is attached to at least a second bioreactor unit. A multiplexed bioreactor set-up may reduce loss due to contamination when compared to a single bioreactor unit as contamination can be prevented from spreading from unit to unit.

A bioreactor culture may be maintained at any appropriate conditions for growth of an attached hairy root or a harvested hairy root. In some embodiments, a bioreactor culture may be aerated. According to some embodiments, a bioreactor culture may be periodically supplemented with an additional nutritional source (e.g., a fresh media supply). A bioreactor culture, in some embodiments, may be maintained at a temperature of about 21° C. to about 25° C. According to some embodiments, supplying an external light source is unnecessary for growth of a bioreactor hairy root culture.

According to some embodiments, propagating microbial hairy roots may be achieved in a relatively short period of time. In some embodiments, a microbial hairy root population may be generated from an infected plant or an explant to a propagated mass of microbial hairy roots in about six to ten weeks.

A Hairy-Root Genetic Screening System

As illustrated in FIG. 1 at 130, in addition to alleviating previous challenges of culturing fastidious vascular-limited plant microbes, a hairy root platform may be readily exploited for transformative, high-throughput functional studies including but not limited to genetic and chemical screens for novel antimicrobials and bactericides. Because *R. rhizogenes* may effectively induce hairy roots in diverse monocot and dicot plants, microbial hairy root systems, methods, and compositions for microbial cultivation may be applied to other agronomic crops and plant microbe associations beyond vascular-colonizing phytobacteria such as fungi, viruses, viroids, and endophytic microbes.

Assays may be performed using microbial hairy roots that remain attached to plant tissue, such as aerial hairy root shown in FIG. 1 at 132 or microbial hairy roots generated using a rock wool or vermiculite method as shown in FIG. 1 at 134, according to some embodiments. In some embodiments, assays may be performed using harvested microbial hairy roots, as shown in FIG. 1 at 136 where a multi-well assay is illustrated.

Microbial hairy root systems, methods, and compositions, according to some embodiments, may solve a long standing problem in plant pathology to culture fastidious microbes and/or enable transformative biological and genetic studies of the fastidious microbes. For example, a microbial hairy root system may be deployed for rapid screening of novel resistance genes, antimicrobial compounds, bactericides, etc. Such screening may help fight devastating diseases such as ZC and HLB. Microbial hairy roots can also be leveraged to better understand the interactions occurring between the host-pathogen-vector. Therefore, microbial hairy root systems, methods, and compositions disclosed herein may advance U.S. agriculture and plant disease management by aiding in developing control strategies of potentially-devastating fastidious plant microbes.

A microbial hairy root platform and system disclosed herein may be integrated into programs towards identification of novel resistance genes and antimicrobial compounds. For example, the system may help achieve rapid functional and chemical genetic screening of candidate disease resistance genes and antimicrobial molecules (e.g., antibiotics, essential oils, oxylipins) in a plant (e.g., tomato, potato, citrus) microbial hairy root systems. Because *R. rhizogenes* may effectively induce hairy roots in diverse dicot and monocots, the disclosed principles may also establish microbial hairy root systems for other crops and plant microbe associations beyond vascular-limited phytobacteria, such as fungi, viruses, viroids, and beneficial endophytes. In some embodiments, a hairy root system may be used to study plant microbes (e.g., economically important plant microbes) and their corresponding diseases (e.g., zebra chip (ZC), HLB).

The present disclosure relates, in some embodiments, to a microbial hairy root platform for rapid culture, propagation, and functional studies of fastidious vascular colonizing plant microbes (e.g., pathogens). According to some embodiments, microbe-colonized hairy roots induced directly from colonized plants may provide an easy, rapid, and scalable platform to culture, propagate, and characterize fastidious vascular-limited plant microbes (e.g., in the laboratory).

According to some embodiments disclosed herein, genetic analysis (e.g., an analysis of transgene function) may be performed using a microbial hairy root system. In some embodiments, a hairy root system may comprise cultivating hairy root from a genetically modified plant by transforming the genetically modified plant with a strain of *R. rhizogenes*. For example, a plant that is genetically modified to overexpress a plant Broad-complex, Tramtrack and Bric-abrac (BTB) domain family protein, NPR1, or green florescent protein (GFP) may be transformed with a strain of *R. rhizogenes* to induce production of a hairy root. In some embodiments, a genetically modified plant transformed by *R. rhizogenes* may be colonized by a fastidious microbe (e.g., Las, Lso). As with other embodiments described herein either the hairy root culture can be first developed and then exposed to the pathogen to infect hairy roots or the hairy root culture can be developed from a plant already infected with the pathogen. For example, as it relates to transgenic plants, a hairy root culture of a healthy plant is created and then it is exposed to a fastidious microbe. A tissue from one or more parts of a plant as an explant source is selected to make an explant. Then one contacts the explant with a suspension of *Rhizobium rhizogenes* under conditions that permit induction of hairy roots to form a hairy root on the explant. Then one propagates the hairy root to form a propagated hairy root; and finally contact the propagated hairy root with a fastidious plant microbe to form a fastidious plant colonized hairy root. As discussed herein, the plant can also be infected with a pathogen and the explant is taken from the infected plant and used for the development of hairy roots.

A hairy root system may comprise, in some embodiments, transforming a plant with a R. rhizogenes strain having one or more modified T-DNA plasmids. For example, in some embodiments, a modified R. rhizogenes may be formed. A modified R. rhizogenes may comprise one or more T-DNA plasmids, each encoding at least one of a target gene (e.g., NPR1, GFP), a CRISPR/Cas, a TALEN, or an RNAi construct, in some embodiments. According to some embodiments, a hairy root system may comprise transforming a plant with a R. rhizogenes strain having a first modified T-DNA plasmid and a second modified T-DNA plasmid, with each of the first T-DNA plasmid and the second T-DNA plasmid encoding at least one of a target gene, a CRISPR/Cas, a TALEN, or an RNAi construct. In some embodiments, a T-DNA plasmid may encode a library of target genes. Because R. rhizogenes can simultaneously transfer T-DNA and Ri-DNA into plant cells, transformation of a plant with a modified R. rhizogenes may result in production of a plant producing hairy roots that express (e.g., overexpress) at least one of a target gene, a CRISPR/Cas, a TALEN, or an RNAi construct.

According to some embodiments, one or more T-DNA plasmid encoding at least one of a target gene (e.g., NPR1, GFP), a CRISPR/Cas, a TALEN, or an RNAi construct, may be delivered transiently into a hairy root using mild vacuum infiltration or DNA bombardment; thereby forming a genetically modified hairy root.

In some embodiments, a T-DNA plasmid encoding at least one of a target gene (e.g., NPR1, GFP), a CRISPR/Cas, a TALEN, or an RNAi construct may further comprise a reporter/marker gene (e.g., GFP, β-glucuronidase [GUS], antibiotic resistance gene). Because the use of standard antibiotics for the induction and selection of microbial hairy roots is controlled, green fluorescent protein (GFP)-based or GUS-based screening may be used (e.g., optionally, exclusively) to identify microbial hairy roots harboring a modified T-DNA construct.

In some embodiments, transformation of a hairy root with at least one of a target gene (e.g., NPR1, GFP), a CRISPR/Cas, a TALEN, or an RNAi construct may be confirmed using reverse-transcription PCR (RT-PCR), PCR, DNA-sequencing, Southern blot analysis, northern blot analysis, and/or western blot analysis. Hairy roots co-transformed or infiltrated with an empty or GFP containing binary T-DNA vector may be used as a negative control. A person having skill in the art would understand that other methods of confirmation of transformation with a target gene may be used without deviating from the present disclosure.

Evaluation of at least one of a target gene (e.g., NPR1, GFP), a CRISPR/Cas, a TALEN, or an RNAi construct may include quantitative analysis of titers of a fastidious plant microbe colonizing a hairy root system. For example, a target gene that is involved in resistance mechanisms may have reduced titers of the fastidious plant microbe when compared to a colonized hairy root that does not contain the target gene. Evaluation of titers of a fastidious plant microbe may include qualitative or quantitative evaluations.

As an example, a hairy root system may be used to perform a genetic analysis of a NPR1, GFP gene. The Broad-complex, Tramtrack and Bric-abrac (BTB) domain family of proteins are well-conserved in plants and are involved in diverse plant signaling pathways. For example, a plant BTB protein, NPR1, may be modulated by diverse abiotic and biotic stress signals including salicylic-acid, methyl-jasmonate, reactive oxygen species, and wounding in Arabidopsis. Therefore, to evaluate the NPR1 gene's potential role in a response to a fastidious plant microbe (e.g., Lso, Las), a hairy root system may be used. For example, a potato, a tomato, and a citrus plant cultivated by their respective Lso or Las pathogen may be transformed with a R. rhizogenes strain having a T-DNA plasmid containing a NPR1 gene or a GFP gene. To determine the effect of NPR1 on Lso and Las, bacterial titers in the hairy roots overexpressing NPR1 may be quantified and compared to the control hairy roots expressing only GFP. For example, the resulting titers may indicate that expression (e.g., overexpression) of the NPR1 gene promoted resistance (or tolerance) to Lso and Las in the hairy roots. Together, these tests may provide rapid functional applications using the disclosed microbial hairy roots.

Several antimicrobials such as bactericides (e.g. penicillin, oxytetracycline), immune modulators, resistance/susceptibility genes and peptides are available or being tested to control fastidious microbes. However, current efficacy screening techniques are laborious and time-consuming, slowing the pace of discovery. For instance, the average testing time to evaluate the efficacy of an antimicrobial gene in potato, tomato or citrus, using either stable transformation or via transient viral vectors (e.g., Tobacco rattle virus, Citrus tristeza virus, CTV), followed by mature plant disease challenges could take six months to several years. Similarly, screening of bactericides or other therapeutics by foliar sprays or injections into plant stem/trunk are laborious and are not high throughput. In some cases, researchers have resorted to using distantly related, culturable, surrogate plant microbes (e.g., Liberibacter crescens, Propionibacterium acnes, Xanthomonas spp.)[28, 29], however the results are not reliable owing to differences in the host-range and virulence mechanisms of the microbes and varying lifestyles.

Accordingly, embodiments of the invention provide a novel and versatile platform to cultivate fastidious microbes by leveraging plant hairy root cultures. The microbial hairy root cultures offer an alternative, yet powerful system to conduct high throughput antimicrobial screening of disease resistance genes (gain-of-function studies), susceptibility genes (loss-of-function studies) and small-molecule therapies. Using Candidatus Liberibacter spp. as a case pathogen, the inventors demonstrated production of hairy root cultures of this pathogen and demonstrated their utility in screening small-molecules and transgenes as well as conduct CRISPR-CAS9-based genome editing experiments. The antimicrobial screening in the microbial hairy root cultures can be accomplished up to four times faster than with conventional approaches. Furthermore, the results demonstrate that the potato NPR3 is a negative regulator of plant defense, and possibly works antagonistically to NPR1, which is a positive regulator that confers tolerance to Candidatus Liberibacter spp. Because hairy roots can be readily induced from diverse plant species, the microbial hairy root strategy can be applicable to culture diverse plant-fastidious pathogen systems and beyond vascular-limited bacteria to include viruses, spiroplasmas, mycoplasma-like organisms and unculturable beneficial microbes.

As will be understood by those skilled in the art who have the benefit of the instant disclosure, other equivalent or alternative compositions, devices, methods, and systems for cultivating fastidious plant microbes can be envisioned without departing from the description contained herein. Accordingly, the manner of carrying out the disclosure as shown and described is to be construed as illustrative only.

Persons skilled in the art may make various changes in the nature, number, and/or arrangement of steps without departing from the scope of the instant disclosure. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Where open terms such as "having" or "comprising" are used, one of ordinary skill in the art having the benefit of the instant disclosure will appreciate that the disclosed features or steps optionally may be combined with additional features or steps. Such option may not be exercised and, indeed, in some embodiments, disclosed systems, compositions, apparatuses, and/or methods may exclude any other features or steps beyond those disclosed herein. Elements, compositions, devices, systems, methods, and method steps not recited may be included or excluded as desired or required. Persons skilled in the art may make various changes in methods of preparing and using a composition, device, and/or system of the disclosure.

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value +/–about 10%, depicted value +/–about 50%, depicted value +/–about 100%) and/or a range endpoint. With respect to the former, a value of 50 depicted in an example, table, and/or drawing may form the basis of a range of, for example, about 45 to about 55, about 25 to about 100, and/or about 0 to about 100.

All or a portion of a device and/or system for cultivating a fastidious microbes may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

The title, abstract, background, and headings are provided in compliance with regulations and/or for the convenience of the reader. They include no admissions as to the scope and content of prior art and no limitations applicable to all disclosed embodiments.

EXAMPLES

Example 1: Generating an Explant and/or Inoculum Source

Figure 2A:
FIG. 2A illustrates adult psyllids being propagated in contained traps using eggplants as host plants, according to an embodiment of the disclosure.
Figure 2B:
FIG. 2B illustrates adult psyllids carrying Lso being propagated in contained traps using eggplants as host plants, according to an embodiment of the disclosure.

FIGS. 2A through 2G illustrate an example of using fastidious microbe carrying insect vectors to generate plants colonized by the fastidious microbe for use as explants in hairy root methods and systems. Specifically, FIGS. 2A and 2B illustrate Lso-carrying and Lso-free potato psyllid colonies (Central haplotype), maintained in insect cages at the Texas A&M AgriLife Center-Weslaco. The psyllids were originally collected from commercial potato fields near Dalhart, Tex. in 2007. As shown in FIG. 2A and FIG. 2B, the psyllids were fed on eggplants and kept at 25° C. with a 12:12 light:darkness (L:D) hour photoperiod and about 50% relative humidity in a controlled growth chamber. Periodically, a psyllid colony (e.g., Lso-carrying, Lso-free) was tested for the presence or absence of Lso colonization using 16S rDNA PCR.

Figure 2C:
FIG. 2C illustrates healthy tomato leaves at four weeks post-psyllid exposure, according to an embodiment of the disclosure.
Figure 2D:
FIG. 2D illustrates Lso-infected tomato leaves at four weeks post-psyllid exposure, according to an embodiment of the disclosure.
Figure 2E:
FIG. 2E illustrates healthy potato leaves at four weeks post-psyllid exposure, according to an embodiment of the disclosure.
Figure 2F:
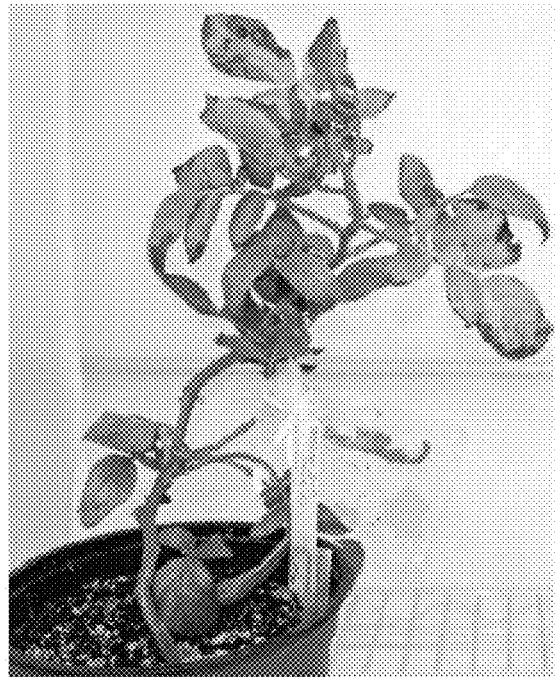
FIG. 2F illustrates Lso-infected tomato leaves at four weeks post-psyllid exposure, according to an embodiment of the disclosure.

To generate explant material, ten adult Lso-carrying psyllids were released into cages containing two-month to three-month-old potato and tomato plants and permitted to feed. As a control, ten Lso-free psyllids were released into a separate set of cages containing two-month to three-month-old potato and tomato plants and permitted to feed. After a period of three days, the psyllids were removed and foliar symptoms (chlorosis and necrosis) on the infected potato and tomato plants were monitored. As shown in FIGS. 2D and 2F respectively, typical disease symptoms began to appear on the tomato and potato plants exposed to the feeding of Lso-carrying psyllids within two to four weeks after feeding. By contrast, those tomato (FIG. 2C) and potato (FIG. 2E) plants that were exposed to Lso-free psyllid feeding did not exhibit disease symptoms (FIG. 2C and FIG. 2E respectively).

Figure 2G:
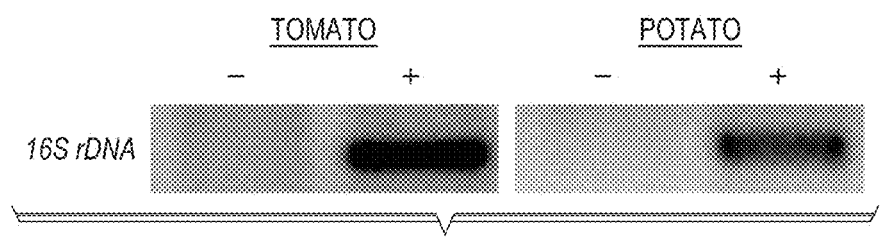
FIG. 2G illustrates polymerase chain reaction (PCR)-based confirmation of Lso in infected tomato and potato leaves.

As shown in FIG. 2G, the presence of Lso in the infected plants (e.g., tomato in FIG. 2D and potato in FIG. 2F) was validated by PCR amplification of 16S rDNA. Plant material that tested positive for Lso infection was used as a source of explant (for in vitro approaches) and as a colonized plant (for in planta approaches) for microbial hairy root induction.

Example 2: Culturing *Rhizobium rhizogenes*

A fresh culture of *R. rhizogenes* was cultured to an optical density (OD) of about 0.3. The culture was pelleted by centrifugation and the *R. rhizogenes* cells were re-suspended in a sterile ½ MS or ½ B5+3% sucrose medium to an O.D. of 0.3.

Example 3: In Vitro Induction of Microbial Hairy Roots

Figure 3A:
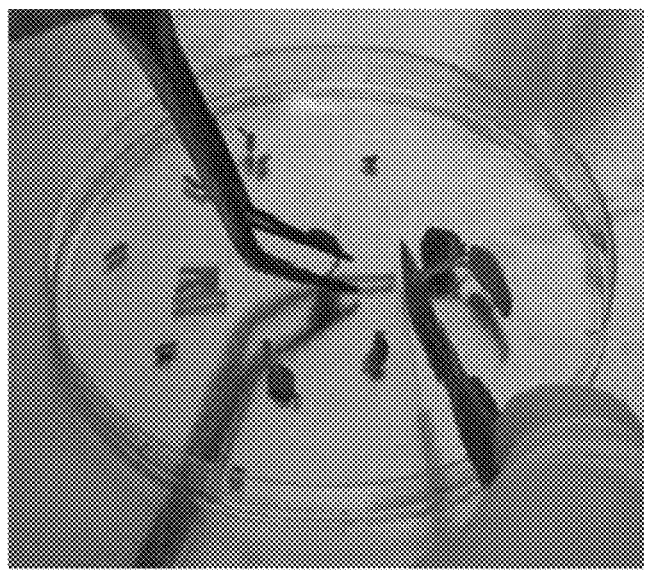
FIGS. 3A-3E illustrate, according to specific example embodiments of the disclosure, a schematic of an in vitro microbial hairy root platform.

Portions of both healthy plants and plants colonized with Lso were harvested including cotyledon, hypocotyl, immature shoot, and immature root regions. The plant portions were surface sterilized using a solution containing 70% ethanol, 2.5% or 10% NaClO, and water. As shown in FIG. 3A, portions of the surface sterilized plants were cut using a scalpel into pieces having a length of about 2 cm each. Additionally, each of the pieces was gently wounded using a sterilized pair of fine forceps to generate prepared explants.

Figure 3B:
Figure 3C:
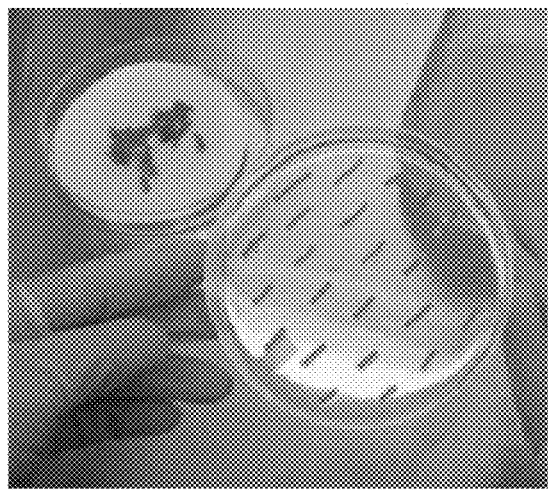

As shown in FIG. 3B, the prepared explants were contacted with a suspension of *R. rhizogenes* by immersion in a suspension prepared as described in EXAMPLE 2. The immersed explants were agitated for a period of 20 min. As shown in FIG. 3C, the explants were then removed from the suspension of *R. rhizogenes* and placed on a plate of ½ MS or ½ B5+3% sucrose medium. The explants were incubated on plate for 72 hours at about 21-25° C. thereby allowing the explant and *R. rhizogenes* to co-cultivate.

Figure 3D:
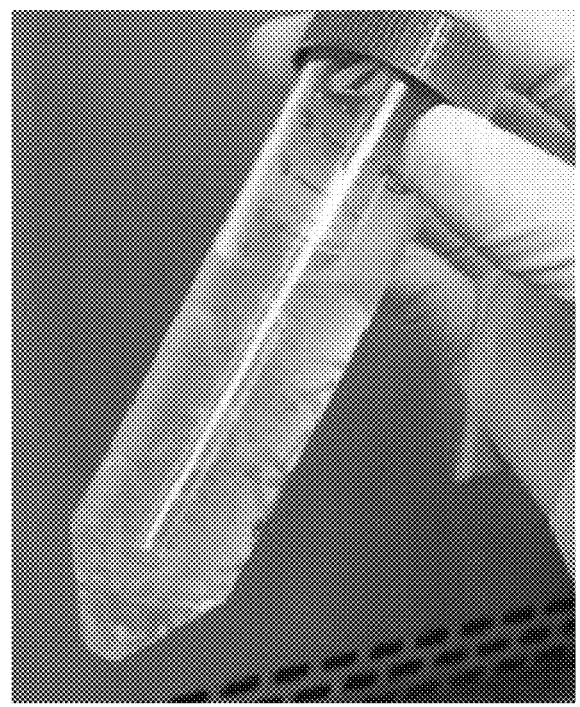
Figure 3E:
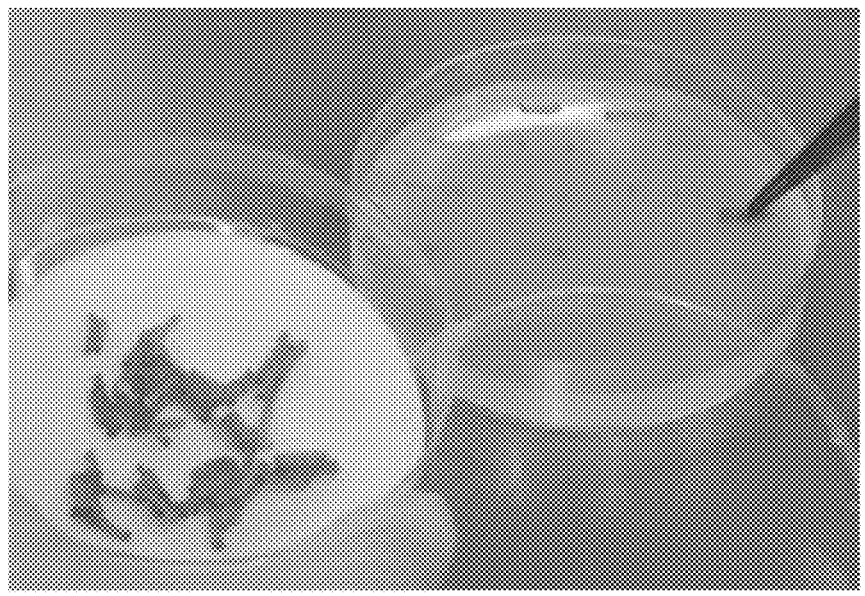

After co-cultivation, the explants were subjected to osmotic stress to reduce the concentration of *R. rhizogenes*. The explants were removed from the plate of ½ MS or ½ B5+3% sucrose media and placed in a volume of sterilized de-ionized water, as shown in FIG. 3D. The suspension of explants in the sterilized deionized water was agitated for about 30 minutes. The explants were then removed and transferred to a selection medium of % MS or ½ B5+3% sucrose+200 mg/L cefotaxime or 100 mg/L carbenicillin, as shown in FIG. 3E.

The plates of selection media containing the explants were then placed in an incubator at 25° C. and monitored for hairy root induction. Depending on the plant species, the explant source, and the R. rhizogenes strain used, hairy roots emerged within two to six weeks.

Figure 4A:
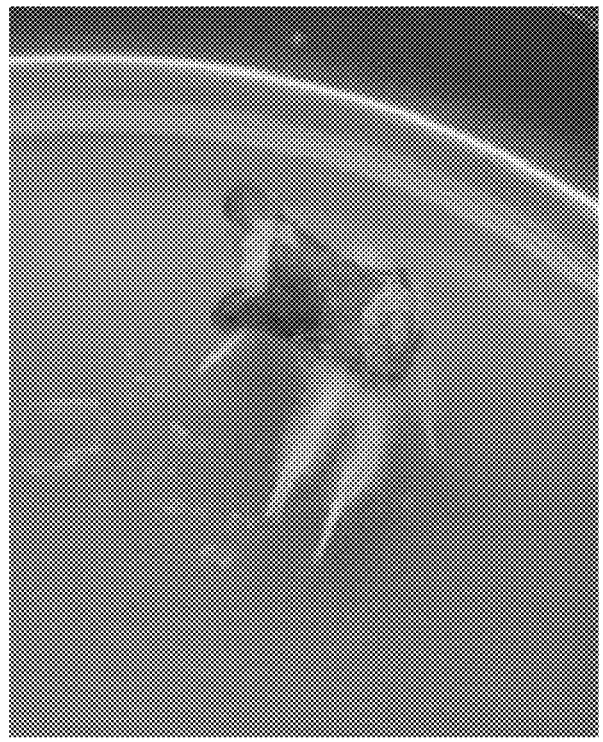
FIG. 4A illustrates in vitro induction of hairy roots on a tomato explant transformed with *Rhizobium rhizogenes* (strain ATCC 15834), according to an embodiment of the disclosure.
Figure 5A:
FIG. 5A illustrates in vitro induction of hairy roots on a potato explant transformed with *Rhizobium rhizogenes*, according to an embodiment of the disclosure.
Figure 6A:
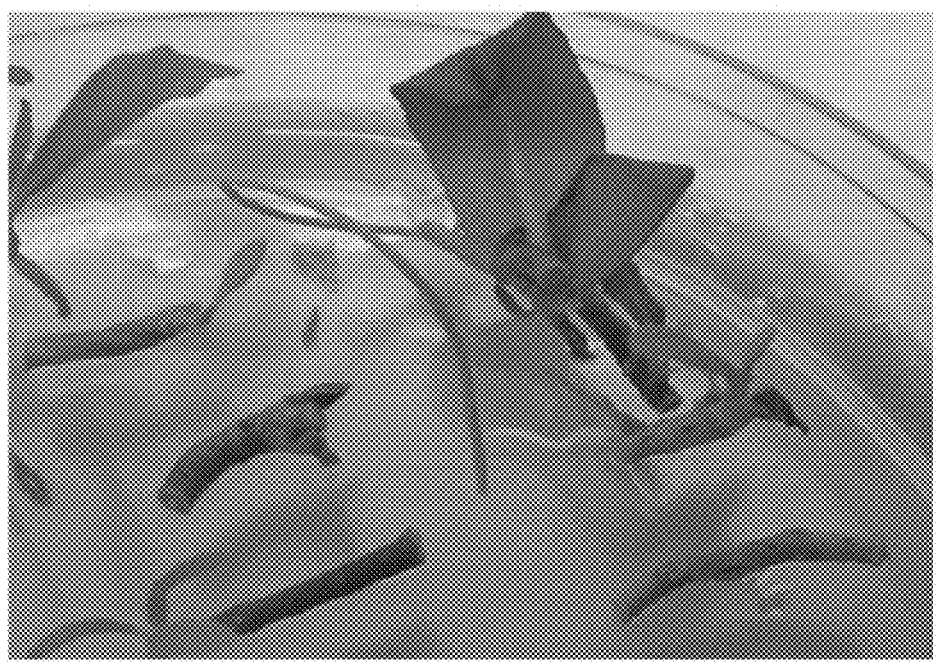
FIG. 6A illustrates in vitro induction of hairy roots on citrus (Eureka lemon) explants transformed with *Rhizobium rhizogenes* (strain ATCC 15834), according to an embodiment of the disclosure.

FIG. 4A illustrates in vitro induction of hairy roots on a tomato explant transformed with Rhizobium rhizogenes (strain ATCC 15834). FIG. 5A illustrates in vitro induction of hairy roots on a potato explant transformed with Rhizobium rhizogenes. FIG. 6 illustrates in vitro induction of hairy roots on citrus (Eureka lemon) explants transformed with Rhizobium rhizogenes (strain ATCC 15834).

The structures were confirmed as hairy roots using PCR amplification of known root inducing (Ri) DNA genes rolB and rolC.

Figure 4B:
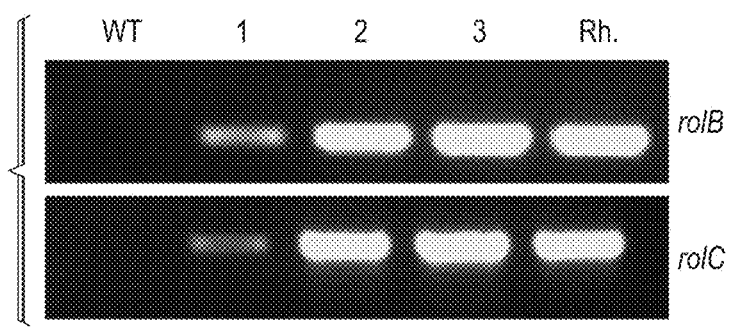
FIG. 4B shows PCR validation results of hairy roots on a tomato explant, according to an embodiment of the disclosure.

FIG. 4B shows PCR validation results of tomato hairy roots induced in vitro with Rhizobium rhizogenes (strain ATCC 15834), where rolB and rolC are marker genes for transformed hairy roots. As shown in FIG. 4B: lane WT shows PCR amplification of DNA from wild type tomato that was not transformed with R. rhizogenes (negative control); lane 1 shows PCR amplification of DNA from a hairy root of an explant transformed by R. rhizogenes with tomato variety Castlemart; lane 2 shows PCR amplification of DNA from a hairy root of an explant transformed by a R. rhizogenes with tomato variety University of California 82 (UC82); lane 3 shows a PCR amplification of DNA from a hairy root of a second explant transformed by R. rhizogenes strain UC82; and lane Rh shows a PCR amplification of DNA from R. rhizogenes cells (positive control).

Figure 5B:
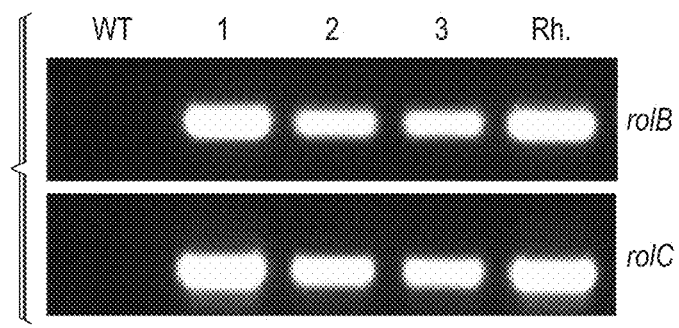
FIG. 5B shows PCR validation results of hairy roots on a potato explant, according to an embodiment of the disclosure.

FIG. 5B shows PCR validation of potato (Atlantic) hairy roots from an explant transformed with Rhizobium rhizogenes (strain ATCC 15834), where rolB and rolC are marker genes for transformed hairy roots. Of the five lanes shown in FIG. 5B, Lane WT represents DNA from wild type potato (negative control), Lane 1 represents potato hairy root sample 1, Lane 2 represents potato hairy root sample 2, Lane 3 represents potato hairy root sample 3, and Lane Rh represents R. rhizogenes cells (positive control).

Figure 6B:
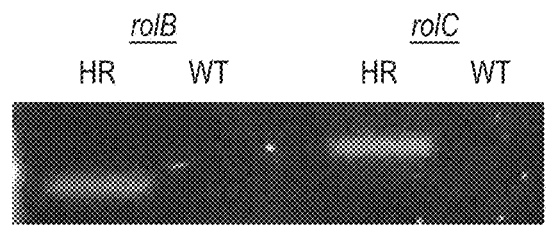
FIG. 6B shows PCR validation results of hairy roots on citrus (Eureka lemon) explants transformed with *Rhizobium rhizogenes* (strain ATCC 15834), according to an embodiment of the disclosure.

FIG. 6B shows PCR validation of citrus (Eureka lemon) hairy roots from an explant transformed with Rhizobium rhizogenes (strain ATCC 15834). Of the two lanes for each of rolB and rolC shown in FIG. 68, lanes marked HR (hairy roots) represent DNA from hairy roots, and Lane WT represents DNA from wild type citrus (negative control).

Example 4: In Planta Induction of Aerial Microbial Hairy Roots and Transgene Delivery Healthy plants (control) and plants infected with Lso were selected, and select plant surfaces were surface sterilized using a solution containing 70% ethanol, 2.5% or 10% NaClO (bleach), and water. A suspension of R. rhizogenes was prepared as described in EXAMPLE 2.

Figure 7A:
FIG. 7A shows aerial hairy roots induced on a healthy tomato by *Rhizobium rhizogenes*, according to an embodiment of the disclosure.
Figure 7B:
FIG. 7B shows aerial microbial hairy roots induced on an Lso-colonized tomato by *Rhizobium rhizogenes*, according to an embodiment of the disclosure.
Figure 8A:
FIG. 8A shows aerial hairy roots induced on an Lso-colonized potato by *Rhizobium rhizogenes*, according to an embodiment of the disclosure.

Induction of aerial microbial hairy roots was performed by gently wounding stem tissue and/or leaf tissue of a surface sterilized region of an Lso colonized plant using a needle dipped in the R. rhizogenes solution. The R. rhizogenes strain used contained both an Ri-DNA plasmid and a T-DNA plasmid with the T-DNA plasmid encoding a green fluorescent protein (GFP). Healthy plants were also induced for aerial hairy root formation using the method described above for use as an experimental control. The exposed wound sites were wrapped in aluminum foil to reduce exposure to light and help maintain desired humidity levels at the area of exposure. The plants were maintained in a growth chamber with appropriate temperature, light, and humidity conditions for each plant species. Plants were monitored for the formation of microbial hairy roots. FIG. 7A illustrates the formation of aerial hairy roots on a healthy tomato plant. FIG. 7B illustrates the formation of aerial microbial hairy roots on an Lso colonized tomato plant. FIG. 8A illustrates the formation of aerial microbial hairy roots on an Lso colonized potato plant.

Figure 7C:
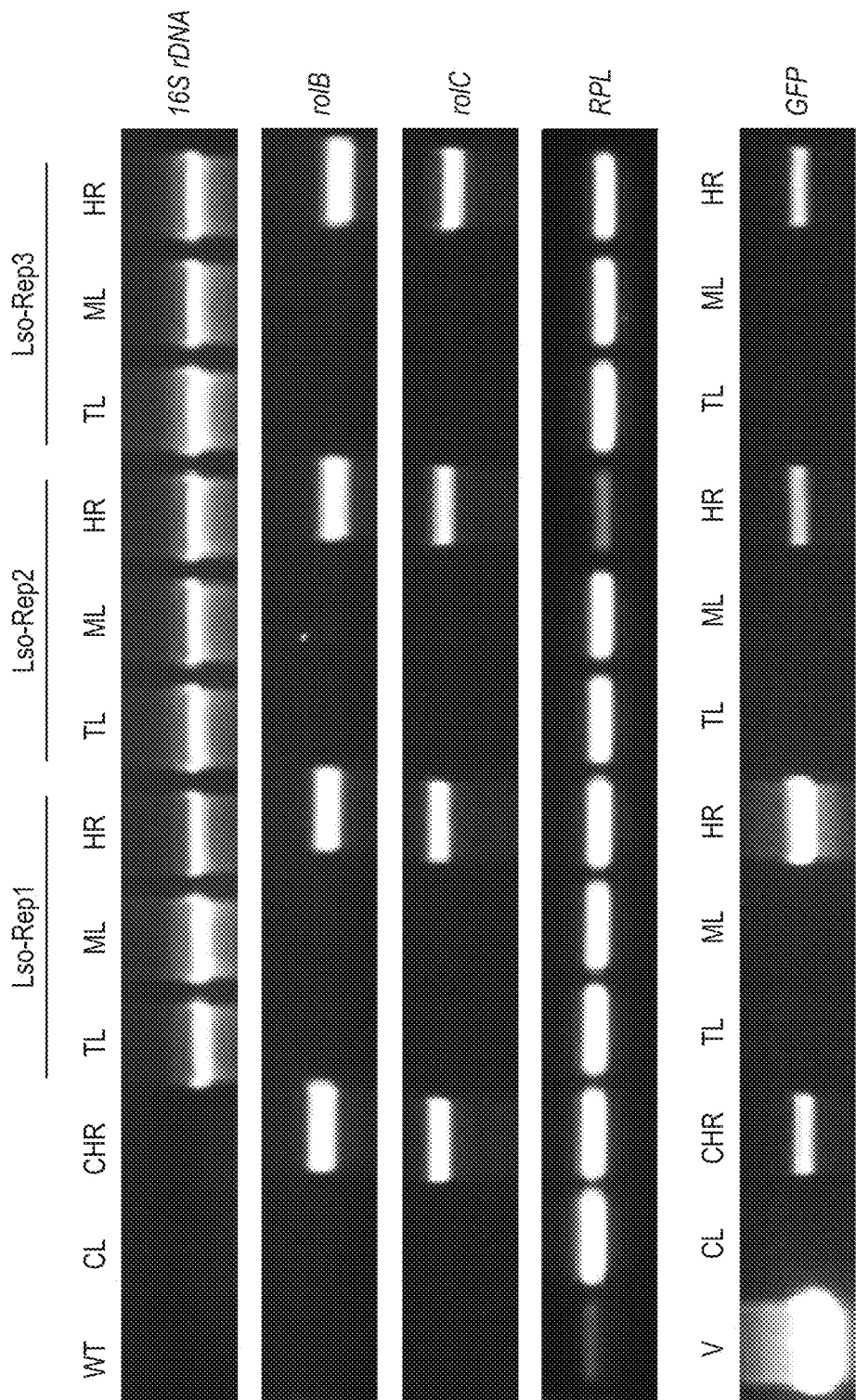
FIG. 7C shows PCR validation results of aerial hairy roots on tomato, according to an embodiment of the disclosure.

The structures were confirmed as microbial hairy roots using PCR amplification of known root inducing (Ri) DNA genes rolB and rolC. As shown in FIG. 7C, PCR validation of aerial microbial hairy root tissue was performed using DNA samples from microbial hairy roots pictured in FIGS. 7A and 7B. Primers were designed to amplify 16S rDNA of Lso (labelled in the row marked 16S rDNA), rolB and rolC marker genes from hair root transformation, an endogenous tomato gene RPL (control), and GFP gene encoded on the T-DNA plasmid. DNA from healthy plant tissue was gathered and amplified using the primer sets. The lanes of FIG. 7C representing healthy plant DNA are as follows: WT represents DNA from a wild type tomato plant (negative control), CL represents DNA from a healthy tomato leaf (negative control), and CHR represents DNA from a healthy hairy root (negative control for 16SrDNA primers). DNA was also extracted from Lso infected plant tissue including: a top leaf of an Lso infected tomato (TL), a middle leaf of an Lso infected tomato (ML), and an aerial microbial hairy root from an Lso infected tomato (HR). Three replicates were performed for the Lso infected tissue. As shown in FIG. 7C the CHR and HR samples replicated the rolB and rolC genes; thus showing that these were in fact hairy roots. The HR, but not CHR, amplified the 16S rDNA segments, establishing that the HR were Lso colonized.

A separate PCR gel was run to confirm the co-transformation of both the Ri-DNA plasmid (encoding rolB and rolC) and the T-DNA plasmid (encoding GFP). For this gel plasmid DNA comprising the T-DNA vector (labelled V) was extracted and amplified using the GFP primer set. As shown in FIG. 7C this served as a positive control for the amplification of GFP. FIG. 7C shows that in the CHR and HR samples the GFP gene was amplified, establishing that the Ri-DNA and T-DNA were co-transformed during the generation of the aerial hairy roots.

Figure 8B:
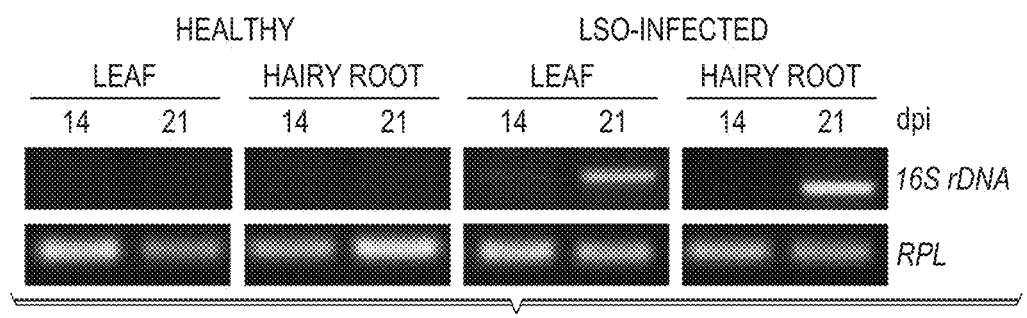
FIG. 8B shows PCR validation results of aerial hairy roots on potato, according to an embodiment of the disclosure.
Figure 8C:
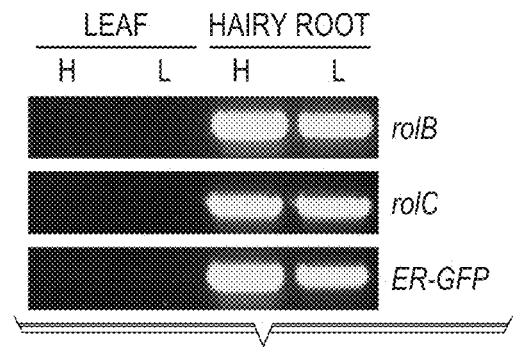
FIG. 8C shows PCR validation results of aerial microbial hairy roots on potato, according to an embodiment of the disclosure.

FIG. 8B illustrates the PCR amplification of 16S rDNA in 21 day old Lso-infected aerial hairy root samples taken from the Lso infected potato shown in FIG. 8A. Amplification of the RPL gene served as a positive control. FIG. 8C illustrates the PCR amplification of the rolB, rolC, and GFP genes in hairy root tissues from healthy ("H") potato plants and Lso infected ("L") potato plants; thus establishing that the Ri-DNA and T-DNA were co-transformed during the generation of the aerial hairy roots.

Example 5: In Planta Induction of Microbial Hairy Roots Using a Rock Wool Method and Transgene Delivery Healthy tomato plants (control) and tomato plants infected with Lso were selected, and select plant surfaces were surface sterilized using a solution containing 70% ethanol, 2.5% or 10% NaClO (bleach), and water. A suspension of R. rhizogenes was prepared as described in EXAMPLE 2. The R. rhizogenes contained both an Ri-DNA plasmid (including rolB and rolC genes) and a T-DNA plasmid encoding GFP.

A shoot portion of the selected tomato plants was removed using a scalpel and the wounded portion of the shoot was inserted in a rock wool matrix. A volume of the R. rhizogenes suspension was used to saturate the rock wool matrix, and the matrix was placed in a culture vessel to maintain a high humidity level. The R. rhizogenes was permitted to co-cultivate with the wound sites of the healthy tomato plants and the Lso infected tomato plants for 72 hours. After 72 hours the rock wool matrix was removed and the rock wool was permitted to dry, thereby killing most of the R. rhizogenes. The rock wool matrix was exposed to the ambient environment for approximately 24 hours before being rehydrated. The treated shoot and rock wool matrix was transferred to a new plastic magenta box culture vessel with nutrient solution (½ MS or MA B5), and placed in a diurnal growth chamber and monitored for generation of microbial hairy roots.

Figure 9A:
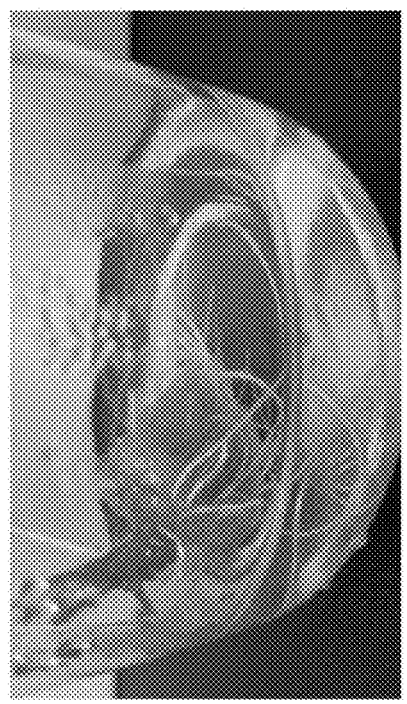
FIG. 9A shows microbial hairy roots induced on an Lso-colonized tomato using a rock wool method, according to an embodiment of the disclosure.
Figure 9A:
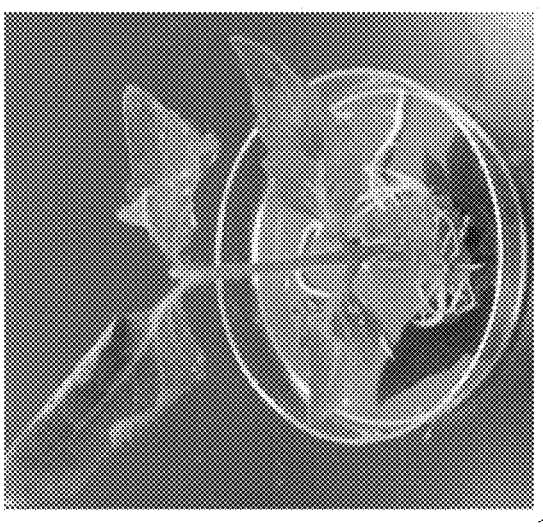

FIG. 9A shows the generation of microbial hairy roots on an Lso infected tomato plant.

Figure 9B:
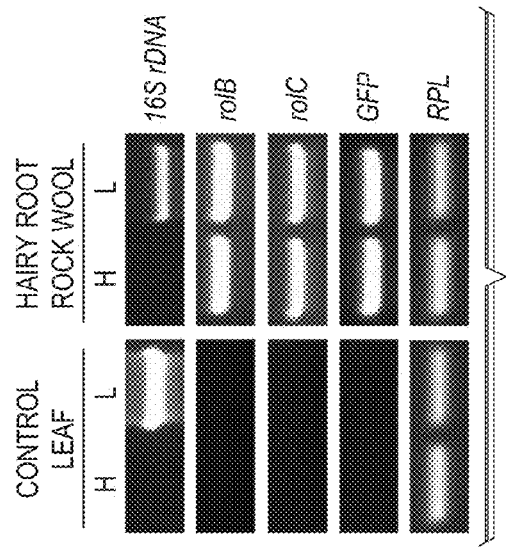
FIG. 9B shows PCR validation results of microbial hairy roots on tomato induced using a rock wool method, according to an embodiment of the disclosure.

PCR validation was performed to confirm the microbial hairy root constructs, the colonization of the microbial roots with Lso, and the co-transformation with both the Ri-DNA and T-DNA plasmids. FIG. 9B illustrates the PCR amplification of rolB, rolC, and GFP genes in hairy root tissues from healthy ("H") potato plants and Lso infected ("L") potato plants; thus establishing that the Ri-DNA and T-DNA were co-transformed during the co-cultivation with R. rhizogenes. As expected, the 16SrDNA was only amplified in the Lso infected microbial hairy roots.

Example 6: In Planta Induction of Microbial Hairy Roots Using a Vermiculite Method and Transgene Delivery Healthy plants (control) and plants infected with Lso were selected, and select plant surfaces were surface sterilized using a solution containing 70% ethanol, 2.5% or 10% NaClO (bleach), and water. A suspension of R. rhizogenes was prepared as described in EXAMPLE 2. The R. rhizogenes contained both an Ri-DNA plasmid (including rolB and rolC genes) and a T-DNA plasmid encoding GFP.

A shoot portion of the selected plants was removed using a scalpel and the wounded portion of the shoot was submerged in the R. rhizogenes suspension. A vacuum environment of about 30 inHg was generated and held for 30 minutes. After release of the vacuum, the shoot was removed from the R. rhizogenes suspension and placed in a vermiculite matrix. The shoots were placed in a covered tray in a growth chamber at 25° C. with a light/dark cycle of 14 hours of light followed by 10 hours of dark. The shoots were monitored for microbial hairy root generation.

Figure 10A:
FIG. 10A shows microbial hairy roots induced on a tomato plant using a vermiculite method, according to an embodiment of the disclosure.
Figure 10B:
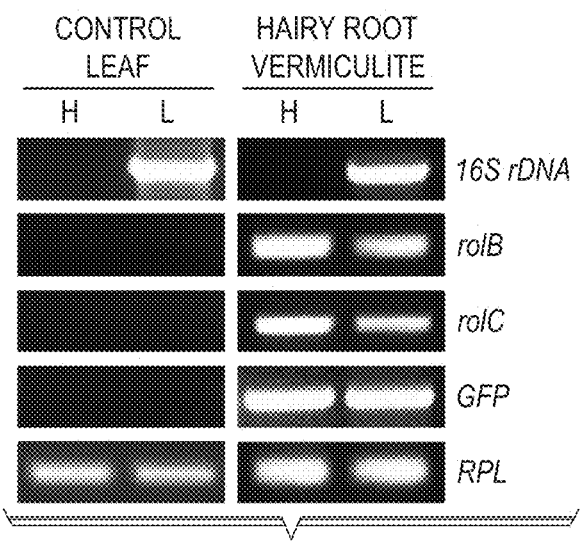
FIG. 10B shows PCR validation results of microbial hairy roots on tomato induced using a vermiculite method, according to an embodiment of the disclosure.

FIG. 10A illustrated microbial hairy root growth from a tomato plant induced using the vermiculite method. PCR validation was performed to confirm the microbial hairy root constructs, the colonization of the microbial roots with Lso, and the co-transformation with both the Ri-DNA and T-DNA plasmids. FIG. 10B illustrates the PCR amplification of rolB, rolC, and GFP genes in hairy root tissues from healthy ("H") tomato plants and Lso infected ("L") tomato plants; thus establishing that the Ri-DNA and T-DNA were co-transformed during the co-cultivation with R. rhizogenes. As expected, the 16S rDNA was only amplified in the Lso infected microbial hairy roots.

Figure 11:
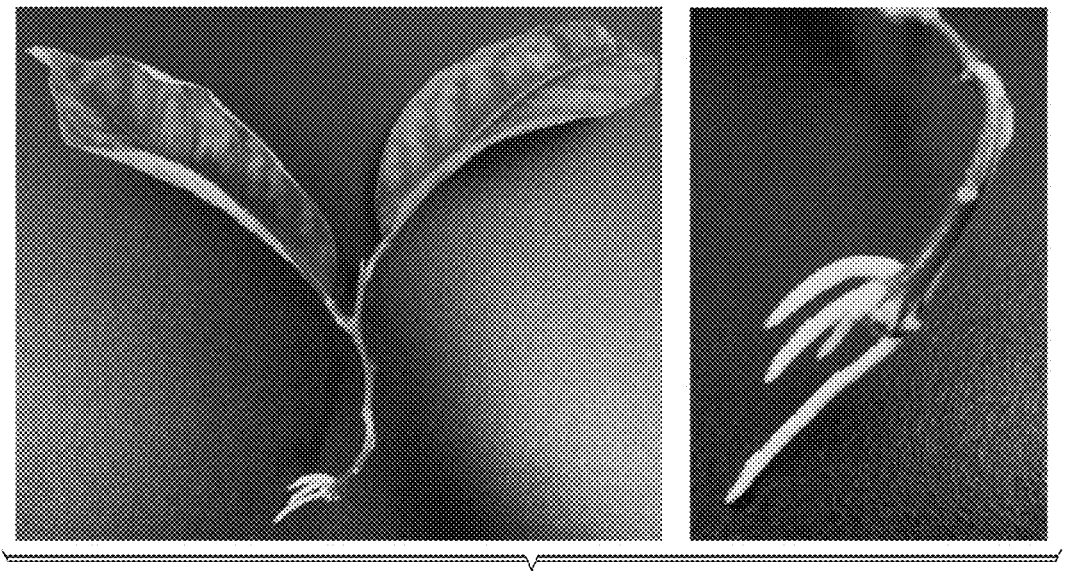
FIG. 11 shows microbial hairy roots induced on a Las infected citrus (sour orange) using a vermiculite method, according to an embodiment of the disclosure.

FIG. 11 illustrates the generation of microbial hairy roots from shoots of citrus (Sour orange) using the vermiculite method.

Example 7: Propagation of Hairy Roots-Vermiculite Method

A harvested hairy root may be clonally propagated. Clonal propagation of a harvested hairy root may provide an increased source of a fastidious microbe contained within a harvested hairy root (e.g., a microbial hairy root inoculum).

Hairy roots generated from both healthy tomato plants and Lso infected tomato plants, as described above in EXAMPLE 4, were selected for propagation. The tomato plants were cut directly below the site where aerial hairy roots generated and the lower stem and root portion of the plant was discarded. The shoot portion attached to the aerial hairy roots was maintained (i.e., an attached hairy root).

Figure 12:
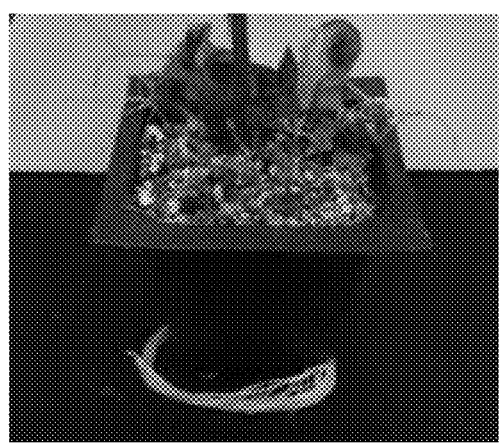
FIG. 12 illustrates propagated hairy roots growing in a vermiculite matrix, according to an embodiment of the disclosure.

The aerial hairy roots were surface sterilized by submerging the roots in a 70% ethanol solution, 2.5% or 10% bleach solution, and then rinsing with de-ionized water. The attached hairy roots were then transplanted into a vermiculite matrix. The transplanted attached hairy roots were placed in a growth chamber at 25° C. with a light/dark cycle of 14 hours of light followed by 10 hours of dark. The shoots were monitored for propagation of the hairy roots. FIG. 12 illustrates the propagated hairy roots growing from the bottom of a vermiculite containing pot.

Example 8: Propagation of Microbial Hairy Roots—Hydroponic Method

Figure 13:
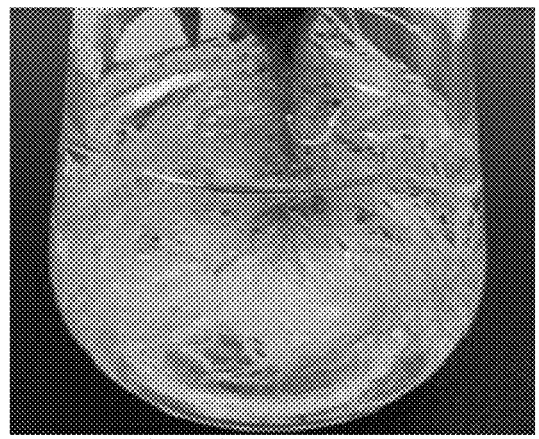
FIG. 13 illustrates propagated hairy roots growing in a hydroponic culture, according to an embodiment of the disclosure.

Hairy roots generated from both healthy tomato plants and Lso infected tomato plants, as described above in EXAMPLE 4, were selected for propagation. The aerial hairy roots of the tomato plants were harvested when they reached a length of at least 3 cm. The harvested aerial hairy roots were surface sterilized by submerging the harvested roots in a 70% ethanol solution, 2.5% or 10% bleach solution, and then rinsing with de-ionized water. The harvested hairy roots were then placed in a beaker containing ½ MS or ½ B5+3% sucrose+200 mg/L cefotaxime or 100 mg/L carbenicillin, and 2.5 mg/L amphotericin B. The hydroponic culture was maintained at 25° C. with gentle agitation at 50 or 100 rpm. FIG. 13 illustrates the propagated hairy roots growing in a hydroponic culture.

Example 9: Propagation of Microbial Hairy Roots—In Vitro Method

Figure 14:
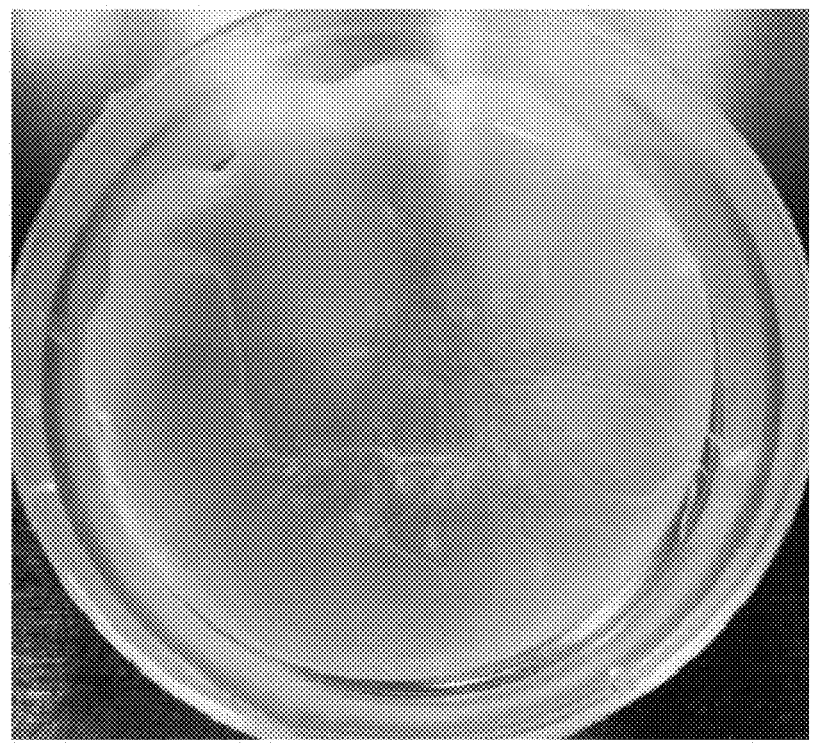
FIG. 14 illustrates propagated hairy roots growing in an in vitro culture, according to an embodiment of the disclosure.

Hairy roots generated from both healthy tomato plants and Lso infected tomato plants, as described above in EXAMPLE 4, were selected for propagation. The aerial hairy roots of the tomato plants were harvested when they reached a length of at least 3 cm. The harvested aerial hairy roots were surface sterilized by submerging the harvested roots in a 70% ethanol solution, 2.5% or 10% bleach solution, and then rinsing with de-ionized water. The harvested hairy roots were then placed on a plate containing ½ MS or ½ B5+3% sucrose+200 mg/L cefotaxime or 100 mg/L carbenicillin, and 2.5 mg/L amphotericin B. The in vitro culture was maintained at 25° C. FIG. 14 illustrates the propagated hairy roots growing in a hydroponic culture. The nutrient media was replaced with fresh media on a weekly basis.

Example 10: Propagation of Microbial Hairy Roots—Bioreactor Method

Figure 15:
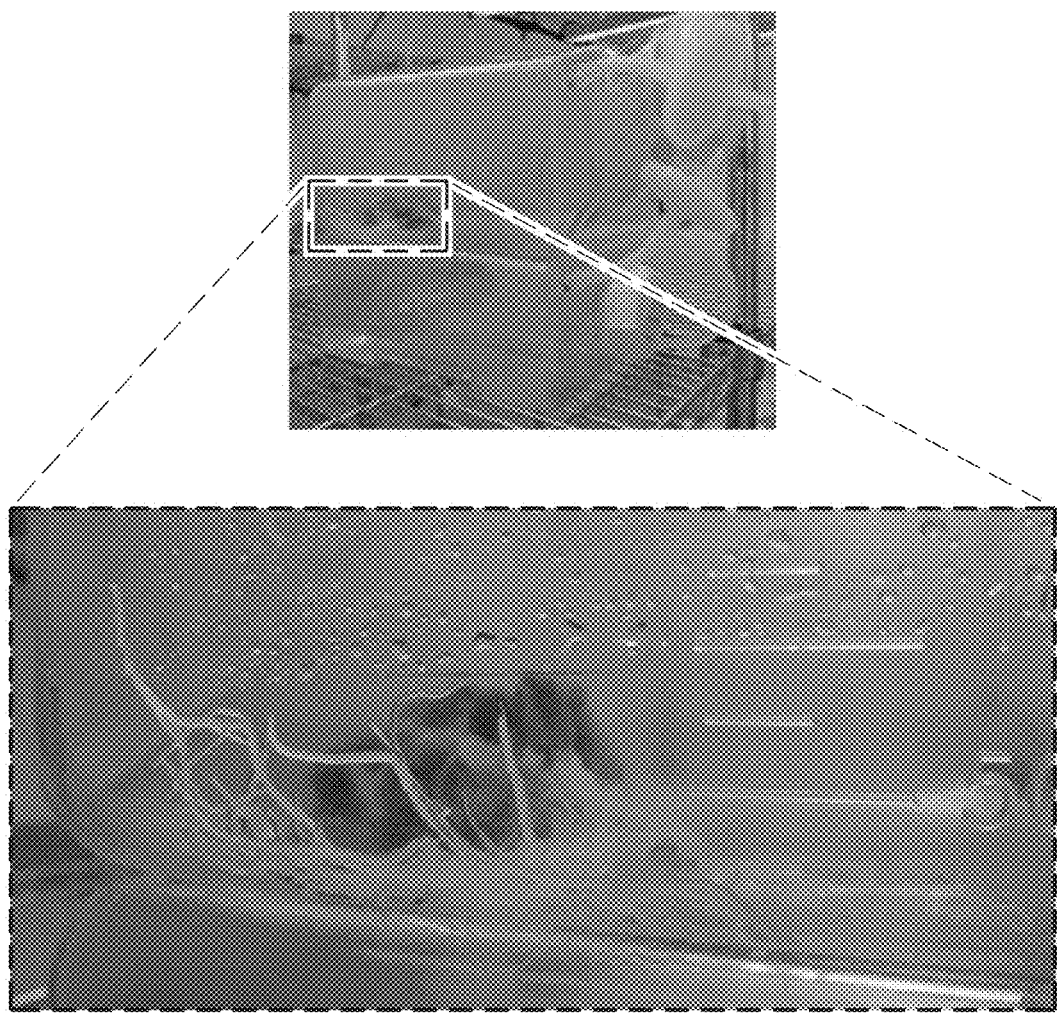
FIG. 15 illustrates propagated hairy roots growing in a bioreactor system, according to an embodiment of the disclosure.

Hairy roots generated from both healthy tomato plants and Lso infected tomato plants, as described above in EXAMPLE 9, were selected for propagation using a bioreactor method. The hairy roots were harvested from the in vitro culture or in planta methods, were surface sterilized by submerging the harvested roots 70% ethanol solution, 2.5% or 10% bleach solution, and then rinsing with de-ionized water, and placed in a SETIS system containing ½ MS or ½ B5+3% sucrose+200 mg/L cefotaxime or 100 mg/L carbenicillin, and 2.5 mg/L amphotericin B. The bioreactor culture was maintained at 25° C. FIG. 15 illustrates the propagated hairy roots growing in a bioreactor system. The nutrient media was replaced with fresh media every three to four weeks.

Example 11: High-Throughput Antimicrobial Assays

Figure 16A:
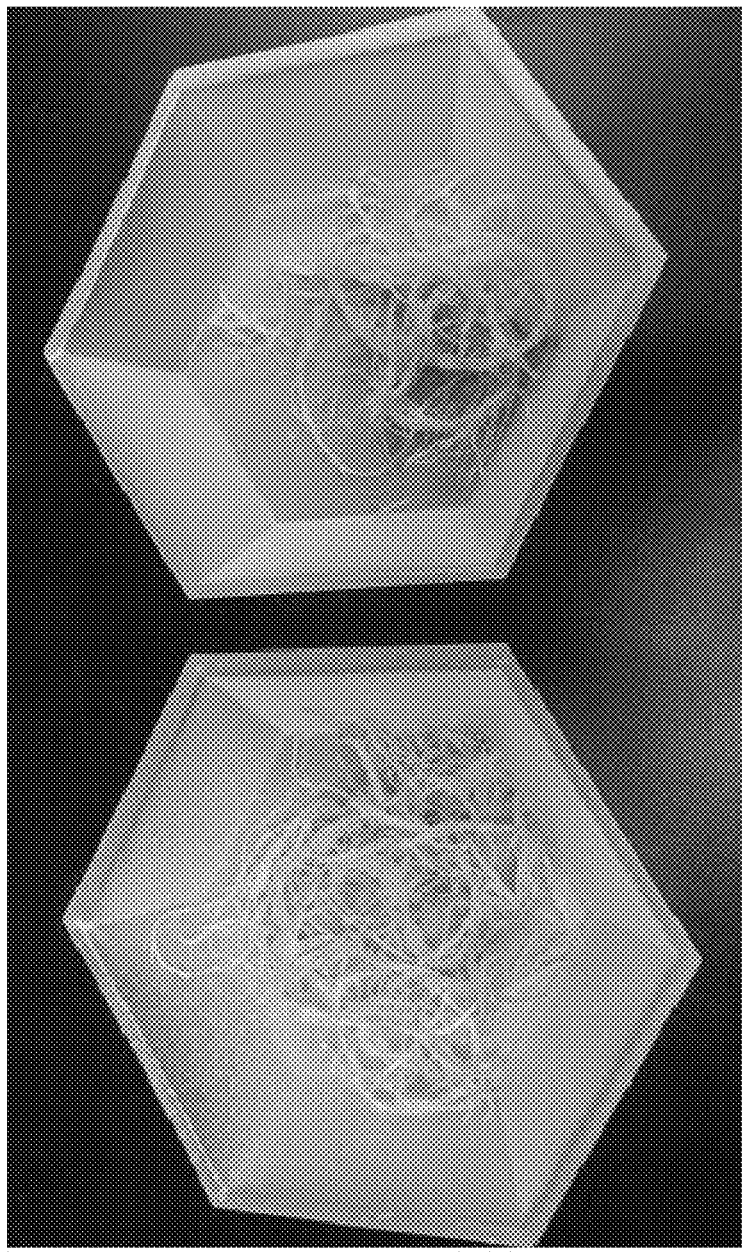
FIG. 16A shows healthy and Lso-colonized hairy roots harvested from an in vitro or in planta system, according to an embodiment of the disclosure.
Figure 16B:
FIG. 16B shows healthy and Lso-colonized microbial hairy roots distributed into a multi-well plate, according to an embodiment of the disclosure.

Microbial hairy roots were used to analyze whether Lso is inhibited by antimicrobials such as penicillin. As shown in FIG. 16A, healthy hairy roots and Lso colonized microbial hairy roots were harvested from either in vitro or in planta propagation. The hairy roots were separated and weighed into equal quantities (e.g., 50 or 100 mg/per well). Healthy hairy roots and Lso colonized microbial hairy roots were similarly distributed into three or more biological replicates into wells of a multi-well plate, as shown in FIG. 16B. Two milliliters of ½ MS or ½ B5 media was placed into each of the control wells of the multi-well plate, submerging the hairy roots, serving as the negative control. Two milliliters of ½ MS or ½ B5+100 mg/L penicillin media was placed into each of the experimental wells of the multi-well plate, submerging the hairy roots. The multi-well plate was placed in a vacuum environment and a pressure of 25 inHg was drawn for a period of 15 to 30 minutes. The multi-welled plates with hairy roots were covered with aluminum foil to prevent light exposure and possible degradation of antibiotics. The multi-welled plates with their respective treatments were then incubated at a temperature of 25° C. with gentle shaking on a shaker (50 rpm) for a period of 2 days and 7 days.

Figure 16C:
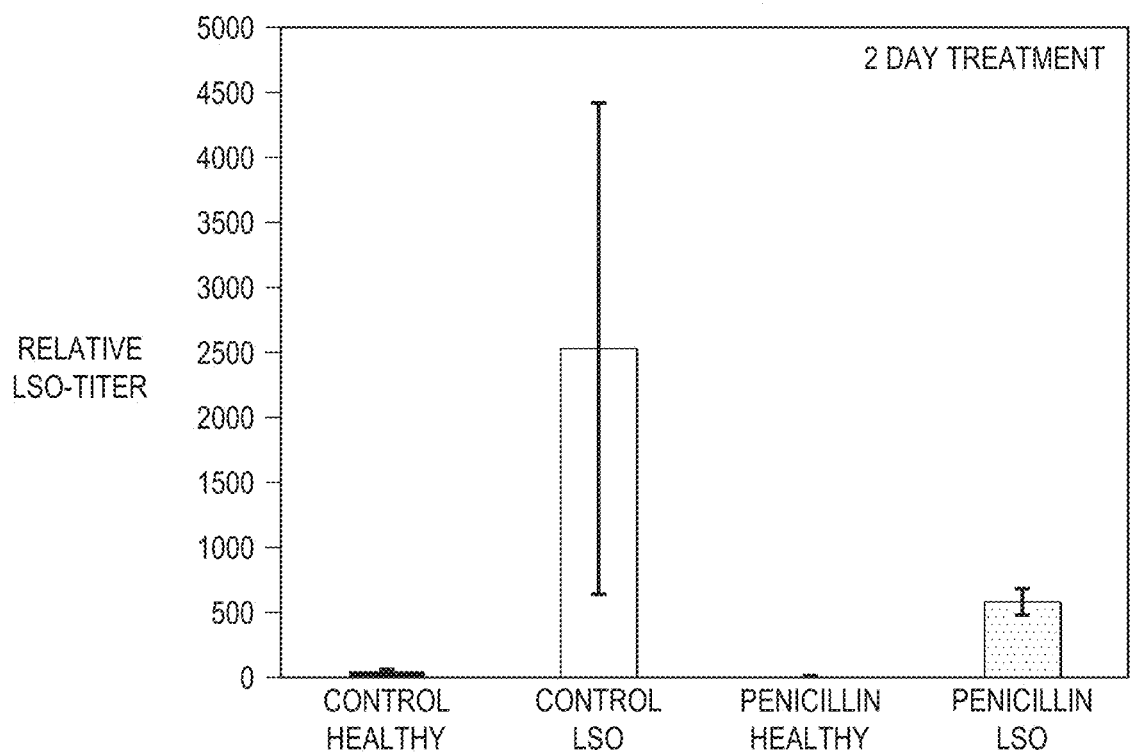
FIG. 16C shows Quantitative Real Time PCR results of an Lso titer after a 2 day treatment of hairy roots with penicillin.
Figure 16D:
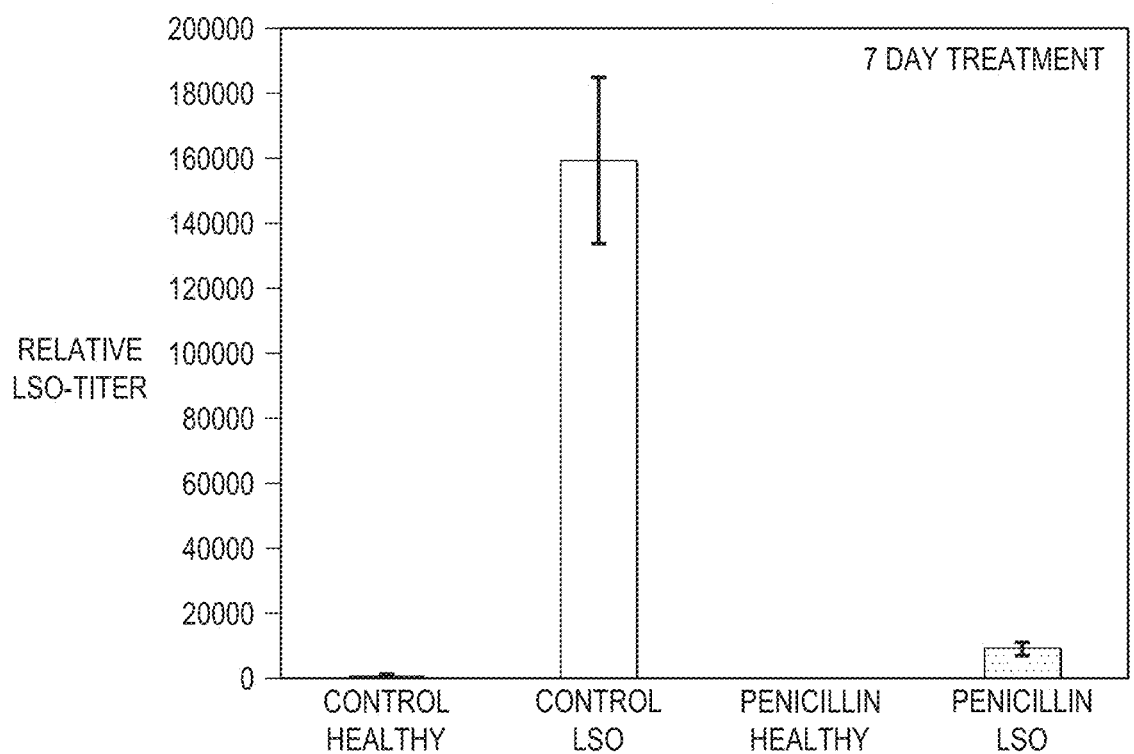
FIG. 16D shows Quantitative Real Time PCR results of an Lso titer after a 7 day treatment of hairy roots with penicillin.

Quantitative Real Time PCR was used to evaluate the Lso titer using primers to amplify 16s rDNA sequences. As shown in FIGS. 16C and 16D, the Lso colonized microbial hairy roots exposed to penicillin showed a significantly lower titer of Lso than the Lso colonized microbial hairy roots that were not exposed to penicillin after both 2 days and 7 days of exposure.

Example 12: Demonstration of Successful Cultivation of Two Different Fastidious Plant Microbes, Lso and Las, in Two Different, Unrelated Plants The following tests are presented below to demonstrate successful cultivation of two different fastidious plant microbes, Lso and Las, in two different, unrelated plants—potato and citrus plants—followed by successful evaluation of antimicrobial therapies in hairy roots, in addition to tomato, as described above.

For potato microbial hairy root bioassays, one-month-old potato plants (Atlantic variety) were grown in a growth chamber at 21° C., which were challenged with 20 psyllids harboring Lso (Lso⁺ psyllids). Plants were screened for Lso after two weeks of challenge using PCR. Branches were excised from healthy (unchallenged) and Lso-positive plants after 21 days post-challenge for hairy root transformation. For citrus microbial hairy root bioassays, Las-positive citrus tissues (confirmed by PCR) were collected from field grapefruit trees and healthy branches were collected from grapefruit trees maintained in greenhouse. Both potato and citrus hairy root production was carried out using *Rhizobium rhizogenes*. A reporter protein, green fluorescent protein (GFP), was also incorporated to aid in the identification of hairy roots vs. untransformed roots.

After transformation, ex-plants were co-cultivated overnight with *Rhizobium rhizogenes* in a shaker at 28° C. and planted in vermiculite inert trays. The potato ex-plants were grown in a growth chamber for one month with 14 h day length under fluorescent lights (200 µmol m$^{-2}$ s$^{-1}$) and at 21° C. for one month. The citrus ex-plants were grown in natural light greenhouse for three to four months at 25-30'C under a periodic mist spray system to maintain high humidity.

All emerging hairy roots were screened under a dissecting fluorescence microscope for GFP expression. The GFP-expressing potato/citrus root cultures were then tested to determine Lso/Las titers, as further discussed below.

Figure 17:
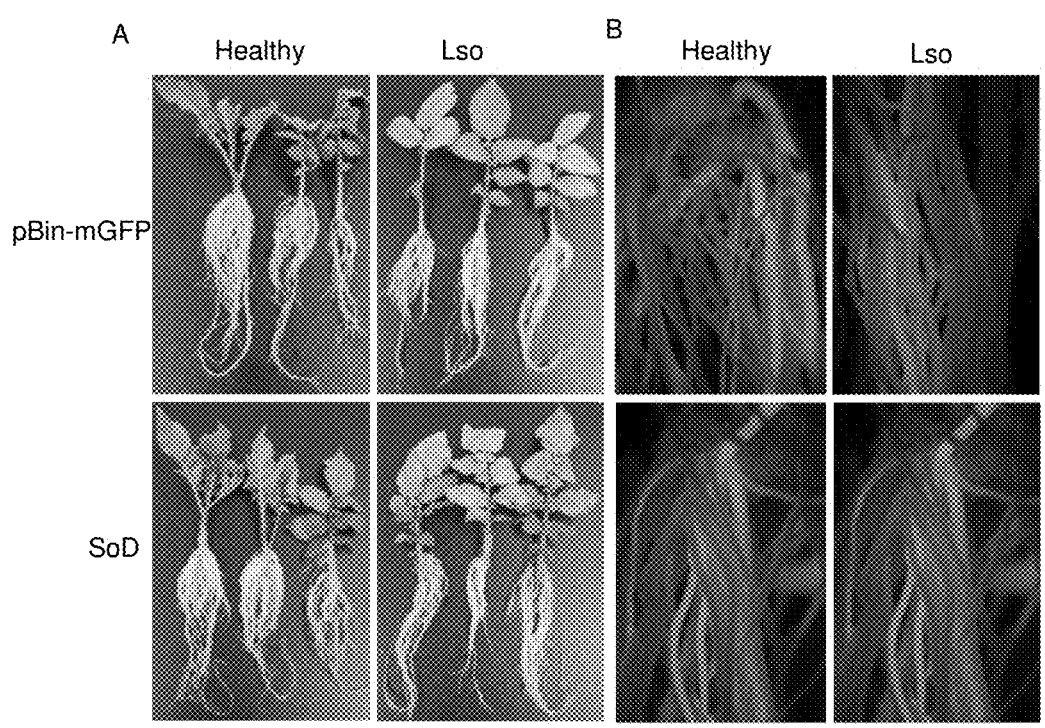
FIG. 17A provides representative images of healthy and Lso-potato hairy root cultures at 30 days post-transformation. The "SOD" values in this figure relate to a set of synthetic spinach defensin genes that were co-transformed with the *Rhizobium rhizogenes* into the potato hairy roots in this experiment.
FIG. 17B provides visualization of GFP in healthy and Lso-potato hairy root cultures under fluorescence microscope. The "SOD" values in this figure relate to a set of synthetic spinach defensin genes that were co-transformed with the *Rhizobium rhizogenes* into the potato hairy roots in this experiment.
Figure 18:
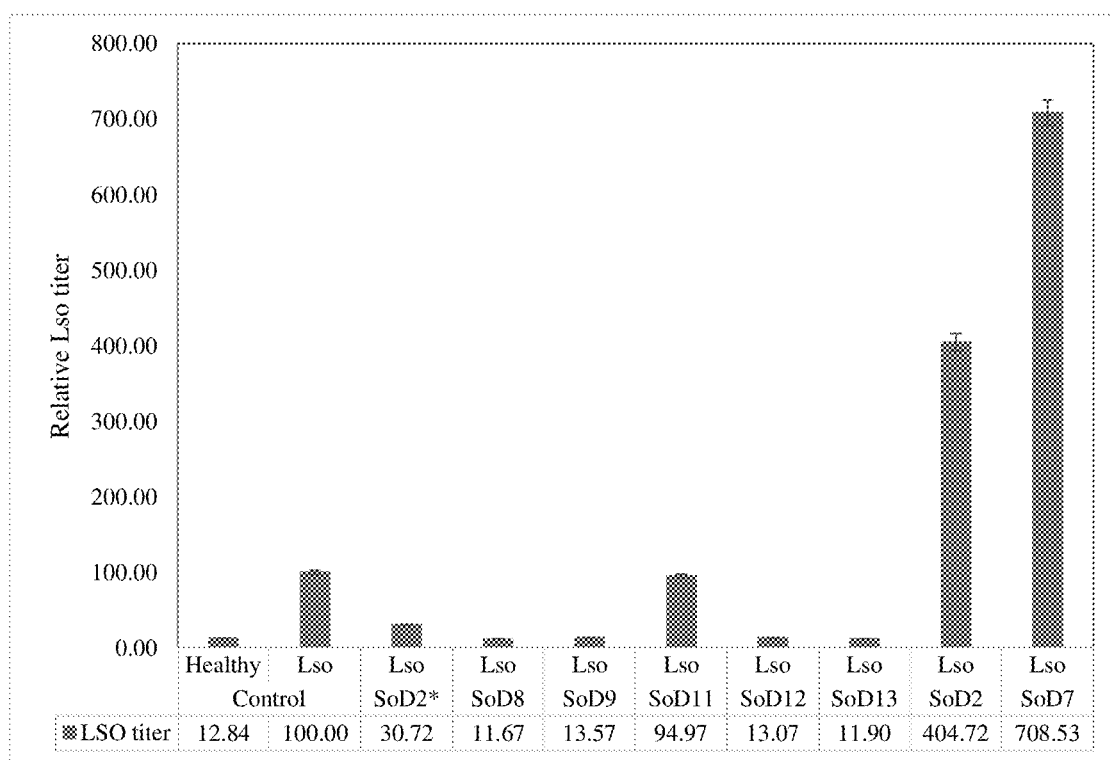
FIG. 18 shows the quantitation of Lso titers in hairy root cultures using qPCR analysis. Results are displayed as Lso titers (in %) relative to the control-infected hairy roots (set as 100%). The "SOD" values in this figure relate to a set of synthetic spinach defensin genes that were co-transformed with the *Rhizobium rhizogenes* into the potato hairy roots in this experiment.

At 30 days post-transformation (dpt), potato hairy root cultures (healthy and Lso) were screened for GFP expression (FIG. 17). RNA and genomic DNA were also extracted from the potato cultures for downstream molecular analysis. qPCR analysis was performed on a CFX384™ Real-Time PCR Detection System (Bio-Rad Laboratories, Inc., Hercules, Calif., USA) with the iTaq™ universal SYBR® Green supermix (Bio-Rad Laboratories, Inc.) and 100 ng of genomic DNA, according to the manufacturer's instructions to determine the Lso titer in 30 dpt potato hairy roots, using the Lso-F/HLBr primer pair (Lso-F: 5'-CGAGCGCTTAT-TTTTAATAGGAGC-3' (SEQ ID NO: 1)); HLBr: 5'-GCGT-TATCCCGTAGAAAAAGGTAG-3' (SEQ ID NO: 2)) (Levy et al., 2011) and RPL2 endogenous reference gene primer pair. Results were analyzed and recorded as Ct (threshold cycle) values and melting curve analysis was performed to detect non-specific amplification. The experiment was repeated three times independently and similar trends persisted (FIG. 18).

Figure 19:
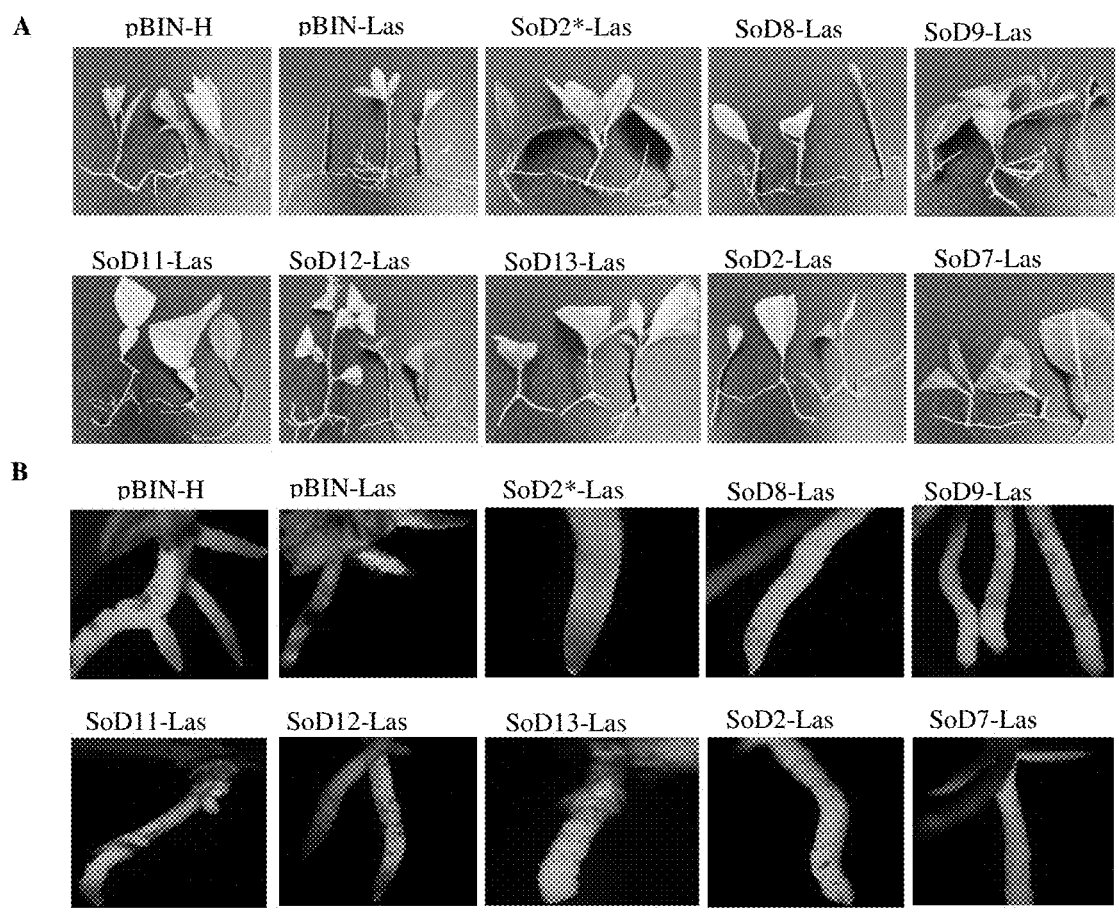
FIG. 19A provides representative images of healthy and Las-citrus hairy root cultures at 90 days post-transformation. The "SOD" values in this figure relate to a set of synthetic spinach defensin genes that were co-transformed with the *Rhizobium rhizogenes* into the potato hairy roots in this experiment.
FIG. 19B provides visualization of GFP in healthy and Las-citrus hairy root cultures under fluorescence microscope. The "SOD" values in this figure relate to a set of synthetic spinach defensin genes that were co-transformed with the *Rhizobium rhizogenes* into the potato hairy roots in this experiment.
Figure 20:
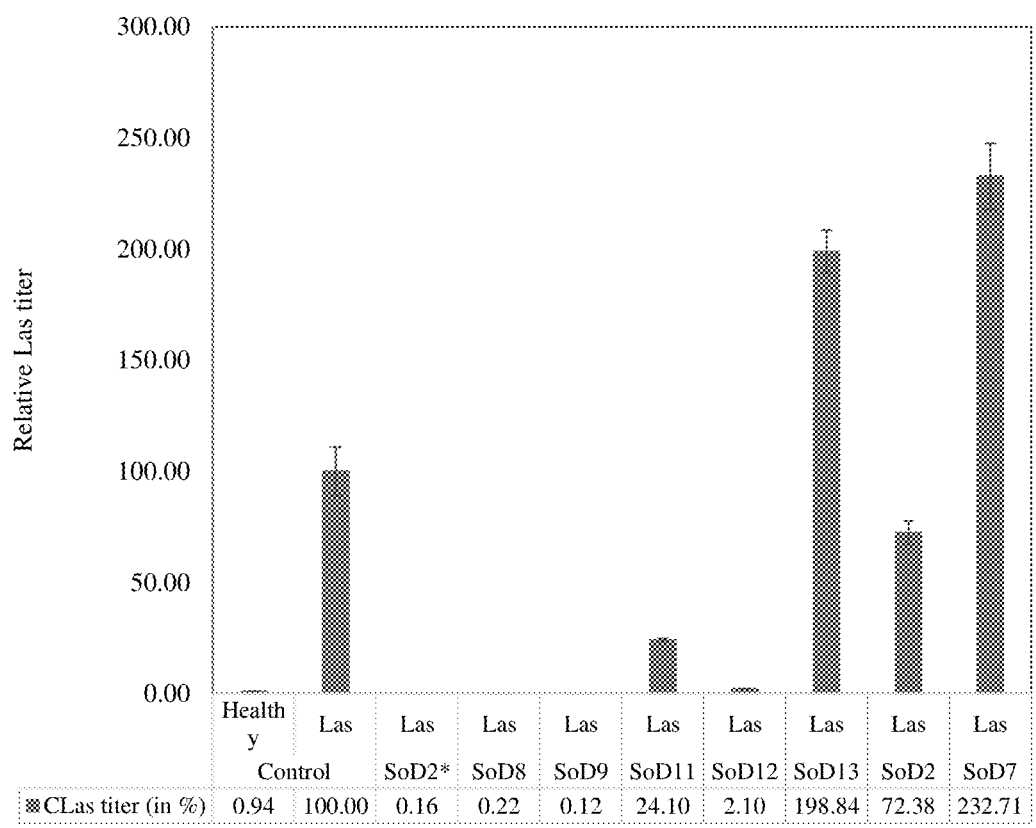
FIG. 20 provides a chart of the quantitation of Las titers in defensin-expressing hairy root cultures using qPCR analysis. Results are displayed as Las titers (in %) relative to the control-infected hairy roots (set as 100%). The "SOD" values in this figure relate to a set of synthetic spinach defensin genes that were co-transformed with the *Rhizobium rhizogenes* into the citrus hairy roots in this experiment.

Citrus hairy root cultures (healthy and CLas) were screened for GFP expression at 90 dpt (FIG. 19). Transformed roots were also collected for RNA and genomic DNA extraction for downstream molecular analysis. qPCR was performed to determine the Las titer in 90 dpt citrus hairy roots, using rplk04 (5'-GGATAGTCCTGTTAT-TGCTCCTAAA-3' (SEQ ID NO: 3)) and J5 (5'-ACAAAAGCAGAAATAGCACGAACAA-3' (SEQ ID NO: 4)) primer pair (for detection of Las) and citrus endogenous gene Glyceraldehyde-3-phosphate dehydrogenase C2 (GAPC2) (Mafra et al., 2012) endogenous reference gene primer pair for normalization of qPCR. The experiment was repeated independently, and similar trends persisted (FIG. 20).

Accordingly, the results of these experiments as presented in FIGS. 17-20 demonstrate successful cultivation of Lso/Las and hairy root transformation in different, unrelated plants, the potato and citrus, in addition to tomato, as described above.

Example 13: High Throughput System for Cultivating Fastidious Phytomicrobes and Evaluating Antimicrobials Plant, Insect Maintenance and Disease Challenges.

Potato (*Solanum tuberosum* L. var. Atlantic) and tomato (*Solanum lycopersicum* L. var. Lance) plants were propagated in soil (Sungrow 360) and maintained in a growth chamber at 21-22° C., with a 14-h/10-h light/dark photoperiod and 50% relative humidity. *Bactericera cockerelli* (Šulc) psyllid colonies that are CLso-positive (haplotype B, the most virulent and prevalent haplotype) or CLso-negative were collected in Texas[30], and maintained in the laboratory in nylon cages (Bugdorm, Taiwan). The presence and haplotype of *Candidatus* L. solanacearum (CLso) in psyllid colonies was periodically determined by PCR using primers specific for the single sequence repeat (SSR) loci of CLso (SSR-F and SSR-R (Table 1)[31]. For CLso infections, one-month-old potato or tomato plants were challenged with approximately twenty psyllids harboring CLso.

Plants were confirmed positive for CLso two weeks after challenge by PCR, as described in the molecular diagnostics section.

TABLE 1

| Primer Name | Sequence |
|---|---|
| At_NPR1-F | 5'-CCGAATTCGTATGGACACCACCATTGATGGA-3' |
| At_NPR1-R | 5'-CCGGATCCGTTCACCGACGACGATGAGAGA-3' |
| Sl_NPR1_F | 5'-CCGAATTCGTATGGATAGTAGAACTGCTTTTTCGG-3' |
| Sl_NPR1_R | 5'-CCGGATCCGTCTATTTCCTAAATGGGAGATTATTG-3' |
| St-NPR3-G1_F | 5'-ATTGGTCGTTGAGGGGATTGATGT-3' |
| St-NPR3-G1_R | 5'-AAACACATCAATCCCCTCAACGAC-3' |
| St-NPR3-FP1 | 5'-TTTGAACAATGGAGAGCGGC-3' |
| St-NPR3-RP1 | 5'-TAATTAATGGCAGGGCGGCA-3' |
| TEV5'-F | 5'-ACGAATCTCAAGCAATCAAGC-3' |
| TEV3'-R | 5'-CTCACTTTGTCGTTCGCCTA-3' |
| SSR-F | 5'-TTATTTTGAGATGGTTTGTTAAATG-3' |
| SSR-R | 5'-TATTATCATTCTATTGCCTATTTCG-3' |
| RPL2-F | 5'-GAGGGCGTACTGAGAAACCA-3' |
| RPL2-R | 5'-CTTTTGTCCAGGAGGTGCAT-3' |
| StRPL2-F | 5'-GTGGAGGACGAACTGAGAAA-3' |
| StRPL2-R | 5'-AGTCCTCCTTGCAGCAATAA-3' |
| GAPC2-F | 5'-GAGGAGATCCCATGGGCAAA-3' |
| GAPC2-R | 5'-AAGAGGAGCTAGGCAGTTGG-3' |
| Lso-F | 5'-CGAGCGCTTATTTTTAATAGGAGC-3' |
| HLB-R | 5'-GCGTTATCCCGTAGAAAAAGGTAG-3' |
| rplk04-F | 5'-GGATAGTCCTGTTATTGCTCCTAAA-3' |
| J5-R | 5'-ACAAAAGCAGAAATAGCACGAACAA-3' |

Microbial Hairy Root Culture Production, Transformation and Antimicrobial Assays.

Both ex vivo and an in planta approaches were evaluated to generate potato and tomato hairy root cultures using CLso-infected plant as inoculum. For the ex vivo approach, branches were excised from either healthy (unchallenged control) or CLso-infected plants 21 days post-challenge, and used inoculated using a fresh culture of *Rhizobium rhizogenes* (American Type Culture Collection strain 15834, OD:0.5), as described previously[22, 23, 24, 25] For the in planta approach, *R. rhizogenes* (OD:0.5) was inoculated directly into the stems of live plants using a syringe, stems then were wrapped with foil to maintain humidity in a growth chamber. For *Candidatus* L. asiaticus (CLas) hairy root production, CLas-positive material, confirmed positive by PCR, was collected from infected field-grown citrus (eureka lemon, orange, grapefruit) trees at the Texas A&M University-Kingsville Citrus Center, Weslaco, Tex. (26° 10'00.1"N 97° 57'27.7"W). Healthy citrus material was collected from greenhouse-grown trees, with no exposure to psyllids. The healthy and CLas-infected citrus materials were inoculated using ex vivo approaches, as described previously[22, 23, 24, 25]. Formation of hairy roots was confirmed by GFP visualization using fluorescence microscopy (Olympus). The hairy root transformation (TE) efficiency was calculated with the formula: number of GFP-positive roots/total number of roots*100. TE ranged from ~90-95% for potato/tomato and 50-70% for citrus, depending on the cultivar and age of the explants. Further confirmation of the hairy roots was obtained by PCR amplification of either GFP or rolB/rolC genes encoded on the binary and Ri T-DNA plasmids, respectively, and that are co-transformed in the hairy root cultures. The Solanaceae RPL2 and citrus GAPC2 endogenous genes were used as PCR control. The levels of CLso and CLas in the infected hairy root cultures were determined by the amplification of diagnostic markers specific to CLso (16S rDNA)[20], and CLas (rplk04/J5)[21], described further in the molecular diagnostics section.

For transformation of antimicrobial genes and CRISPR constructs in CLso+ potato hairy root cultures, binary vectors containing either AtNPR1-, SINPR1-, or StNPR3-CRISPR-Cas9 constructs and appropriate negative controls (empty vector/GFP alone) were co-transformed into *R. rhizogenes* and used for hairy root induction, as described above. About 30 days post transformation, hairy roots were visually screened for GFP under a fluorescence dissection microscope and GFP+ roots were sampled from controls and treatments for subsequent molecular diagnostics (described below). Three to five independent biological replicates, comprised of a mixture of randomly selected GFP+ hairy roots were collected, flash frozen in liquid nitrogen and stored at −80° C. until subsequent processing for molecular diagnostics. Theoretically, since each hairy root originates from an independently transformed cell, in a given experiment, the different biological replicates in theory represent hundreds of independent transformation events, thus reducing the insertion-specific artifacts or biases. All experiments were repeated twice at independent times in separate batches.

For small molecule bioassays, ~200 mg of CLso+ hairy root cultures were surface sterilized with 2% bleach, followed by five washes with sterile distilled water. The hairy roots were transferred into multi-titer plates containing MS medium with 1% sucrose. Specific concentration of the small molecules or DMSO as control (100 ppm) were added to the media, and plates were vacuum-infiltrated to allow penetration of the molecules into the hairy root tissues. Three to five biological replicates were performed for each treatment. All the cultures were incubated in the dark at 21° C. for 48 h on an end-on shaker at 60 rpm. Hairy root tissues were sampled after 48 h, flash frozen in liquid nitrogen and stored at −80° C. until subsequent processing for molecular diagnostics.

Plasmids, CRISPR Construct Design and Amplicon Sequencing.

To obtain the full-length NPR1 coding sequences, total RNA was extracted from 3-week-old *Arabidopsis* and tomato seedlings and used for cDNA synthesis with SuperScript III Reverse Transcriptase (Thermo Fisher Scientific, Waltham, Mass.), according to the manufacturer's instructions. The *Arabidopsis* NPR1 (1782 bp) (AT1G64280.1) and tomato NPR1 (1731 bp) coding sequences (Solyc07g040690.2.1) were amplified with Phusion DNA polymerase (New England BioLabs, Ipswich, Mass.) using cDNA as template and with primers containing the EcoRI restriction site at the 5' end of the forward primer and a BamHI site at the 3' end of the reverse primer (Table 1). The PCR products were digested with EcoRI/BamHI and cloned into a binary vector containing the GFP reporter gene (pBIN-mGFP-5ER) under the control of a double enhanced CaMV 35S promoter (DE35S-P) and a 35S terminator (35S-T). All the nucleotide sequences were confirmed by Sanger DNA sequencing before transformation into *R. rhizogenes* for hairy root production.

Figure 23:
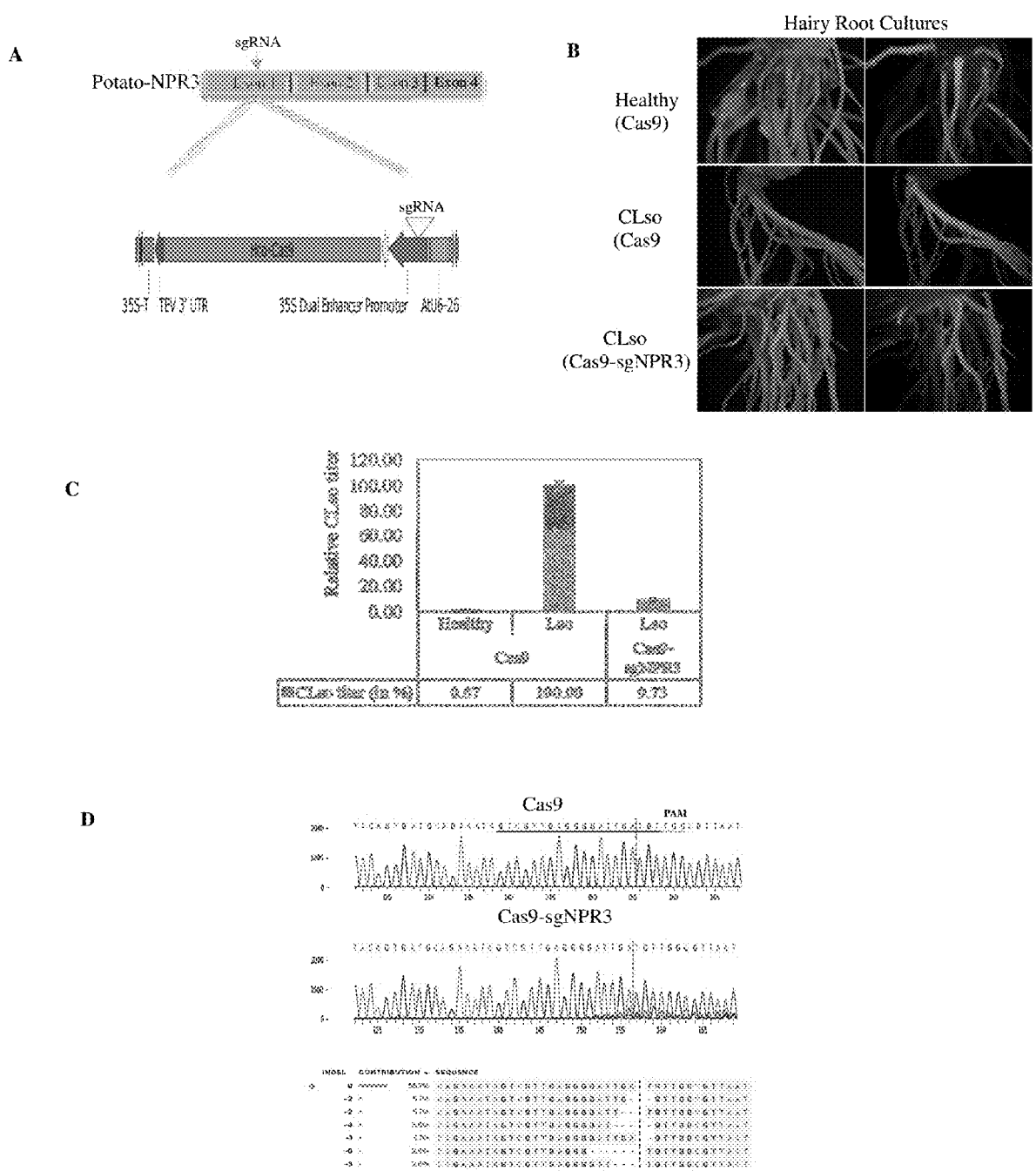
FIGS. 23A-D provide the results of testing of CRISPR-Cas9 mediated gene editing of disease susceptibility gene in CLso-potato hairy root cultures.
Figure 24:
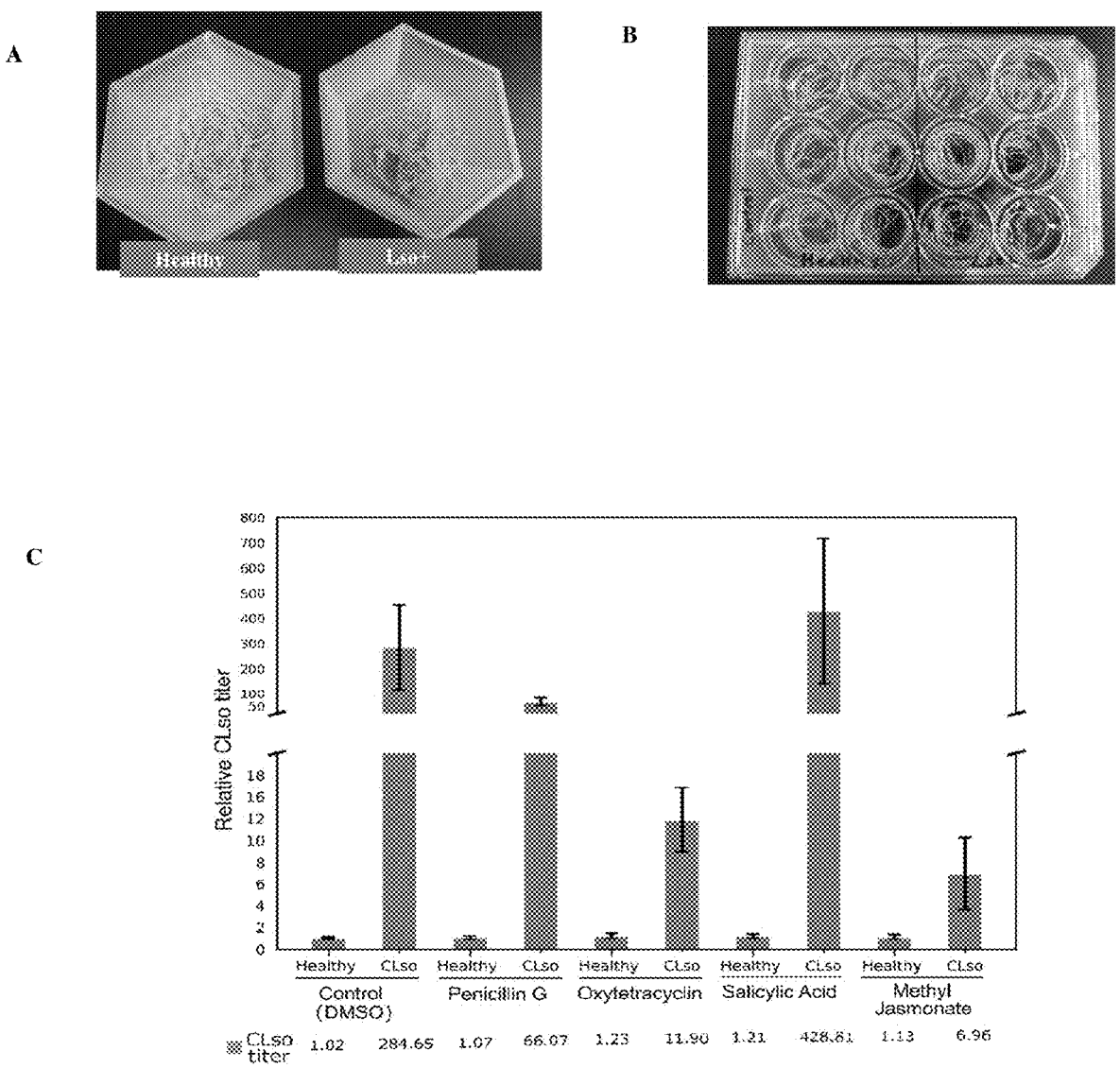
FIGS. 24A-C provide photos and data for small molecule screening in microbial hairy root cultures in vitro.
Figure 25:
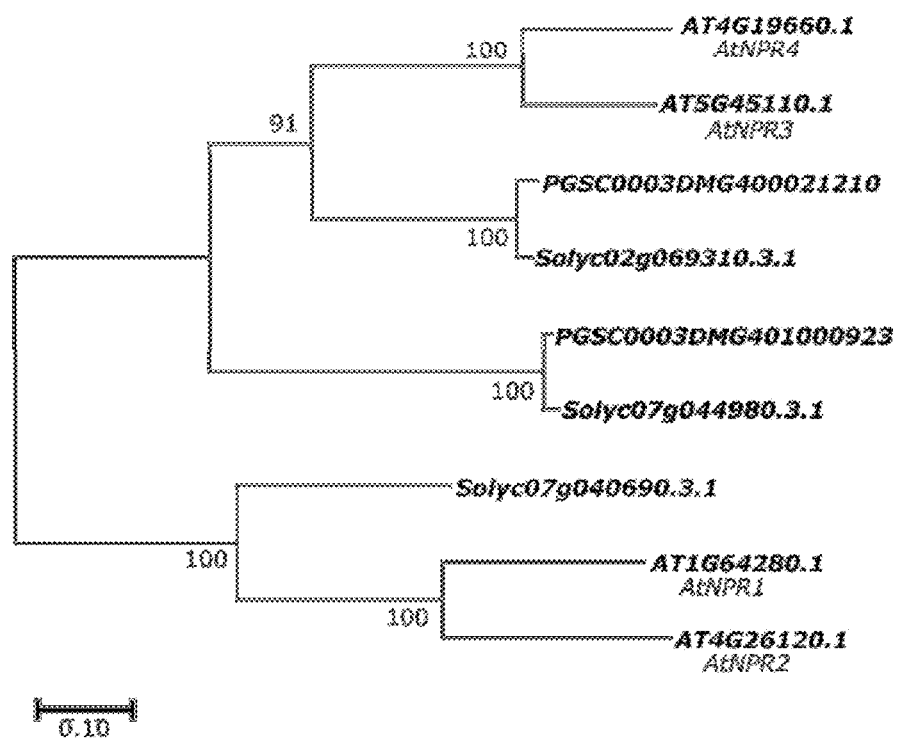
FIG. 25 provides phylogenetic analysis of *Arabidopsis*, tomato and potato Non-expressor of Pathogenesis Related gene (NPR) gene family. The phylogenetic tree was inferred using Maximum Likelihood method using amino-acid sequences of NPR-related members from *Arabidopsis*, potato and tomato. The tree is drawn to scale with branch lengths measured the number of substitutions per site. Bootstrap values are indicated by the numbers at the branch points.

For CRISPR experiments, multiple sgRNA targets were designed for the GFP and NPR3 gene sequences (PGSC0003DMG401000923) using the CRISPR-P design toolset[32]. Sequences of the top sgRNA hits are indicated in FIG. 23 and FIG. 25. The respective sgRNA targets were produced as synthetic oligos (Integrated DNA Technologies, Inc., Iowa, USA) with appropriate overhang sequences. Each pair of oligonucleotides were annealed and phosphorylated. The pChimera vector, containing the *Arabidopsis* U6-26 promoter[33] was linearized using BbsI, and the spacer was ligated between the two BbsI sites using annealed oligonucleotides. The customized RNA chimera was then sub-cloned into pBIN-HcoCas9:mGFP-5ER[34] to obtain a functional Cas9 expression construct for targeted mutagenesis. The Cas9 vector carrying sgNPR3 or the sgGFP spacer sequence and Cas9 alone were transferred independently into *R. rhizogenes* for hairy root production. For detection of indels in the transgenic hairy roots, 500 bp of the target region in NPR3 or GFP was amplified by PCR using gene-specific primers (Table 1) and Phusion Polymerase (New England BioLabs, Ipswich, Mass.). PCR amplicons were cleaned up using DNA PCR cleanup kits (Zymo Research, Irvine, Calif.), and sequenced by Sanger sequencing (Eton Bioscience, Inc, San Diego, Calif.). The percentage of indels in transgenic hairy roots was analyzed by Inference of CRISPR Edits (ICE) tool[35].

Nucleic Acid Isolation, PCR and RT-PCR Diagnostics.

To confirm the transgene expression in the transformed hairy roots, total RNA was isolated using the Direct-zol RNA MiniPrep Plus kit (Zymo Research, Irvine, Calif.) according to manufacturer's instructions and subjected to reverse-transcription (RT)-PCR. First-strand cDNAs were synthesized from 2.0 µg total RNA using the Superscript™ III First-Strand Synthesis System (ThermoFisher Scientific, Grand Island, N.Y.), following the manufacturer's instructions. Subsequently, PCR was performed on a C1000TM thermal cycler (BioRad Laboratories, Hercules, Calif.) to validate gene expression in the hairy root cultures. The tomato and potato RIBOSOMAL PROTEIN L2 (RPL2) and the citrus GLYCERALDEHYDE-3-PHOSPHATE DEHYDROGENASE C2 (GAPC2) genes were used as endogenous reference genes for normalization and relative expression estimation. Primer pairs used are provided in Table 1 and as follows: the 5' and 3' untranslated regions (UTR) of Tomato Etch Virus (TEV) flanking the NPR1 genes (TEV-F and TEV-R), tomato RPL2 (RPL-F and RPL-R);[36], potato RPL2 (StRPL-F and StRPL-R) and citrus GAPC2 (GAPC2-F and GAPC2-R)[37].

To determine the effects of small-molecules, transgenes and CRISPR-Cas9 constructs on the CLso and CLas titers within the hairy root cultures, quantitative (q)PCR analysis was performed using DNA isolated from the various samples. Total Citrus hairy roots DNA was isolated according to Almeyda et al (2001)[38] from ~200 mg of tissue homogenized using Precellys 24 homogenizer (MO BIO Laboratories, Carlsbad, Calif., USA). The quality and quantity of DNA was determined using a NanoDrop 1000 Spectrophotometer (Thermo Fisher Scientific, Wilmington, Del., USA), and by agarose gel electrophoresis. Approximately 50 ng of total DNA was used for qPCR analysis, performed on a CFX384™ Real-Time PCR Detection System (Bio-Rad Laboratories, Inc., Hercules, Calif., USA) using iTaq™ universal SYBR® Green supermix (Bio-Rad Laboratories, Inc.), following the manufacturer's instructions. The 16s rDNA Lso-F and HLB-R primers were used for CLso detection[20], while rplk04-F and J5-R primers were used for CLas detection[21] (Table 1). A dissociation melting curve analysis was performed and showed no non-specific amplification or primer-dimers. For the antimicrobial treatments, relative CLso titers were estimated using the DDCt method[39]. The CLso Ct values were normalized to RPL2 to correct for DNA template concentration differences among the samples and were plotted relative to the control CLso hairy root samples (DMSO treated), which was set to 100%. A Student's t-test was used to determine statistically significant ($P<0.05$) differences among controls and treatments.

Figure 21:
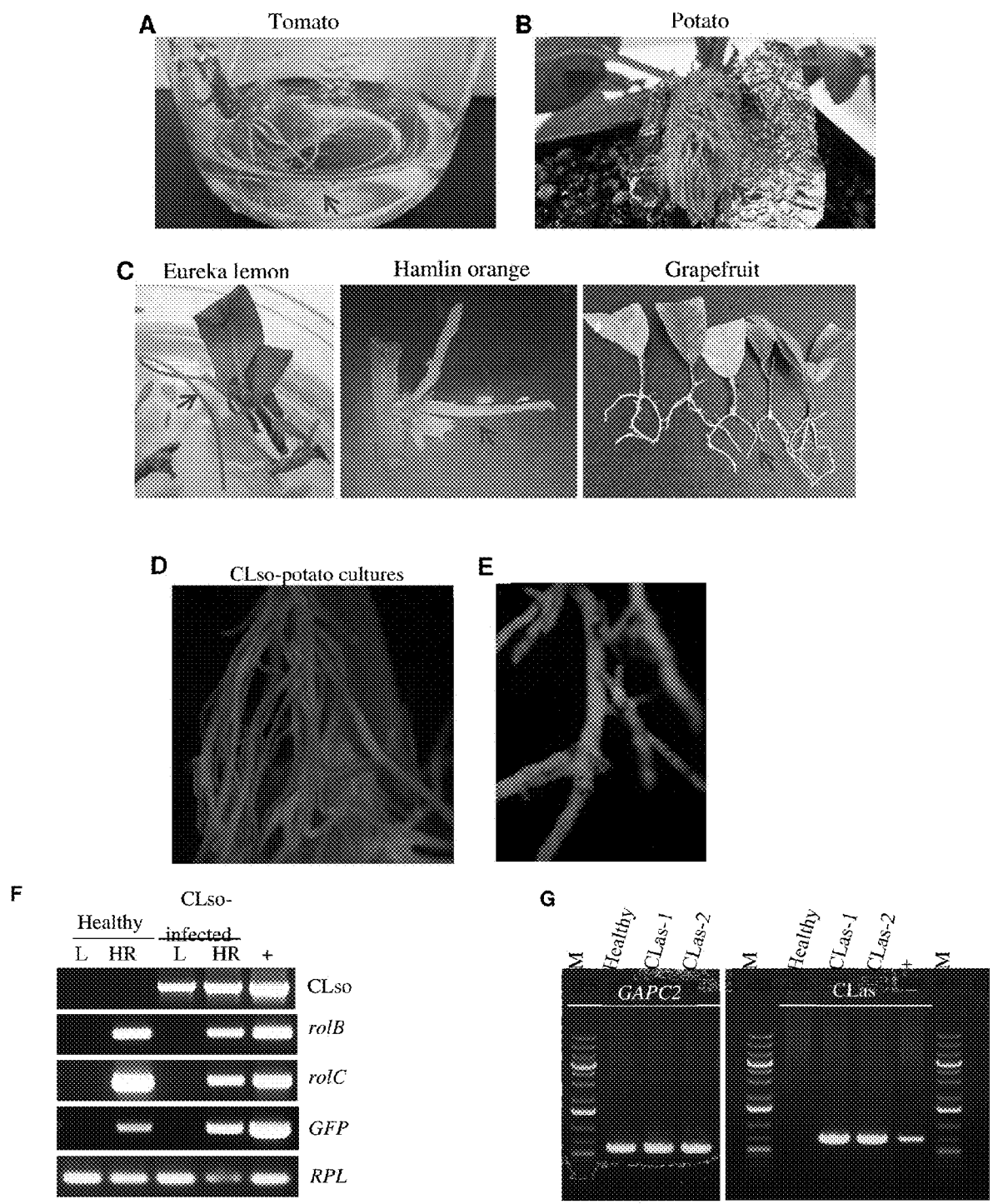
FIGS. 21A-G relate to Ex-vivo and in planta culturing of *Candidatus* Liberibacter solanacearum (CLso) and asiaticus (CLas) in tomato, potato and citrus hairy roots.

Hairy root cultures were generated from CLso- and CLas-infected potato, tomato and citrus explant sources (FIG. 21A-C). A binary T-DNA vector containing a GFP cassette was co-transformed into the hairy root cultures to help in screening and distinguishing hairy roots from adventitious roots. Fluorescence microscopy and PCR diagnostics confirmed the authenticity of the hairy root cultures, indicated by the presence of GFP-expressing hairy roots. A transformation efficiency (TE) of ~90-95% was achieved (TE=number of GFP-positive roots/total number of roots*100) for potato and tomato, and 50-70% TE for citrus (FIG. 21D-E). Additionally, PCR amplification of rolB and rolC, genetic markers of hairy roots encoded on the Ri T-DNA of R. *Rhizogenes*, and of the GFP gene encoded on the binary vector co-transformed in the hairy roots was used to distinguish hairy roots from adventitious roots (FIG. 21D). CLso and CLas was detected in the infected hairy root cultures, but not in the healthy hairy roots, upon PCR amplification using diagnostic markers specific to CLso (16S rDNA)[70], and CLas (rplk04/J5)[21] (FIG. 21E-F). These experiments demonstrate that in a manner similar to normal plant roots, ex vivo produced hairy root cultures and their vasculature can sustain growth of fastidious microbes.

Figure 22:
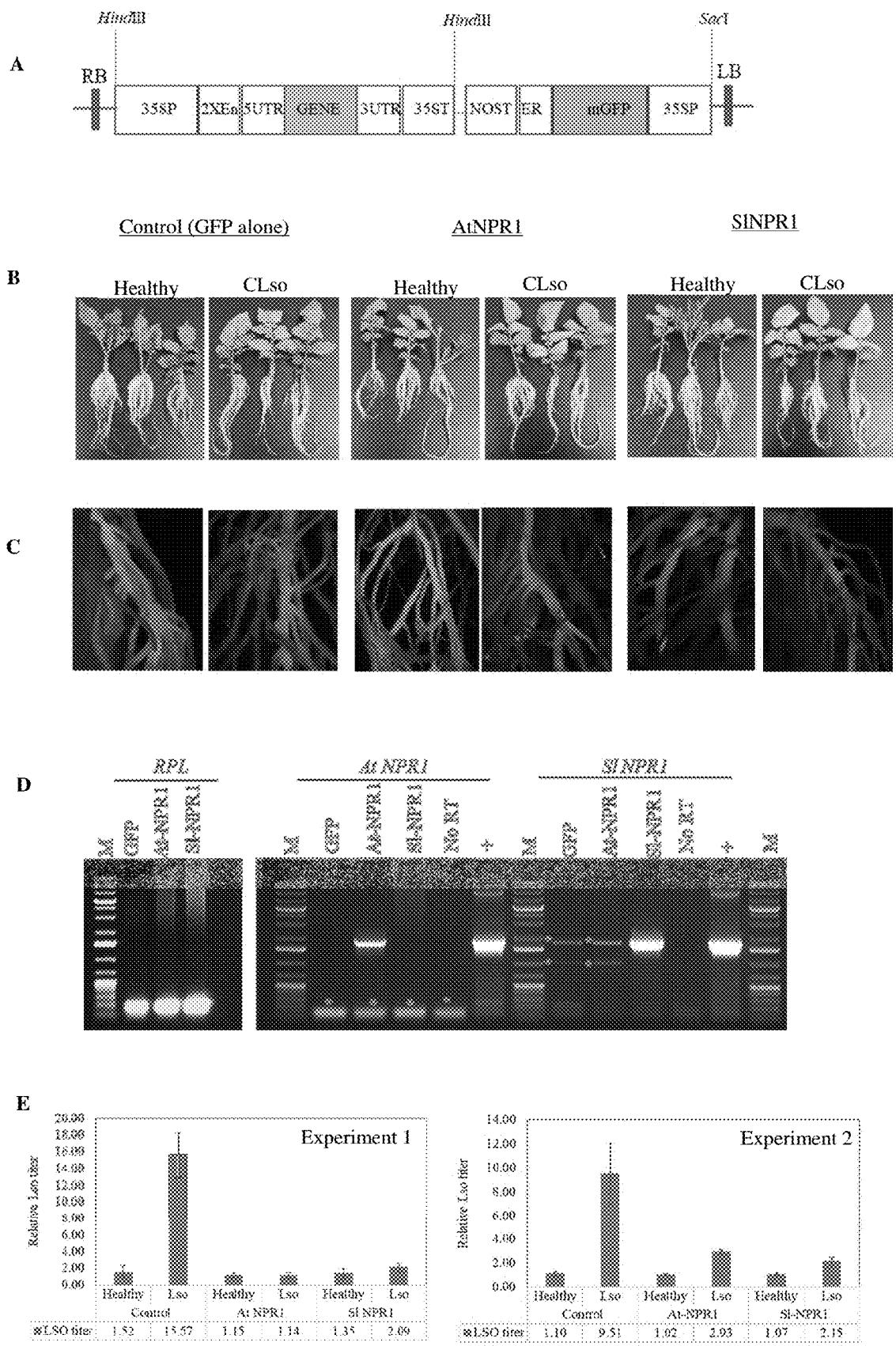
FIGS. 22A-E provide the results of transgene overexpression and disease resistance gene testing in the *Candidatus* Liberibacter solanaceaum (CLso)-potato hairy root cultures.

The microbial hairy root cultures were leveraged and bioassays for high throughput antimicrobial screening were established. For this, the experiments focused on using the CLso-potato hairy root cultures. First, the inventors evaluated the ability to screen disease resistance genes in the CLso-potato hairy root cultures. A broad-spectrum disease resistance gene, NPR1, from *Arabidopsis* (AtNPR1) and tomato (SlNPR1) was identified by phylogenetic analysis (FIG. 25) and cloned into binary vectors, containing a GFP reporter gene (FIG. 22A). The NPR1 gene construct and an empty vector, containing the GFP, were co-transformed into healthy (unchallenged) or CLso+ hairy root cultures using *R. rhizogenes*, as described previously (FIG. 22B)[22, 23, 24, 25]. Molecular diagnostics was performed at 30 days after transformation to confirm presence of GFP and NPR1 expression in the hairy root cultures (FIG. 22C), followed by qPCR-based estimation of CLso titers. Consistent with the antimicrobial role of NPR1 against other microbes, overexpression of either *Arabidopsis* or tomato NPR1 significantly lowered CLso titers in the hairy root cultures, when compared to empty vector transformed hairy root cultures (FIG. 22D).

The experiment was repeated independently twice, and similar results were obtained (FIG. 22D).

While NPR1 promotes plant defense, its homologs NPR3 and NPR4 function antagonistically to suppress plant defenses in *Arabidopsis*[26]. It is possible that reduction of NPR3 activity in potato could enhance tolerance to CLso. To test this hypothesis and demonstrate the utility of microbial hairy root cultures to edit endogenous genes, the inventors identified the potato ortholog of AtNPR3 (StNPR3) and performed CRISPR-Cas9-mediated editing of StNPR3 in the CLso-hairy root cultures. Cas9 alone (control) or Cas9-sgNPR3, were co-transformed into healthy or CLso containing hairy root cultures (FIG. 24). Amplicon sequencing of the target site, followed by reverse-transcription (RT) qPCR performed on edited roots confirmed successful editing and loss of expression of S/NPR3 in Cas9-sgNPR3 hairy root cultures, but not in Cas9 alone cultures. After 30 days post-transformation, CLso levels were estimated by qPCR. The results revealed significant reduction in CLso titers in Cas9-sgNPR3 hairy root cultures, when compared to the controls (Cas9 alone), suggesting the NPR3 acts as suppressor of defenses in potato, and its function is conserved between potato and *Arabidopsis.*

To further demonstrate the feasibility of gene editing a transgene, the inventors edited a GFP that is stably expressed in transgenic potato. In this experiment, the loss of GFP fluorescence, and presence of indels at the target site when transformed with Cas9-sgGFP, but not with Cas9 alone, indicated successful editing of GFP in healthy and CLso hairy root cultures (FIG. 26C-F). As expected, unlike StNPR3 editing, GFP editing had no effect on CLso levels in the hairy root cultures (FIG. 26B), underscoring the specific activity of StNPR3. Together, these experiments show the robustness of the microbial hairy root cultures to evaluate efficacy of candidate resistance and susceptibility factors much faster (~1 month), when compared to conventional stable transformations and mature plant assays (~4-6 months).

To determine whether small-molecule therapies can be evaluated using the CLso hairy root cultures, the inventors tested the efficacy of multiple antibiotics (penicillin and oxytetracycline) and plant immune modulators (salicylic acid and jasmonic acid/methyl-JA) routinely used to promote tolerance against microbes. Briefly, CLso hairy root cultures were treated with the different antimicrobials and incubated for 48 hours, followed by determination of CLso levels by qPCR. Relative to the control (DMSO, 100 ppm), penicillin and oxytetracycline (100 ppm) significantly suppressed CLso titers (FIG. 24). Among the immune modulators tested, methyl-JA (10 μM) suppressed CLso, however salicylic acid (SA, 100 μM) had no significant effect. Recently, it was reported that *Candidatus* Liberibacter spp. encodes a salicylic acid hydroxylase (SahA) enzyme that could degrade salicylic acid to suppress plant defenses[27]. Furthermore, overexpression of CLas SahA in transgenic *N. benthamiana* abolished SA levels and hypersensitive response. The CLso and CLas SahA amino acid sequences are very similar, with ~68% identity with each other[27]. Based on the observed results in the microbial hairy root bioassays, it is possible that CLso SahA may have a role in rendering the SA ineffective in potato, thus allowing CLso to thrive in the hairy roots treated with SA. Regardless of the underlying mechanisms, the observed lack of effectiveness of SA in the hairy root bioassay, in comparison to the other small molecules, provides specificity to the bioassay.

Example 14: Efficacy Testing of a Biological in Microbial Hairy Root Cultures

Biologicals or microbial-biological control agents can be very effective in controlling plant diseases. These agents may function directly by antagonizing the microbes via. hyperparasitism, antibiosis or competition for nutrients in the growth conditions for the pathogen[40]. Other biologicals can also induce indirect resistance or priming of plant defenses in a manner similar to immune modulators. Here, we tested if the efficacy of a biological (B1) can be evaluated in microbial hairy root cultures (CLso). The assay was performed in vitro as described previously for the bactericides/immune modulators, with five biological replicates for each treatment. Three different concentrations (ND—no dilution, 1:10 and 1:50 dilution) of B1 were treated for 2 days and 5 days along with untreated controls. Levels of CLso were determined by conventional PCR using DNA extracted from the CLso-potato hairy root cultures after treatments. The results demonstrate a clear dose-dependent antimicrobial activity of B1 against CLso, observed by a reduction in CLso levels in treated versus untreated samples in 2- and 5-days treatment (FIG. 27). The inhibition was on par or better than conventional bactericides (penicillin and oxytetracycline). These results successfully demonstrated the utility of microbial hairy root culture system for in vitro evaluation of biologicals.

REFERENCES

1. Haapalainen M. Biology and epidemics of *Candidatus* Liberibacter species, psyllid-transmitted plant-pathogenic bacteria. *Annal Applied Biol* 165, 172-198 (2014).
2. CNAS. Economic impacts of zebra chip on the Texas potato industry. Center for North American Studies (2006).
3. Hodges A W, Spreen T H. Economic Impacts of Citrus Greening (HLB) in Florida, 2006/07-2010/111. The Institute of Food and Agricultural Sciences (2012).
4. Lin H, et al. The complete genome sequence of '*Candidatus* Liberibacter solanacearum', the bacterium associated with potato zebra chip disease. *PLoS One* 6, e19135 (2011).
5. Hartung J S, Shao J, Kuykendall L D. Comparison of the 'Ca. Liberibacter asiaticus' genome adapted for an intracellular lifestyle with other members of the Rhizobiales. *PloS one* 6, e23289 (2011).
6. Fagen J R, et al. Comparative genomics of cultured and uncultured strains suggests genes essential for free-living growth of Liberibacter. *PLoS One* 9, e84469 (2014).
7. Wang J, et al. Genomic sequence of '*Candidatus* Liberibacter solanacearum' haplotype C and its comparison with haplotype A and B genomes. *PloS one* 12, e0171531 (2017).
8. Pham V H T, Kim J. Cultivation of unculturable soil bacteria. *Trends Biotechnol* 30, 475-484 (2012).
9. Janssen P H. New cultivation strategies for terrestrial microorganisms. (edˆ(eds). ASM Press (2008).
10. Davis K E R, Joseph S J, Janssen P H. Effects of Growth Medium, Inoculum Size, and Incubation Time on Culturability and Isolation of Soil Bacteria. *Appl Environ Microbiol* 71, 826-834 (2005).

11. Kaeberlein T, Lewis K, Epstein S S. Isolating "Uncultivable" Microorganisms in Pure Culture in a Simulated Natural Environment. *Science* 296, 1127-1129 (2002).
12. Nichols D, et al. Use of Ichip for High-Throughput In Situ Cultivation of "Uncultivable" Microbial Species. *Appl Environ Microbiol* 76, 2445-2450 (2010).
13. Molki B, et al. pH and Oxygen Microenvironments in Asian Citrus Psyllid. In: *The 5th International Research Conference on Huanglongbing*. (ed^(eds) (2017).
14. Bernert A, Jain M, Munoz-Bodnar A, Davis M, Gabriel D W. Assessment of growth media requirements for Liberibacters and making L. crescens more Las-like. In: *The 5th International Research Conference on Huanglongbing* (ed^(eds) (2017).
15. Ono N N, Tian L. The multiplicity of hairy root cultures: Prolific possibilities. *Plant Sci* 180, 439-446 (2011).
16. Ron M, et al. Hairy Root Transformation Using *Agrobacterium rhizogenes* as a Tool for Exploring Cell Type-Specific Gene Expression and Function Using Tomato as a Model. *Plant Physiol* 166, 455-469 (2014).
17. Young J M, Kuykendall L D, Martinez-Romero E, Kerr A, Sawada H. A revision of *Rhizobium* Frank 1889, with an emended description of the genus, and the inclusion of all species of *Agrobacterium* Conn 1942 and *Allorhizobium undicola* de Lajudie et al. 1998 as new combinations: *Rhizobium radiobacter, R. rhizogenes, R. rubi, R. undicola* and *R. vitis. Int J Syst Evol Microbiol* 51, 89-103 (2001).
18. Ron M. et al. Identification of Novel Loci Regulating Interspecific Variation in Root Morphology and Cellular Development in Tomato. *Plant Physiol* 162, 755-768 (2013).
19. Lucas M, et al. SHORT-ROOT Regulates Primary, Lateral, and Adventitious Root Development in *Arabidopsis. Plant Physiol* 155, 384-398 (2011).
20. Levy J. Ravindran A, Gross D, Tamborindeguy C, Pierson E. Translocation of '*Candidatus* Liberibacter solanacearum', the Zebra Chip Pathogen, in Potato and Tomato. *Phytopathology* 101, 1285-1291 (2011).
21. Hocquellet A, Toorawa P, Bove J-M, Gamier M. Detection and identification of the two *Candidatus* Liberobacter species associated with citrus huanglongbing by PCR amplification of ribosomal protein genes of the β operon. *Mol Cell Probes* 13, 373-379 (1999).
22. Mandadi K K, Irigoven S C, Mirkov T E. Methods, compositions, and systems for culturing and characterizing fastidious plant microbes (2016).
23. Crane C, Wright E, Dixon R A, Wang Z-Y. Transgenic *Medicago truncatula* plants obtained from *Agrobacterium tumefaciens*-transformed roots and *Agrobacterium rhizogenes*-transformed hairy roots. *Planta* 223, 1344-1354 (2006).
24. Alagarsamy K, Shamala L F, Wei S. Protocol: high-efficiency in-planta *Agrobacterium*-mediated transgenic hairy root induction of *Camellia sinensis* var. *sinensis. Plant methods* 14, 17 (2018).
25. Khandual S, Reddy P M. Rapid, Efficient and High-Performance Protocol for *Agrobacterium rhizogenes*-Mediated Hairy Root Transformation of the Common Bean *Phaseolus vulgaris. Advances in Bioscience and Biotechnology* 5, 333 (2014).
26. Ding Y, et al. Opposite roles of salicylic acid receptors NPR1 and NPR3/NPR4 in transcriptional regulation of plant immunity. *Cell* 173, 1454-1467. e1415 (2018).
27. Li J, et al. '*Candidatus* Liberibacter asiaticus' encodes a functional salicylic acid (SA) Hydroxylase that degrades SA to suppress plant defenses. *Mol Plant-Microbe Interact* 30, 620-630 (2017).
28. Davis M J, Mondal S N, Chen H, Rogers M E, Brlansky R H. Co-cultivation of '*Candidatus* Liberibacter asiaticus' with Actinobacteria from Citrus with Huanglongbing. *Plant Dis* 92, 1547-1550 (2008).
29. Leonard M T, Fagen J R, Davis-Richardson A G, Davis M J, Triplett E W. Complete genome sequence of Liberibacter crescens BT-1. *Stand genomic sci* 7, 271 (2012).
30. Sengoda V G, Cooper W R, Swisher K D, Henne D C, Munyaneza J E. Latent Period and Transmission of "*Candidatus* Liberibacter solanacearum" by the Potato Psyllid *Bactericera cockerelli* (Hemiptera: Triozidae). *PLoS ONE* 9, e93475 (2014).
31. Lin H, et al. Genetic diversity of 'Cadidatus Liberibacter solanacearum'strains in the United States and Mexico revealed by simple sequence repeat markers. *Eur J Plant Pathol* 132, 297-308 (2012).
32. Lei Y, Lu L, Liu H-Y, Li S, Xing F, Chen L-L. CRISPR-P: a web tool for synthetic single-guide RNA design of CRISPR-system in plants. *Molecular plant* 7, 1494-1496 (2014).
33. Fauser F, Schiml S, Puchta H. Both CRISPR/C as-based nucleases and nickases can be used efficiently for genome engineering in A rabidopsis *thaliana. The Plant Journal* 79, 348-359 (2014).
34. Cody W B, Scholthof H B, Mirkov T E. Multiplexed gene editing and protein overexpression using a tobacco mosaic virus viral vector. *Plant Physiol* 175, 23-35 (2017).
35. Hsiau T, et al. Inference of crispr edits from sanger trace data. *BioRxiv*, 251082 (2018).
36. Avila C A. et al. Loss of function of FATTY ACID DESATURASE7 in tomato enhances basal aphid resistance in a salicylate-dependent manner. *Plant Physiol* 158, 2028-2041 (2012).
37. Mafra V, et al. Reference Genes for Accurate Transcript Normalization in Citrus Genotypes under Different Experimental Conditions. *PLoS ONE* 7, e31263 (2012).
38. Almeyda León I H, Rocha Peña M A, Piña Razo J, Martinez Soriano J P. The use of polymerase chain reaction and molecular hybridization for detection of phytoplasmas in different plant species in México. *Revista Mexicana de fitopatologia* 19, (2001).
39. Livak K J, Schmittgen T D. Analysis of relative gene expression data using real-time quantitative PCR and the $2^{-\Delta\Delta CT}$ method. *Methods* 25, 402-408 (2001).
40. (Köhl, J., Kolnaar, R., and Ravensberg, W. J. (2019). Mode of Action of Microbial Biological Control Agents against Plant Diseases: Relevance Beyond Efficacy. *Frontiers in Plant Science* 10, 845)

The invention claimed is:

1. A method for assessing an effect of a test composition on a plant microbe selected from the group consisting of *Xylella fastidiosa* spp. and *Candidatus* Liberibacter spp., the method comprising:

(a) contacting a plant with the plant microbe to colonize the plant with the microbe;

(b) selecting tissues from one or more parts of the plant colonized with the plant microbe form step (a) as an explant source to create an explant;

(c) manually contacting the explant colonized by the plant microbe with a suspension of *Rhizobium rhizogenes* under conditions that permit induction of hairy roots to form a colonized hairy root; and (4) propagating the colonized hairy root to form a propagated hairy root; and contacting the propagated hairy roots with the test composition; and (5) assessing at least one metric of the presence or vitality of the plant microbe.

2. The method according to claim 1, wherein the plant is selected from a tomato plant, a potato plant, and a citrus plant.

3. The method according to claim 1, wherein the *Candidatus* Liberibacter spp. is selected from the group consisting of *Candidatus* Liberibacter solanacearum (Lso) and *Candidatus* Liberibacter asiaticus (Las).

4. The method according to claim 1, wherein the test composition is conditionally or constitutively present in the infected plant.

5. The method according to claim 1, wherein the plant colonized by the plant microbe comprises at least one of an exogenous transgene, a CRISPR/Cas, a TALEN, and an RNAi construct, and wherein the test composition is or comprises, respectively, a gene product of the transgene, the CRISPR/Cas, the TALEN, and the RNAi construct.

6. The method according to claim 1, wherein the plant comprises a first exogenous transgene and a second exogenous transgene.

7. The method according to claim 6, wherein the first exogenous transgene encodes an auto-fluorescent protein.

8. The method according to claim 1, further comprising confirming the presence of the plant microbe in the hairy roots by performing PCR amplification of a 16S rDNA marker gene of the plant microbe.

9. The method according to claim 1, wherein contacting the explant colonized by the plant microbe with the suspension of *Rhizobium rhizogenes* further comprises:

removing a photosynthetic portion of the explant to generate a wound site;

covering the wound site with a rock wool matrix; and exposing the rock wool matrix to the suspension of *Rhizobium rhizogenes*.

10. The method according to claim 1, wherein contacting the explant colonized by the plant microbe with the suspension of *Rhizobium rhizogenes* further comprises:

removing a photosynthetic portion of the explant to generate a wound site;

submerging the wound site in the suspension of *Rhizobium rhizogenes;* vacuum infiltrating at least a portion of the suspension of *Rhizobium rhizogenes* into the wound site; and covering the wound site with a vermiculite matrix.

11. The method according to claim 1 further comprising assessing the presence of the plant microbe in the propagated hairy root using polymerase chain reaction (PCR) amplification of a marker gene.

12. The method according to claim 1, wherein propagating the colonized hairy root to form a propagated hairy root further comprises:

exposing an attached hairy root or a harvested hairy root to one or more selective conditions;

transferring the attached hairy root or the harvested hairy root to at least one of:

a vermiculite matrix, a hydroponic system, an in vitro system, and a bioreactor system.

13. The method according to claim 1, wherein *Rhizobium rhizogenes* comprises both a Ri-DNA plasmid and a T-DNA plasmid, and wherein the T-DNA plasmid comprises a first exogenous transgene.

14. A method for assessing an effect of a test composition on a plant microbe, wherein the plant microbe is selected from the group consisting of *Xylella fastidiosa* spp. and *Candidatus* Liberibacter spp., the method comprising:

(a) selecting a tissue from one or more parts of a plant as an explant source to make an explant;

(b) manually contacting the explant with a suspension of *Rhizobium rhizogenes* under conditions that permit induction of hairy roots to form a hairy root on the explant;

(c) propagating the hairy root to form a propagated hairy root; and (d) manually contacting the propagated hairy root with plant microbe to form a microbe colonized hairy root;

(e) contacting the microbe colonized hairy roots with the test composition; and (f) assessing at least one metric of the presence or vitality of the plant microbe.

15. The method according to claim 14, wherein the plant is selected from a tomato plant, a potato plant, and a citrus plant.

16. The method according to claim 1, wherein the *Candidatus* Liberibacter spp. is selected from the group consisting of *Candidatus* Liberibacter solanacearum (Lso) and *Candidatus* Liberibacter asiaticus (Las).

* * * * *

SEQUENCE LISTING

<160> NUMBER OF SEQ ID NOS: 43

<210> SEQ ID NO 1
<211> LENGTH: 24

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgagcgctta tttttaatag gagc                                          24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcgttatccc gtagaaaaag gtag                                          24

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggatagtcct gttattgctc ctaaa                                         25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
acaaaagcag aaatagcacg aacaa                                         25

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccgaattcgt atggacacca ccattgatgg a                                  31

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccggatccgt tcaccgacga cgatgagaga                                    30

<210> SEQ ID NO 7
<211> LENGTH: 35
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 7
ccgaattcgt atggatagta gaactgcttt ttcgg                            35

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccggatccgt ctatttccta aatgggagat tattg                            35

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
attggtcgtt gagggggattg atgt                                       24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aaacacatca atcccctcaa cgac                                        24

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tttgaacaat ggagagcggc                                             20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
taattaatgg cagggcggca                                             20

<210> SEQ ID NO 13
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 13
acgaatctca agcaatcaag c                                               21

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctcactttgt cgttcgccta                                                 20

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ttattttgag atggtttgtt aaatg                                           25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tattatcatt ctattgccta tttcg                                           25

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gagggcgtac tgagaaacca                                                 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cttttgtcca ggaggtgcat                                                 20

<210> SEQ ID NO 19
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 19
gtggaggacg aactgagaaa                                                    20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
agtcctcctt gcagcaataa                                                    20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gaggagatcc catgggcaaa                                                    20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aagaggagct aggcagttgg                                                    20

<210> SEQ ID NO 23
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tacagtgatg cagaaatagt cgttgagggg attgatgttg gcgttaat                     48

<210> SEQ ID NO 24
<211> LENGTH: 38
<212> TYPE: DNA
<213> ORGANISM: Unknown
<220> FEATURE:
<223> OTHER INFORMATION: Description of Unknown:
      Potato hairy root sequence

<400> SEQUENCE: 24
cagaaatagt cgttgagggg attgatgttg gcgttaat                                38

<210> SEQ ID NO 25
<211> LENGTH: 36
<212> TYPE: DNA
<213> ORGANISM: Unknown
<220> FEATURE:
<223> OTHER INFORMATION: Description of Unknown:
```

-continued

Potato hairy root sequence

<400> SEQUENCE: 25
cagaaatagt cgttgagggg attggttggc gttaat                              36

<210> SEQ ID NO 26
<211> LENGTH: 36
<212> TYPE: DNA
<213> ORGANISM: Unknown
<220> FEATURE:
<223> OTHER INFORMATION: Description of Unknown:
      Potato hairy root sequence

<400> SEQUENCE: 26
cagaaatagt cgttgagggg atttgttggc gttaat                              36

<210> SEQ ID NO 27
<211> LENGTH: 34
<212> TYPE: DNA
<213> ORGANISM: Unknown
<220> FEATURE:
<223> OTHER INFORMATION: Description of Unknown:
      Potato hairy root sequence

<400> SEQUENCE: 27
cagaaatagt cgttgagggg atgttggcgt taat                                34

<210> SEQ ID NO 28
<211> LENGTH: 37
<212> TYPE: DNA
<213> ORGANISM: Unknown
<220> FEATURE:
<223> OTHER INFORMATION: Description of Unknown:
      Potato hairy root sequence

<400> SEQUENCE: 28
cagaaatagt cgttgagggg attgagttgg cgttaat                             37

<210> SEQ ID NO 29
<211> LENGTH: 32
<212> TYPE: DNA
<213> ORGANISM: Unknown
<220> FEATURE:
<223> OTHER INFORMATION: Description of Unknown:
      Potato hairy root sequence

<400> SEQUENCE: 29
cagaaatagt cgttgagggt gttggcgtta at                                  32

<210> SEQ ID NO 30
<211> LENGTH: 35
<212> TYPE: DNA
<213> ORGANISM: Unknown
<220> FEATURE:
<223> OTHER INFORMATION: Description of Unknown:
      Potato hairy root sequence

<400> SEQUENCE: 30
cagaaatagt cgttgagggg attgttggcg ttaat                               35

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 31
gatacccaga tcatatgaag cgg                                           23

<210> SEQ ID NO 32
<211> LENGTH: 66
<212> TYPE: DNA
<213> ORGANISM: Unknown
<220> FEATURE:
<223> OTHER INFORMATION: Description of Unknown:
      Potato hairy root sequence

<400> SEQUENCE: 32
gtgttcaatg cttttcaaga tacccagatc atatgaagcg gcacgacttc ttcaagagcg    60
ccatgc                                                              66

<210> SEQ ID NO 33
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gtgttcaatg cttttcaaga tacccagatc atatggaccg cctcttcttc aacgcccccc    60
ccgggg                                                              66

<210> SEQ ID NO 34
<211> LENGTH: 55
<212> TYPE: DNA
<213> ORGANISM: Unknown
<220> FEATURE:
<223> OTHER INFORMATION: Description of Unknown:
      Potato hairy root sequence

<400> SEQUENCE: 34
cttttcaaga tacccagatc atatgaagcg gcacgacttc ttcaagagcg ccatg         55

<210> SEQ ID NO 35
<211> LENGTH: 49
<212> TYPE: DNA
<213> ORGANISM: Unknown
<220> FEATURE:
<223> OTHER INFORMATION: Description of Unknown:
      Potato hairy root sequence

<400> SEQUENCE: 35
cttttcaaga tacccagatc atatgcacga cttcttcaag agcgccatg                49

<210> SEQ ID NO 36
<211> LENGTH: 51
<212> TYPE: DNA
<213> ORGANISM: Unknown
<220> FEATURE:
<223> OTHER INFORMATION: Description of Unknown:
      Potato hairy root sequence

<400> SEQUENCE: 36
cttttcaaga tacccagatc aaagcggcac gacttcttca agagcgccat g             51

<210> SEQ ID NO 37
<211> LENGTH: 52
<212> TYPE: DNA
<213> ORGANISM: Unknown

<220> FEATURE:
<223> OTHER INFORMATION: Description of Unknown:
      Potato hairy root sequence

<400> SEQUENCE: 37
cttttcaaga tacccagatc atatgcggca cgacttcttc aagagcgcca tg        52

<210> SEQ ID NO 38
<211> LENGTH: 50
<212> TYPE: DNA
<213> ORGANISM: Unknown
<220> FEATURE:
<223> OTHER INFORMATION: Description of Unknown:
      Potato hairy root sequence

<400> SEQUENCE: 38
cttttcaaga tacccagatc aagcggcacg acttcttcaa gagcgccatg            50

<210> SEQ ID NO 39
<211> LENGTH: 66
<212> TYPE: DNA
<213> ORGANISM: Unknown
<220> FEATURE:
<223> OTHER INFORMATION: Description of Unknown:
      Potato hairy root sequence

<400> SEQUENCE: 39
gtgttcaatg cttttcaaga tacccagatc atatgcgcca ccccttttcc aaaagccccc    60
cgcgtg                                                              66

<210> SEQ ID NO 40
<211> LENGTH: 52
<212> TYPE: DNA
<213> ORGANISM: Unknown
<220> FEATURE:
<223> OTHER INFORMATION: Description of Unknown:
      Potato hairy root sequence

<400> SEQUENCE: 40
cttttcaaga tacccagatc ataagcggca cgacttcttc aagagcgcca tg        52

<210> SEQ ID NO 41
<211> LENGTH: 54
<212> TYPE: DNA
<213> ORGANISM: Unknown
<220> FEATURE:
<223> OTHER INFORMATION: Description of Unknown:
      Potato hairy root sequence

<400> SEQUENCE: 41
cttttcaaga tacccagatc atatgagcgg cacgacttct tcaagagcgc catg       54

<210> SEQ ID NO 42
<211> LENGTH: 46
<212> TYPE: DNA
<213> ORGANISM: Unknown
<220> FEATURE:
<223> OTHER INFORMATION: Description of Unknown:
      Potato hairy root sequence

<400> SEQUENCE: 42
cttttcaaga tacccaaagc ggcacgactt cttcaagagc gccatg                46

<210> SEQ ID NO 43
<211> LENGTH: 48
<212> TYPE: DNA

-continued

```
<213> ORGANISM: Solanum tuberosum

<400> SEQUENCE: 43
tacagtgatg cagaaatagt cgttgagggg attgatgttg gcgttaat                48
```